(12) United States Patent
Herr et al.

(10) Patent No.: US 10,485,681 B2
(45) Date of Patent: Nov. 26, 2019

(54) EXOSKELETONS FOR RUNNING AND WALKING

(75) Inventors: Hugh M. Herr, Somerville, MA (US); Conor Walsh, Cambridge, MA (US); Daniel Joseph Paluska, Somerville, MA (US); Andrew Valiente, Chicago, IL (US); Kenneth Pasch, Dover, MA (US); William Grand, Roxbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/859,765

(22) Filed: Aug. 19, 2010

(65) Prior Publication Data
US 2011/0040216 A1    Feb. 17, 2011

Related U.S. Application Data

(63) Continuation of application No. 11/600,291, filed on Nov. 15, 2006, now abandoned, which is a
(Continued)

(51) Int. Cl.
*A61F 5/00* (2006.01)
*A61F 2/68* (2006.01)
(Continued)

(52) U.S. Cl.
CPC .................. *A61F 2/68* (2013.01); *A61F 2/60* (2013.01); *A61F 5/0102* (2013.01);
(Continued)

(58) Field of Classification Search
CPC .... B25J 9/0006; A61H 3/00; A61H 2003/007; A61H 3/008; A61F 5/00; A61F 5/0102;
(Continued)

(56) References Cited

U.S. PATENT DOCUMENTS 2,489,291 A   11/1949   Henschke et al.
2,529,968 A   11/1950   Sartin
(Continued)

FOREIGN PATENT DOCUMENTS

CN   101061984 A   10/2007
CN   101111211 A   1/2008
(Continued)

OTHER PUBLICATIONS

Herr, Hugh et al. "New Horizons for Orthotic and Prosthetic Technology: Artificial Muscle for Ambulation," The MIT Media Laboratory, pp. 1-9, 2004.
(Continued)

*Primary Examiner* — Victoria J Hicks
(74) *Attorney, Agent, or Firm* — Hamilton, Brook, Smith & Reynolds, P.C.

(57) ABSTRACT

An exoskeleton worn by a human user consists of a rigid pelvic harness, worn about the waist of the user, and exoskeleton leg structures, each of which extends downwardly alongside one of the human user's legs. The leg structures include hip, knee, and ankle joints connected by adjustable length thigh and shin members. The hip joint that attaches the thigh structure to the pelvic harness includes a passive spring or an active actuator to assist in lifting the exoskeleton and the human user with respect to the ground surface upon which the user is walking and to propel the exoskeleton and human user forward. A controllable damper operatively arrests the movement of the knee joint at controllable times during the walking cycle and a spring located at the ankle and foot member stores and releases energy during walking.

8 Claims, 54 Drawing Sheets

Related U.S. Application Data continuation-in-part of application No. 11/395,448, filed on Mar. 31, 2006, now abandoned, and a continuation-in-part of application No. 11/499,853, filed on Aug. 4, 2006, now Pat. No. 7,313,463, and a continuation-in-part of application No. 11/495,140, filed on Jul. 29, 2006, now abandoned, which is a continuation-in-part of application No. 11/395,448, filed on Mar. 31, 2006, now abandoned.

(60) Provisional application No. 60/736,929, filed on Nov. 15, 2005, provisional application No. 60/666,876, filed on Mar. 31, 2005, provisional application No. 60/704,517, filed on Aug. 1, 2005, provisional application No. 60/705,651, filed on Aug. 4, 2005.

(51) Int. Cl.

| | | |
|---|---|---|
| *A61F 2/60* | (2006.01) | |
| *A61F 5/01* | (2006.01) | |
| *B25J 9/00* | (2006.01) | |
| *B25J 19/00* | (2006.01) | |
| *B62D 57/032* | (2006.01) | |
| *A61F 2/64* | (2006.01) | |
| *A61F 2/66* | (2006.01) | |
| *A61F 2/50* | (2006.01) | |
| *A61F 2/70* | (2006.01) | |
| *A61F 2/76* | (2006.01) | |

(52) U.S. Cl.
CPC ......... *B25J 9/0006* (2013.01); *B25J 19/0008* (2013.01); *B62D 57/032* (2013.01); *A61F 2/605* (2013.01); *A61F 2/64* (2013.01); *A61F 2/6607* (2013.01); *A61F 2002/5003* (2013.01); *A61F 2002/503* (2013.01); *A61F 2002/5004* (2013.01); *A61F 2002/5033* (2013.01); *A61F 2002/5073* (2013.01); *A61F 2002/5075* (2013.01); *A61F 2002/5093* (2013.01); *A61F 2002/607* (2013.01); *A61F 2002/6614* (2013.01); *A61F 2002/6818* (2013.01); *A61F 2002/6845* (2013.01); *A61F 2002/701* (2013.01); *A61F 2002/704* (2013.01); *A61F 2002/764* (2013.01); *A61F 2002/7625* (2013.01); *A61F 2002/7635* (2013.01); *A61F 2002/7645* (2013.01); *A61F 2002/7695* (2013.01)

(58) Field of Classification Search
CPC ...... A61F 2005/0146; A61F 2005/0148; A61F 2005/0144; A61F 2005/0132; A61F 5/0123; A61F 2/60; A61F 2/604; A61F 2002/607; A61F 2002/608; A61F 2/605
USPC .......................................................... 602/16
See application file for complete search history.

(56) References Cited

U.S. PATENT DOCUMENTS

| | | | |
|---|---|---|---|
| 3,016,760 A | 1/1962 | Wrighton et al. | |
| 3,098,645 A | 7/1963 | Owens | |
| 3,207,497 A | 9/1965 | Schoonover | |
| 3,449,769 A | 7/1969 | Mizen | |
| 3,844,279 A * | 10/1974 | Konvalin | A61F 5/0125 602/16 |
| 3,871,032 A | 3/1975 | Karas | |
| 3,916,450 A | 11/1975 | Minor | |
| 4,442,390 A | 4/1984 | Davis | |
| 4,463,291 A | 7/1984 | Usry | |
| 4,518,307 A | 5/1985 | Bloch | |
| 4,532,462 A | 7/1985 | Washbourn et al. | |
| 4,546,295 A | 10/1985 | Wickham et al. | |
| 4,546,296 A | 10/1985 | Washbourn et al. | |
| 4,546,297 A | 10/1985 | Washbourn et al. | |
| 4,546,298 A | 10/1985 | Wickham et al. | |
| 4,569,352 A | 2/1986 | Petrofsky et al. | |
| 4,600,357 A | 7/1986 | Coules | |
| 4,657,470 A | 4/1987 | Clarke et al. | |
| 4,843,921 A | 7/1989 | Kremer | |
| 4,865,376 A | 9/1989 | Leaver et al. | |
| 4,872,665 A * | 10/1989 | Chareire | A61H 1/0237 482/51 |
| 4,872,803 A | 10/1989 | Asakawa | |
| 4,909,535 A | 3/1990 | Clark et al. | |
| 4,921,293 A | 5/1990 | Ruoff et al. | |
| 4,921,393 A | 5/1990 | Andeen et al. | |
| 4,923,474 A | 5/1990 | Klasson et al. | |
| 4,923,475 A | 5/1990 | Gosthnian et al. | |
| 4,936,295 A * | 6/1990 | Crane | A61F 5/0111 36/89 |
| 4,964,402 A | 10/1990 | Grim et al. | |
| 4,989,161 A | 1/1991 | Oaki | |
| 5,012,591 A | 5/1991 | Asakawa | |
| 5,049,797 A | 9/1991 | Phillips | |
| 5,062,673 A | 11/1991 | Mimura | |
| 5,088,478 A | 2/1992 | Grim | |
| 5,092,902 A | 3/1992 | Adams et al. | |
| 5,112,296 A | 5/1992 | Beard et al. | |
| 5,174,168 A | 12/1992 | Takagi et al. | |
| 5,181,933 A | 1/1993 | Phillips | |
| 5,252,102 A | 10/1993 | Singer et al. | |
| 5,294,873 A | 3/1994 | Seraji | |
| RE34,661 E | 7/1994 | Grim | |
| 5,327,790 A | 7/1994 | Levin et al. | |
| 5,367,790 A | 11/1994 | Gamow et al. | |
| 5,383,939 A | 1/1995 | James | |
| 5,405,409 A | 4/1995 | Knoth | |
| 5,442,270 A | 8/1995 | Tetsuaki | |
| 5,443,521 A | 8/1995 | Knoth et al. | |
| 5,456,341 A | 10/1995 | Garnjost et al. | |
| 5,458,143 A | 10/1995 | Herr | |
| 5,476,441 A | 12/1995 | Durfee et al. | |
| 5,502,363 A | 3/1996 | Tasch et al. | |
| 5,514,185 A | 5/1996 | Phillips | |
| 5,556,422 A | 9/1996 | Powell, III et al. | |
| 5,571,205 A | 11/1996 | James | |
| 5,643,332 A | 7/1997 | Stein | |
| 5,650,704 A | 7/1997 | Pratt et al. | |
| 5,662,693 A | 9/1997 | Johnson et al. | |
| 5,701,686 A | 12/1997 | Herr et al. | |
| 5,718,925 A | 2/1998 | Kristinsson et al. | |
| 5,748,845 A | 5/1998 | Labun et al. | |
| 5,776,205 A | 7/1998 | Phillips | |
| 5,865,770 A | 2/1999 | Schectman | |
| 5,885,809 A | 3/1999 | Effenberger et al. | |
| 5,888,212 A | 3/1999 | Petrofsky et al. | |
| 5,888,213 A | 3/1999 | Sears et al. | |
| 5,898,948 A | 5/1999 | Kelly et al. | |
| 5,910,720 A | 6/1999 | Williamson et al. | |
| 5,932,230 A | 8/1999 | DeGrate | |
| 5,944,760 A | 8/1999 | Christensen | |
| 5,971,729 A | 10/1999 | Kristinsson et al. | |
| 5,972,036 A | 10/1999 | Kristinsson et al. | |
| 5,980,435 A | 11/1999 | Joutras et al. | |
| 6,029,374 A * | 2/2000 | Herr | A43B 5/06 36/151 |
| 6,056,712 A | 5/2000 | Grim | |
| 6,067,892 A | 5/2000 | Erickson | |
| 6,071,313 A | 6/2000 | Phillips | |
| 6,136,039 A | 10/2000 | Kristinsson et al. | |
| 6,144,385 A | 11/2000 | Girard | |
| 6,202,806 B1 | 3/2001 | Sandrin et al. | |
| 6,223,648 B1 | 5/2001 | Erickson | |
| 6,240,797 B1 | 6/2001 | Morishima et al. | |
| 6,267,742 B1 | 7/2001 | Krivosha et al. | |
| 6,416,703 B1 | 7/2002 | Kristinsson et al. | |
| 6,443,993 B1 | 9/2002 | Koniuk | |
| 6,456,884 B1 | 9/2002 | Kenney | |
| 6,478,826 B1 | 11/2002 | Phillips et al. | |
| 6,485,776 B2 | 11/2002 | Janusson et al. | |

(56) References Cited

U.S. PATENT DOCUMENTS

| | | | |
|---|---|---|---|
| 6,507,757 B1 | 1/2003 | Swain et al. | |
| 6,511,512 B2 | 1/2003 | Phillips et al. | |
| 6,517,503 B1 | 2/2003 | Naft et al. | |
| 6,532,400 B1 | 3/2003 | Jacobs | |
| 6,585,774 B2 | 7/2003 | Dean, Jr. et al. | |
| 6,589,289 B2 | 7/2003 | Ingimarsson | |
| 6,592,539 B1 | 7/2003 | Einarsson et al. | |
| 6,610,101 B2 | 8/2003 | Herr et al. | |
| 6,626,952 B2 | 9/2003 | Janusson et al. | |
| 6,660,042 B1 | 12/2003 | Curcie et al. | |
| 6,666,796 B1 * | 12/2003 | MacCready, Jr. | 482/51 |
| 6,706,364 B2 | 3/2004 | Janusson et al. | |
| 6,752,774 B2 | 6/2004 | Townsend et al. | |
| 6,764,520 B2 | 7/2004 | Deffenbaugh et al. | |
| 6,811,571 B1 | 11/2004 | Phillips | |
| D503,480 S | 3/2005 | Ingimundarson et al. | |
| D503,802 S | 4/2005 | Bjarnason | |
| 6,887,279 B2 | 5/2005 | Phillips et al. | |
| 6,923,834 B2 | 8/2005 | Karason | |
| 6,936,073 B2 | 8/2005 | Karason | |
| 6,942,629 B2 * | 9/2005 | Hepburn et al. | 602/16 |
| 6,945,947 B2 | 9/2005 | Ingimundarson et al. | |
| 6,966,882 B2 | 11/2005 | Horst | |
| 6,969,408 B2 | 11/2005 | Lecomte et al. | |
| 7,001,563 B2 | 2/2006 | Janusson et al. | |
| 7,025,793 B2 | 4/2006 | Egilsson | |
| 7,029,500 B2 | 4/2006 | Martin | |
| 7,037,283 B2 | 5/2006 | Karason et al. | |
| D523,149 S | 6/2006 | Bjarnason | |
| 7,063,727 B2 | 6/2006 | Phillips et al. | |
| 7,077,818 B2 | 7/2006 | Ingimundarson et al. | |
| 7,094,058 B2 | 8/2006 | Einarsson | |
| 7,094,212 B2 | 8/2006 | Karason et al. | |
| D527,825 S | 9/2006 | Ingimundarson et al. | |
| D529,180 S | 9/2006 | Ingimundarson et al. | |
| 7,101,487 B2 | 9/2006 | Hsu et al. | |
| 7,105,122 B2 | 9/2006 | Karason | |
| 7,107,180 B2 | 9/2006 | Karason | |
| 7,118,601 B2 | 10/2006 | Yasui et al. | |
| 7,118,602 B2 | 10/2006 | Bjarnason | |
| 7,136,722 B2 | 11/2006 | Nakamura et al. | |
| D533,280 S | 12/2006 | Wyatt et al. | |
| 7,144,429 B2 | 12/2006 | Carstens | |
| 7,145,305 B2 | 12/2006 | Takenaka et al. | |
| 7,154,017 B2 | 12/2006 | Sigurjonsson et al. | |
| 7,161,056 B2 | 1/2007 | Gudnason et al. | |
| 7,169,188 B2 | 1/2007 | Carstens | |
| 7,169,189 B2 | 1/2007 | Bjarnason et al. | |
| 7,169,190 B2 | 1/2007 | Phillips et al. | |
| 7,198,071 B2 * | 4/2007 | Bisbee, III | A61F 2/5044 141/65 |
| 7,198,610 B2 | 4/2007 | Ingimundarson et al. | |
| 7,217,060 B2 | 5/2007 | Ingimarsson | |
| 7,220,889 B2 | 5/2007 | Sigurjonsson et al. | |
| 7,223,899 B2 | 5/2007 | Sigurjonsson | |
| 7,227,050 B2 | 6/2007 | Sigurjonsson et al. | |
| 7,230,154 B2 | 6/2007 | Sigurjonsson | |
| 7,235,108 B2 | 6/2007 | Carstens | |
| 7,240,876 B2 | 7/2007 | Doubleday et al. | |
| 7,266,910 B2 | 9/2007 | Ingimundarson | |
| 7,270,644 B2 | 9/2007 | Ingimundarson | |
| 7,279,009 B2 | 10/2007 | Herr et al. | |
| 7,288,076 B2 | 10/2007 | Grim et al. | |
| 7,295,892 B2 | 11/2007 | Herr et al. | |
| RE39,961 E | 12/2007 | Petrofsky et al. | |
| 7,303,538 B2 | 12/2007 | Grim et al. | |
| 7,304,202 B2 | 12/2007 | Sigurjonsson et al. | |
| 7,311,686 B1 | 12/2007 | Iglesias et al. | |
| 7,313,463 B2 | 12/2007 | Herr et al. | |
| D558,884 S | 1/2008 | Ingimundarson et al. | |
| 7,314,490 B2 | 1/2008 | Bédard et al. | |
| 7,335,233 B2 | 2/2008 | Hsu et al. | |
| 7,347,877 B2 | 3/2008 | Clausen et al. | |
| D567,072 S | 4/2008 | Ingimundarson et al. | |
| 7,371,262 B2 | 5/2008 | Lecomte et al. | |
| 7,377,944 B2 | 5/2008 | Janusson et al. | |
| RE40,363 E | 6/2008 | Grim et al. | |
| 7,381,860 B2 | 6/2008 | Gudnason et al. | |
| 7,393,364 B2 | 7/2008 | Martin | |
| 7,396,975 B2 | 7/2008 | Sigurjonsson et al. | |
| 7,402,721 B2 | 7/2008 | Sigurjonsson et al. | |
| 7,411,109 B2 | 8/2008 | Sigurjonsson et al. | |
| D576,781 S | 9/2008 | Chang et al. | |
| D577,828 S | 9/2008 | Ingimundarson et al. | |
| 7,423,193 B2 | 9/2008 | Sigurjonsson et al. | |
| 7,427,297 B2 | 9/2008 | Patterson et al. | |
| 7,429,253 B2 | 9/2008 | Shimada et al. | |
| 7,431,708 B2 | 10/2008 | Sreeramagiri | |
| 7,431,737 B2 | 10/2008 | Ragnarsdottir et al. | |
| 7,438,843 B2 | 10/2008 | Asgeirsson | |
| 7,449,005 B2 | 11/2008 | Pickering et al. | |
| 7,455,696 B2 | 11/2008 | Bisbee, III et al. | |
| D583,956 S | 12/2008 | Chang et al. | |
| 7,459,598 B2 | 12/2008 | Sigurjonsson et al. | |
| 7,465,281 B2 | 12/2008 | Grim et al. | |
| 7,465,283 B2 | 12/2008 | Grim et al. | |
| 7,468,471 B2 | 12/2008 | Sigurjonsson et al. | |
| 7,470,830 B2 | 12/2008 | Sigurjonsson et al. | |
| 7,485,152 B2 | 2/2009 | Haynes et al. | |
| 7,488,349 B2 | 2/2009 | Einarsson | |
| 7,488,864 B2 | 2/2009 | Sigurjonsson et al. | |
| D588,753 S | 3/2009 | Ingimundarson et al. | |
| 7,503,937 B2 | 3/2009 | Asgeirsson et al. | |
| 7,513,880 B2 | 4/2009 | Ingimundarson et al. | |
| 7,513,881 B1 | 4/2009 | Grim et al. | |
| D592,755 S | 5/2009 | Chang et al. | |
| D592,756 S | 5/2009 | Chang et al. | |
| 7,527,253 B2 | 5/2009 | Sugar et al. | |
| 7,531,006 B2 | 5/2009 | Clausen et al. | |
| 7,531,711 B2 | 5/2009 | Sigurjonsson et al. | |
| 7,534,220 B2 | 5/2009 | Cormier et al. | |
| 7,544,214 B2 | 6/2009 | Gramnas | |
| 7,549,970 B2 | 6/2009 | Tweardy | |
| D596,301 S | 7/2009 | Campos et al. | |
| 7,578,799 B2 | 8/2009 | Thorsteinsson et al. | |
| 7,581,454 B2 | 9/2009 | Clausen et al. | |
| 7,597,672 B2 | 10/2009 | Kruijsen et al. | |
| 7,597,674 B2 | 10/2009 | Hu et al. | |
| 7,597,675 B2 | 10/2009 | Ingimundarson et al. | |
| 7,618,463 B2 | 11/2009 | Oddsson et al. | |
| 7,632,315 B2 | 12/2009 | Egilsson | |
| 7,637,957 B2 | 12/2009 | Ragnarsdottir et al. | |
| 7,637,959 B2 | 12/2009 | Clausen et al. | |
| 7,641,700 B2 | 1/2010 | Yasui | |
| 7,650,204 B2 | 1/2010 | Dariush | |
| 7,662,191 B2 | 2/2010 | Asgeirsson | |
| D611,322 S | 3/2010 | Robertson | |
| 7,674,212 B2 | 3/2010 | Kruijsen et al. | |
| 7,691,154 B2 | 4/2010 | Asgeirsson et al. | |
| 7,696,400 B2 | 4/2010 | Sigurjonsson et al. | |
| 7,704,218 B2 | 4/2010 | Einarsson et al. | |
| D616,555 S | 5/2010 | Thorgilsdottir et al. | |
| D616,556 S | 5/2010 | Hu | |
| 7,713,225 B2 | 5/2010 | Ingimundarson et al. | |
| D616,996 S | 6/2010 | Thorgilsdottir et al. | |
| D616,997 S | 6/2010 | Thorgilsdottir et al. | |
| D618,359 S | 6/2010 | Einarsson | |
| 7,727,174 B2 | 6/2010 | Chang et al. | |
| 7,736,394 B2 | 6/2010 | Bedard et al. | |
| 7,745,682 B2 | 6/2010 | Sigurjonsson et al. | |
| D620,124 S | 7/2010 | Einarsson | |
| 7,749,183 B2 | 7/2010 | Ingimundarson et al. | |
| 7,749,281 B2 | 7/2010 | Egilsson | |
| 7,762,973 B2 | 7/2010 | Einarsson et al. | |
| 7,770,842 B2 | 8/2010 | Benson | |
| 7,771,488 B2 | 8/2010 | Asgeirsson et al. | |
| 7,780,741 B2 | 8/2010 | Janusson et al. | |
| 7,794,418 B2 | 9/2010 | Ingimundarson et al. | |
| 7,794,505 B2 | 9/2010 | Clausen et al. | |
| 7,811,333 B2 | 10/2010 | Jonsson et al. | |
| 7,811,334 B2 | 10/2010 | Ragnarsdottir et al. | |
| D627,079 S | 11/2010 | Robertson | |
| 7,833,181 B2 | 11/2010 | Cormier et al. | |
| 7,842,848 B2 | 11/2010 | Janusson et al. | |

(56) References Cited

U.S. PATENT DOCUMENTS

| | | |
|---|---|---|
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| RE42,903 E | 11/2011 | Deffenbaugh et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,202,325 B2 | 6/2012 | Albrecht-Laatsch et al. |
| 8,287,477 B1 | 10/2012 | Herr et al. |
| 8,371,691 B2 | 2/2013 | Herr et al. |
| 8,376,971 B1 | 2/2013 | Herr et al. |
| 8,419,804 B2 | 4/2013 | Herr et al. |
| 8,500,823 B2 | 8/2013 | Herr et al. |
| 8,512,415 B2 | 8/2013 | Herr et al. |
| 8,734,528 B2 | 5/2014 | Herr et al. |
| 8,864,846 B2 | 10/2014 | Herr et al. |
| 8,870,967 B2 | 10/2014 | Herr et al. |
| 9,149,370 B2 | 10/2015 | Herr et al. |
| 9,221,177 B2 | 12/2015 | Herr et al. |
| 9,339,097 B2 | 5/2016 | Herr et al. |
| 9,339,397 B2 | 5/2016 | Herr et al. |
| 9,539,117 B2 | 1/2017 | Herr et al. |
| 9,975,249 B2 | 5/2018 | Herr et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0181289 A1 | 9/2004 | Bedard et al. |
| 2005/0007834 A1 | 1/2005 | Hidaka |
| 2005/0038525 A1 | 2/2005 | Doddroe et al. |
| 2005/0043614 A1 | 2/2005 | Huizenga et al. |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2005/0192677 A1 | 9/2005 | Ragnarsdottir et al. |
| 2005/0209707 A1 | 9/2005 | Phillips et al. |
| 2005/0228515 A1 | 10/2005 | Musallam et al. |
| 2006/0004307 A1 | 1/2006 | Horst |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0122711 A1 | 6/2006 | Bedard et al. |
| 2006/0211956 A1 | 9/2006 | Sankai |
| 2006/0213305 A1 | 9/2006 | Sugar et al. |
| 2006/0224246 A1 | 10/2006 | Clausen et al. |
| 2006/0249315 A1 | 11/2006 | Herr et al. |
| 2006/0258967 A1* | 11/2006 | Fujil et al. ............... 602/23 |
| 2006/0264790 A1 | 11/2006 | Kruijsen et al. |
| 2006/0276728 A1* | 12/2006 | Ashihara et al. .......... 601/5 |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0162152 A1 | 7/2007 | Herr et al. |
| 2007/0267791 A1 | 11/2007 | Hollander et al. |
| 2008/0114272 A1 | 5/2008 | Herr et al. |
| 2008/0155444 A1 | 6/2008 | Pannese et al. |
| 2008/0169729 A1 | 7/2008 | Asai |
| 2009/0030530 A1 | 1/2009 | Martin |
| 2009/0222105 A1 | 9/2009 | Clausen |
| 2009/0265018 A1 | 10/2009 | Goldfarb et al. |
| 2010/0113980 A1 | 5/2010 | Herr et al. |
| 2010/0113988 A1 | 5/2010 | Matsuoka et al. |
| 2010/0241242 A1 | 9/2010 | Herr et al. |
| 2010/0256537 A1 | 10/2010 | Menga |
| 2010/0324699 A1 | 12/2010 | Herr et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2012/0136459 A1 | 5/2012 | Herr et al. |
| 2012/0209405 A1 | 8/2012 | Herr et al. |
| 2012/0271433 A1 | 10/2012 | Galea et al. |
| 2013/0110256 A1 | 5/2013 | Herr et al. |
| 2013/0158444 A1 | 6/2013 | Herr et al. |
| 2013/0197318 A1 | 8/2013 | Herr et al. |
| 2013/0310979 A1 | 11/2013 | Herr et al. |
| 2014/0046455 A1 | 2/2014 | Herr et al. |
| 2014/0088729 A1 | 3/2014 | Herr et al. |
| 2014/0257519 A1 | 9/2014 | Herr et al. |
| 2015/0051710 A1 | 2/2015 | Herr et al. |
| 2016/0207201 A1 | 7/2016 | Herr et al. |
| 2016/0228265 A1 | 8/2016 | Herr et al. |

(56) References Cited

U.S. PATENT DOCUMENTS

| | | |
|---|---|---|
| 2016/0338857 A1 | 11/2016 | Herr et al. |
| 2017/0049587 A1 | 2/2017 | Herr et al. |

FOREIGN PATENT DOCUMENTS

| | | |
|---|---|---|
| EP | 1169982 A1 | 1/2002 |
| EP | 1393866 | 3/2004 |
| EP | 1408892 | 4/2004 |
| EP | 1534117 | 6/2005 |
| JP | 2008-87143 A | 4/2008 |
| WO | WO 2001/054630 A1 | 8/2001 |
| WO | WO 2003/005934 A2 | 1/2003 |
| WO | WO 2003/03068453 | 8/2003 |
| WO | WO 2004/017872 A1 | 3/2004 |
| WO | WO 2004/019832 A1 | 3/2004 |
| WO | WO 2010/027968 A2 | 3/2010 |
| WO | WO 2010/088616 | 8/2010 |
| WO | WO 2010/088635 A1 | 8/2010 |

OTHER PUBLICATIONS

Williamson, Matthew M., "Series Elastic Actuators," MIT Artificial Intelligence Laboratory, Jan. 1995.

Au, S.K. et al., "Powered Ankle-Foot Prosthesis for the Improvement of Amputee Ambulation," paper presented at the Proceedings of the 29$^{th}$ Annual International Conference of the IEEE Eng. Med. Bio. Soc., Cité Internationale, Lyon, France, (Aug. 2007).

International Search Report and Written Opinion for corresponding International Application No. PCT/US2010/022783, dated May 4, 2010.

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.

Blaya, J.A. et al., "Adaptive Control of a Variable-Impedance Ankle-Foot Orthosis to Assist Drop Foot Gait," Artificial Intelligence Lab and Harvard—MIT Division Health Sciences and Technology, Boston, MA, 30 pages.

Blaya, J.A. et al., "Active Ankle Foot Orthoses (AAFO)," Retrieved from: http://www.ai,mit.edu. Artificial Intelligence Laboratory, Massachusetts Institute of Technology, Cambridge, Massachusetts, 3 pages.

Dollar, et al., "Lower Extremity Exoskeletons and Active Orthoses: Challenges and State-of-the-Art," *IEEE Transcations on Robotics*, vol. 24, No. 1, Feb. 2008, 15 pages.

Drake, C., "Foot & Ankle Splints or Orthoses," HemiHelp Information Sheet, London, United Kingdom, 3 pages, http://www.hemihelp.org.uk/leaflets/hbleaflets90.htm Retrieved on: Jun. 20, 2003.

Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).

Hogan, N., "Impedance Control: An Approach to Manipulation: Part II—Implementation," *Journal of Dynamic Systems, Measurement and Control*, 107: 8-16 (1985).

Hogan, N., "Impedance Control: An Approach to Manipulation: Part III—Application," *Journal of Dynamics Systems, Measurement and Control*, 107: 17-24 (1985).

Kim, J.-H. et al., "Realization of Dynamic Walking for the Humaniod Robot Platform KHR-1," *Advanced Robotics*, 18(7): 749-768, (2004).

Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).

Klute, G.K. et al., "Artificial Muscles: Actuators for Biorobotic Systems," *The International Journal of Robotics Research*, 21(4): 295-309 (2002).

Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.

Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al., "Intelligent Transtibial Prostheses with Muscle-Like Actuators," 2002 American Physiological Society Intersociety Meeting: The Power of Comparative Physiology: Evolution, Integration, and Applied, 1 page.

Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).

Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.

Klute, G.K. et al., "Variable Stiffness Prosthesis for Transtibial Amputees," Dept of Veteran Affairs, Seattle, WA USA, 2 pages.

International Search Report and Written Opinion for International Application No. PCT/US2009/055600, dated Apr. 29, 2010 (23 pages).

International Search Report and Written Opinion for International Application No. PCT/US2010/047279, dated Jan. 19, 2011 (11 pages).

International Search Report and Written Opinion for International Application No. PCT/US2011/031105, dated Oct. 11, 2011 (16 pages).

J. Hitt et al., "The Sparky (Spring Ankle with Regenerative Kinetics) Projects: Design and Analysis of a Robotic Transtibial prosthesis with Regenerative Kinetics," in Proc. IEEE Int. Conf. Robot. Autom., Orlando, Fla., pp. 2939-2945, May 2006.

Sup, F. et al., "Design and Control of a Powered Transfemoral Prosthesis," *The International Journal of Robotics Research*, vol. 27, No. 2, pp. 263-273 (2008).

Geyer, H. et al., "A Muscle-Reflex Model That Encodes Principles of Legged Mechanics Predicts Human Walking Dynamics and Muscle Activities," *IEEE Transactions on Neural Systems and Rehabilitation Engineering*, vol. 18, No. 3, pp. 263-273 (Jun. 2010).

Geyer, H. et al., "Positive Force Feedback in Bouncing Gaits?," *Proc. R Society. Lond. B*, 270, pp. 2173-2183 (2003).

Abbas, J.J. et al., "Neural Network Control of Functional Neuromuscular Stimulation Systems: Computer Simulation Studies," *IEEE Transactions on Biomedical Engineering*, vol. 42, No. 11, Nov. 1995, pp. 1117-1127.

Abul-Haj, C.J. et al., "Functional Assessment of Control Systems for Cybernetic Elbow Prostheses—Part II: Application of the Technique," *IEEE Transactions on Biomedical Engineering*, vol. 17, No. 11, Nov. 1990, pp. 1037-1047.

Akazawa, K. et al., "Biomimetic EMG-Prosthesis-Hand, 18$^{th}$ Annual International Conference of the IEEE Engineering in Medicine and Biology Society," Amsterdam 1996, pp. 535 and 536.

Aminian, K. et al., "Estimation of Speed and Incline of Walking Using Neural Network," *IEEE Transactions of Instrumentation and Measurement*, 44(3): 743-746 (1995).

Anderson, F.C. et al., "Dynamic Optimization of Human Walking," *Journal of Biomechanical Engineering*, 123: 381-390 (2001).

Andrews, B.J. et al., "Hybrid FES Orthosis Incorporating Closed Loop Control and Sensory Feedback," *J. Biomed. Eng.*, 10: 189-195(1988).

Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.

Au, S.K. et al., "Biomechanical Design of a Powered Ankle-Foot Prosthesis," Proceedings of the 2007 IEEE 10$^{th}$ International Conference on Rehabilitation Robotics, Noordwijk, The Netherlands, Jun. 12-15, pp. 298-303.

(56) References Cited

OTHER PUBLICATIONS

Au, S.K. et al., "An EMG-Position Controlled System for an Active Ankle-Foot Prosthesis: An Initial Experimental Study," Proceedings of the 2005 IEEE 9th International Conference on Rehabilitation Robotics, Chicago, IL., pp. 375-379.
Au, S.K. et al., "Initial Experimental Study on Dynamic Interaction Between an Amputee and a Powered Ankle-Foot Prostheses," Harvard—MIT Division of Health Sciences and Technology, MIT, Cambridge, MA.
Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.
Au, S.K. et al., "Powered Ankle-Foot Prosthesis Improves Walking Metabolic Economy," *IEEE Transactions on Robotics*, 25(1): 51-66 (2009).
Au, S.K. et al., "Powered Ankle—Foot Prosthesis for the Improvement of Amputee Ambulation," paper presented at the Proceedings of the 29th Annual International Conference of the IEEE EMBS Cité Internationale, Lyon, France, (Aug. 2007).
Au, S. et al., "Powered Ankle-Foot Prosthesis to Assist Level-Ground and Stair-Descent Gaits," *Neural Networks*, 21: 654-666 (2008).
Barth, D.G. et al., "Gait Analysis and Energy Cost of Below-Knee Amputees Wearing Six Different Prosthetic Feet," *JPO*, 4(2): 63 (1992).
Bateni, H. et al., "Kinematic and Kinetic Variations of Below-Knee Amputee Gait," *JPO*, 14(1):1-12 (2002).
Baten, Chris T.M. et al., "Inertial Sensing in Ambulatory Back Load Estimation," paper presented at the 18th Annual International Conference of the IEEE Engineering in Medicine and Biology Society, Amsterdam, 1996, pp. 497-498.
Blaya, J. et al., "Active Ankle Foot Orthoses (AAFO)," Artificial Intelligence Laboratory, Massachusetts Institute of Technology, Cambridge, MA, pp. 275-277.
Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).
Blaya, J.A. et al., "Force-Controllable Ankle-Foot Orthosis (AFO) to Assist Drop Foot Gait," Massachusetts Institute of Technology, Feb. 2003, pp. 1-96.
Blickhan, R., "The Spring-Mass Model for Running and Hopping," *J. Biomechanics*, 22(11 /12): 1217-1227 (1989).
Bortz, J.E. "A New Mathematical Formulation for Strapdown Inertial Navigation," *IEEE Transactions on Aerospace and Electronic Systems*, AES-7(1): 61-66 (1971).
Bouten, C.V. et al., "Assessment of Energy Expenditure for Physical Activity Using a Triaxial Accelerometer," *Medicine and Science in Sports and Exercise*, pp. 1516-1523.
Brockway, J.M., "Derivation of Formulae Used to Calculate Energy Expenditure in Man," *Human Nutrition: Clinical Nutrition* (1987), 41C, pp. 463-471.
Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46.
AJG The American Journal of Gastroenterology, "Symptoms Diagnosis," 105(4): 1-875 (2010).
Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.
American Journal of Physical Medicine & Rehabilitation, 71(5): 1-278 (1992).
Colgate, James Edward, "The Control of Dynamically Interacting Systems," Massachusetts Institute of Technology, Aug. 1988, pp. 1-15.
Collins, S.H. et al., "Controlled Energy Storage and Return Prosthesis Reduces Metabolic Cost of Walking," ISB XXth Congress—ASB 29th Annual Meeting, Jul. 31-Aug. 5, Cleveland, Ohio, pp. 804.
Collins, S.H. et al., "Efficient Bipedal Robots Based on Passive-Dynamic Walkers," Feb. 11, 2005, pp. 1-8.
Crago, P.E. et al., "New Control Strategies for Neuroprosthetic Systems," *Journal of Rehabilitation Research and Development*, vol. 33, No. 2, Apr. 1996, pp. 158-172.
Daley, M.A. et al., "Running Stability is Enhanced by a Proximo-Distal Gradient in Joint Neuromechanical Control," *The Journal of Experimental Biology*, vol. 210, pp. 383-394 (Feb. 2007).
Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).
Dietz, V. "Proprioception and Locomotor Disorders," *Nature Reviews*, vol. 3, pp. 781-790 (Oct. 2002).
Dietz, V. "Spinal Cord Pattern Generators for Locomotion," *Clinical Neurophysiology*, vol. 114, Issue 8, pp. 1-12 (Aug. 2003).
Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.
Doke, J. et al., "Mechanics and Energetics of Swinging the Human Leg," *The Journal of Experimental Biology*, vol. 208, pp. 439-445 (2005).
Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.
Donelan, J.M. et al., "Force Regulation of Ankle Extensor Muscle Activity in Freely Walking Cats," *Journal of Neurophysiology*, vol. 101, pp. 360-371 (2009).
Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).
Donelan, J.M. et al., "Simultaneous Positive and Negative External Mechanical Work in Human Walking," *Journal of Biomechanics*, vol. 35, 2002, pp. 117-124 (2002).
HemiHelp, "Ankle & Foot Splints or Orthoses," (AFOs).
HemiHelp, "Foot & Ankle Splints or Orthoses," pp. 1-5.
Drake, C., "Foot & Ankle Splints or Orthoses," pp. 1-3.
Eilenberg, M.F. "A Neuromuscular-Model Based Control Strategy for Powered Ankle-Foot Prostheses," Massachusetts Institute of Technology, pp. 1-90.
Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).
Ekeberg, Ö et al., "Simulations of Neuromuscular Control in Lamprey Swimming," The Royal Society, *Phil. Trans. R. Soc. Land*, vol. 354, pp. 895-902 (1999).
Endo, K. et al.,"A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.
Eppinger, S.D. et al., "Three Dynamic Problems in Robot Force Control," *IEEE Transactions on Robotics and Automation*, vol. 8, No. 6, pp. 772-778 (Dec. 1992).
Esquenazi, A. et al., "Rehabilitation After Amputation," vol. 91, No. 1, pp. 1-22 (Jan. 2001).
Farley, C.T. et al., "Energetics of Walking and Running: Insights From Simulated Reduced-Gravity Experiments," Harvard University, pp. 2709-2712.
Farry, K.A. et al., "Myoelectric Teleoperation of a Complex Robotic Hand," *IEEE Transactions on Robotics and Automation*, vol. 12, No. 5, pp. 775-778 (Oct. 1996).
Featherstone, R., "Robot Dynamics Algorithms," Edinburgh University, pp. 1-173.
Fite, K. et al., "Design and Control of an Electrically Powered Knee Prosthesis," Proceedings of the 2007 IEEE 10th International Conference on Rehabilitation Robotics, Jun. 12-15, The Netherlands, pp. 902-905.

(56) References Cited

OTHER PUBLICATIONS

Flowers, W.C., "A Man-Interactive Simulator System for Above-Knee Prosthetics Studies," MIT, pp. 1-94.
Fod, A. et al., "Automated Derivation of Primitives for Movement Classification," *Autonomous Robots*, vol. 12, No. 1, pp. 39-54 (Jan. 2002).
Frigon, A. et al., "Experiments and Models of Sensorimotor Interactions During Locomotion," *Biological Cybernetics*, vol. 95, pp. 606-627 (2006).
Fujita et al., "Joint Angle Control with Command Filter for Human Ankle Movement Using Functional Electrical Stimulation," IEEE Ninth Annual Conference of the Engineering in Medicine and Biology Society.
Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).
Gates, D.H. Thesis: "Characterizing Ankle Function During Stair Ascent, Descent, and Level Walking for Ankle Prosthesis and Orthosis Design," Boston University, pp. 1-84.
Gerritsen, K.G.M. et al., "Direct Dynamics Simulation of the Impact Phase in Heel-Toe Running," *J. Biomechanics*, vol. 28, No. 6, pp. 661-668 (1995).
Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10 (Date not provided).
Geyer, H. et al., "Compliant Leg Behavior Explains Basic Dynamics of Walking and Running," *Proc. R. Soc. B*, vol. 273, pp. 2861-2867 (2006).
Geyer, H. et al., "Positive Force Feedback in Bouncing Gaits?," *Proc. R. Soc. Lond, B*, vol. 270, pp. 2173-2183 (2003).
Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).
Giszter, S., et al., "Convergent Force Fields Organized in the Frog's Spinal Cord," *Journal of Neuroscience*, 13(2): 467-491 (1993).
Godha, S. et al., "Integrated GPS/INS System for Pedestrian Navigation in a Signal Degraded Environment," University of Calgary, Canada, pp. 1-14.
Goswami, A., "Postural Stability of Biped Robots and the Foot-Rotation Indicator (FRI) Point," *The International Journal of Robotics Research*, vol. 18, No. 6, pp. 523-533 (Jun. 1999).
Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.
Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).
Gregoire, L. et al., "Role of Mono- and Biarticular Muscles in Explosive Movements," *International Journal of Sports Medicine*, vol. 5, No. 6, pp. 299-352 (Dec. 1984).
Grillner, S. and Zangger, P., "On the Central Generation of Locomotion in the Low Spinal Cat," *Experimental Brain Research*, 34: 241-261 (1979).
Grimes, D.L., "An Active Multi-Mode Above-Knee Prosthesis Controller," unpublished doctoral dissertation, Massachusetts Institute of Technology (1979).
Gunther, M. et al., "Human Leg Design: Optimal Axial Alignment Under Constraints," *J. Math. Biol.*, 48: 623-646 (2004).
Günther, M., and Ruder, H., "Synthesis of Two-Dimensional Human Walking: a test of the λ-model," *Biol. Cybern.*, 89: 89-106 (2003).
Gu, W.J., "The Regulation of Angular Momentum During Human Walking," unpublished doctoral dissertation, Massachusetts Institute of Technology (2003).
Brady, M. et al., "Robot Motion: Planning and Control," The MIT Press, Cambridge (1982).

Hansen, A.H., et al., "The Human Ankle During Walking: Implications for Design of Biomimetic Ankle Prostheses," *Journal of Biomechanics*, 37: 1467-1474 (2004).
Hayes, W.C., et al., "Leg Motion Analysis During Gait by Multiaxial Accelerometry: Theoretical Foundations and Preliminary Validations, *Journal of Biomechanical Engineering*," 105: 283-289 (1983).
Heglund, N. et al., "A Simple Design for a Force-Plate to Measure Ground Reaction Forces," *J. Exp. Biol.*, 93: 333-338 (1981).
Herr, H.M. et al., "A Model of Scale Effects in mammalian Quadrupedal Running," *The Journal of Experimental Biology*, 205: 959-967 (2002).
Herr, H.M., and Popovic, M., "Angular Momentum in Human Walking," *The Journal of Experimental Biology*, 211: 467-481 (2008).
Herr, H.M., and McMahon, T.A., "A Trotting Horse Model," *The International Journal of Robotics Research*, 19: 566-581 (2000).
Herr, H.M., and Wilkenfeld, A., "User-adaptive Control of a Magnetorheological Prosthetic Knee," *Industrial Robot: An International Journal*, 30(1): 42-55 (2003).
Heyn, A., et al., "The Kinematics of the Swing Phase Obtained From Accelerometer and Gyroscope Measurements," paper presented at the 18th Annual International Conference of the IEEE Engineering in Medicine and Biology Society, Amsterdam (1996).
Hill, A.V., "The Heat of Shortening and the Dynamic Constants of Muscle," *Proc. R. Soc. Lond.*, 126: 136-195 (1938).
Hirai, K., et al., "The Development of Honda Humanoid Robot," paper presented at the 1998 IEEE International Conference on Robotics & Automation (1998).
Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada (2007).
Hofbaur, M.W., et al., "Hybrid Diagnosis with Unknown Behavioral Modes," Proceedings of the 13th International Workshop on Principles of Diagnosis (DX02) (2002).
Hofbaur, M.W., and Williams, B.C., "Mode Estimation of Probabilistic Hybrid Systems," MIT Space Systems and Artificial Intelligence Laboratories and Graz University of Technology, Department of Automatic Control.
Hof, A.L., et al., "Calf Muscle Moment, Work and Efficiency in Level Walking: Role of Series Elasticity," *J. Biochem.*, 16: 523-537 (1983).
Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).
Hofmann, A.G., "Robust Execution of Bipedal Walking Tasks From Biomechanical Principles," unpublished doctoral dissertation for Massachusetts Institute of Technology (2006).
Hogan, N., "A Review of the Methods of Processing EMG for Use as a Proportional Control Signal," *Biomedical Engineering*, 11(3): 81-86 (1976).
Hogan, N., "Impedance Control—An Approach to Manipulation," unpublished doctoral dissertation for Department of Mechanical Engineering and Laboratory of Manufacturing and Productivity, Massachusetts Institute of Technology, pp. 304-313.
Hogan, N., and Buerger, S.P., "Impedance and Interaction Control, Robots and Automation Handbook."
Hogan, N., "Impedance Control: An Approach to Manipulation, Part III—Applications," *Journal of Dynamic Systems, Measurement, and Control*, 107: 17-24 (1985).
Hogan, N., "Impedance Control: An Approach to Manipulation: Part I—Theory," *Journal of Dynamic Systems, Measurement, and Control*, 107: 1-7 (1985).
Hollander, K.W. et al., "Adjustable Robotic Tendon using a 'Jack Spring'™," Proceedings of the 2005 IEEE, 9th International Conference on Rehabilitation Robotics, Jun. 28-Jul. 1, 2005, Chicago, IL, USA, pp. 113-118.
Howard, R.D., Thesis: "Joint and Actuator Design for Enhanced Stability in Robotic Force Control," Submitted to the Dept. of

(56) References Cited

OTHER PUBLICATIONS

Aeronautics and Astronautics on Aug. 8, 1990 in partial fulfillment of the requirements for the degree of Doctor of Philosophy.

Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).

Huang, Q. et al., "Planning Walking Patterns for a Biped Robot," *IEEE Transactions on Robotics and Automation*, 17(3): 280-289 (Jun. 2001).

Hultborn, H., "Spinal reflexes, mechanisms and concepts: From Eccles to Lundberg and beyond," *Progress in Neurobiology*, 78: 215-232 (2006).

Ijspeert, A.J., "Central pattern generators for locomotion control in animals and robots: a review," *Preprint of Neural Networks*, vol. 21, No. 4, pp. 642-653 (2008).

Ijspeert, A.J. et al., "From swimming to walking with a salamander robot driven by a spinal cord model," pp. 1-5.

Ivashko, D.G. et al., "Modeling the spinal cord neural circuitry controlling cat hindlimb movement during locomotion," *Neurocomputing*, 52-54, pp. 621-629 (2003).

International Search Report and Written Opinion for International Application No. PCT/US2009/055600, dated Apr. 29, 2010.

International Preliminary Report on Patentability for International Application No. PCT/US2010/047279; dated Mar. 15, 2012.

International Search Report and Written Opinion for International Application No. PCT/US2010/047279; dated Jan. 19, 2011.

International Search Report and Written Opinion for International Application No. PCT/US2011/031105, dated Oct. 11, 2011.

Johansson, J.L. et al., "A Clinical Comparison of Variable-Damping and Mechanically Passive Prosthetic Knee Devices," Variable-Damping vs. Mechanically Passive Prosthetic Knees, Aug. 2005.

Johnson, C.T. et al., "Experimental Identification of Friction and Its Compensation in Precise, Position Controlled Mechanisms," *IEEE Transactions on Industry Applications*, vol. 28, No. 6, pp. 1392-1398 (Nov./Dec. 1992).

Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).

Kadaba, M.P. et al., "Measurement of Lower Extremity Kinematics During Level Walking," *Journal of Orthapedic Research*, pp. 383-392, 1990.

Kadaba, M.P. et al., "Repeatability of Kinematic, Kinetic, and Electromyographic Data in Normal Adult Gait," *Journal of Orthopedic Research*, pp. 849-860, 1989.

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2," Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katic, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. et al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

Khatib, O. et al., "Whole-Body Dynamic Behavior and Control of Human-Like Robots," *International Journal of Humanoid Robotics*, vol. 1, No. 1, pp. 29-43 (2004).

Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).

Kim, J.-H. et al., "Realization of dynamic walking for the humanoid robot platform KHR-1," *Advanced Robotics*, vol. 18, No. 7, pp. 749-768 (2004).

Kirkwood, C.A. et al., "Automatic detection of gait events: a case study using inductive learning techniques," *J. Biomed. Eng.*, vol. 11, pp. 511-516 (Nov. 1989).

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.

Klute, G.K. et al., "Artificial Muscles: Actuators for Lower Limb Prostheses," Abstract in: Proceedings of the $2^{nd}$ Annual Meeting of the VA Rehabilitation Research and Development Service, Washington, D.C., Feb. 20-22, 2000, p. 107.

Klute, G.K. et al., "Artificial Muscles: Actuators for Biorobotic Systems," *The International Journal of Robotics Research*, vol. 21, pp. 295-309 (2002).

Klute, G.K. et al., "Artificial Muscles: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.

Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.

Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.

Klute, G.K. et al., "Mechanical properties of prosthetic limbs: Adapting to the patient," *Journal of Rehabilitation Research and Development*, vol. 38, No. 3, pp. 299-307 (May/Jun. 2001).

Klute, G.K. et al., "Muscle-like Pneumatic Actuators for Below-knee Prostheses," "Actuator 2000: $7^{th}$ International Conference on New Actuators," Bremen, Germany on Jun. 19-21, 2000, pp. 289-292.

Klute, G.K. et al., "Powering Lower Limb Prosthetics with Muscle-like Actuators," Abstract in: Proceedings of the $1^{st}$ Annual Meeting of the VA Rehabilitation Research and Development Service, "Enabling Veterans: Meeting the Challenge of Rehabilitation in the Next Millenium," Washington, D.C., Oct. 1-3, 1998, p. 52.

Klute, G.K. et al., "Variable Stiffness Prosthesis for Transtibial Amputees," 2 pages.

Koganezawa, K. et al., *Biomedical Engineering 1987*, 2.3: Control Aspects of Artificial Leg, pp. 71-85.

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.

Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).

Kuo, A.D., "A Simple Model of Bipedal Walking Predicts the Preferred Speed—Step Length Relationship," *Transactions of the ASME*, vol. 123, pp. 264-269 (Jun. 2001).

(56) References Cited

OTHER PUBLICATIONS

Kuo, A.D., "Energetics of Actively Powered Locomotion Using the Simplest Walking Model," *Journal of Biomechanical Engineering*, vol. 124, pp. 113-120 (Feb. 2002).

Lafortune, M.A., "Three-Dimensional Acceleration of the Tibia During Walking and Running," *J. Biomechanics*, vol. 24, No. 10, pp. 877-886 (1991).

LeBlanc, M.K. et al., "Generation and Transfer of Angular Momentum in the Javelin Throw," American Society of Biomechanics, Presented at the 20th Annual Meeting of the American Society of Biomechanics, Atlanta, Georgia, Oct. 17-19, 1996, 4 pages.

Light, L.H. et al., "Skeletal Transients on Heel Strike in Normal Walking with Different Footwear," J. Biomechanics, vol. 13, pp. 477-480 (1980).

Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.

Lloyd, R. et al., "Kinetic changes associated with load carriage using two rucksack designs," *Ergonomics*, vol. 43, No. 9, pp. 1331-1341 (2000).

Luinge, H.J., *Inertial Sensing of Human Movement*, Twente University Press, Enschede, the Netherlands, 80 pages (Feb. 15, 1973).

Lundberg, A., "Reflex control of stepping," The Norwegian Academy of Science and Letters, The Nansen Memorial Lecture, Oct. 10, 1968, 40 pages.

Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.

Maganaris, C.N., "Force-length characteristics of in vivo human skeletal muscle," *Acta Physiol Scand*, 172: 279-285 (2001).

Maganaris, C.N., "Force-Length Characteristics of the In Vivo Human Gastroenemius Muscle," *Clinical Anatomy*, 16: 215-223 (2003).

Martens, W.L. J., "Exploring the Information Content and Some Applications of Body Mounted Piezo-Resistive Accelerometers," 3 pages.

Maufroy, C. et al., "Towards a general neural controller for quadrupedal locomotion," Neural Networks, 21: 667-681 (2008).

Mayagoitia, R.E. et al., "Accelerometer and rate gyroscope measurement of kinematics: an inexpensive alternative to optical motion analysis systems," *Journal of Biomechanics*, 35: 537-542 (2002).

McFadyen, B.J. et al., "An Integrated Biomechanical Analysis of Normal Stair Ascent and Descent," J. Biomechanics, vol. 21, No. 9, pp. 733-744 (1988).

McGeer, T., "Passive Dynamic Walking," The International Journal of Robotics Research, 9, pp. 62-88 (1990).

McGreer, T., Chapter 4: "Principles of Walking and Running," *Advances in Comparative and Environmental Physiology*, vol. 11, pp. 113-139 (1992).

McIntosh, A.S. et al., "Gait dynamics on an inclined walkway," Journal of Biomechanics, vol. 39, Issue 13, pp. 2491-2502 (2006).

McMahon, T.A. et al., "Groucho Running," pp. 2326-2337 (1987).

McMahon, T.A. et al., "The Mechanics of Running: How Does Stiffness Couple with Speed?" J. Biomechanics, vol. 23, Suppl. 1, pp. 65-78 (1990).

Minassian, K. et al., "Human lumbar cord circuitries can be activated by extrinsic tonic input to generate locomotor-like activity," Human Movement Science, 26: 275-295 (2007).

Mochon, S. et al., "Ballistic Walking," *J. Biomechanics*, vol. 13, pp. 49-57 (1980).

Molen, N.H., "Energy/Speed Relation of Below-Knee Amputees Walking on a Motor-Driven Treadmill," Physiol, 31: 173-185 (1973).

Morris, J.R.W., "Accelerometry—A Technique for the Measurement of Human Body Movements," J. Biomechanics, vol. 6, pp. 729-736 (1973).

Muraoka, T. et al., "Muscle fiber and tendon length changes in the human vastus lateralis during show pedaling," J. Appl. Physiol., 91: 2035-2040 (2001).

Nakagawa, A., "Intelligent Knee Mechanism and the Possibility to Apply the Principle to the Other Joints," paper presented at the Proceedings of the 20th Annual International Conference of the IEEE Engineering in Medicine and Biology Society, 20(5): 2282-2287 (1998).

Neal, R. M. et al., "A View of the EM Algorithm That Justifies Incremental, Sparse, and Other Variants," pp. 1-14.

Ng, S.K. et al., "Fuzzy Model Identification for Classification of Gait Events in Paraplegics," IEEE Transactions on Fuzzy Systems, 5(4) (1997).

Nielsen, D.H. et al., "Comparison of Energy Cost and Gait Efficiency during Ambulation in Below-Knee Ampuees Using Different Prosthetic Feet," *JPO*, 1:24-31, http://www.oandp.org/jpo/library/1989_01_024.asd, Retrieved on: Feb. 7, 2012.

Oda, T. et al. "In Vivo Length-Force Relationships on Muscle Fiber and Muscle Tendon Complex in the Tibialis Anterior Muscle," *International Journal of Sport and Health Sciences*, 3:245-252 (2005).

Ogihara, N., and Yamazaki, N., "Generation of Human Bipedal Locomotion by a Bio-Mimetic Neuro-Musculo-Skeletal Model," *Biol. Cybern.*, 84: 1-11 (2001).

Palmer, M.L., "Sagittal Plane Characterization of Normal Human Ankle Function Across a Range of Walking Gait Speeds," Unpublished master's thesis, Massachusetts Institute of Technology, Massachusetts (2002).

Paluska, D., and Herr, H., "Series Elasticity and Actuator Power Output," paper presented at the Proceedings of the 2006 IEEE International Conference on Robotics and Automation (2006).

Paluska, D., and Herr H., "The Effect of Series Elasticity on Actuator Power and Work Output: Implications for Robotic and Prosthetic Joint Design," Robotics and Autonomous Systems, 54:667-673 (2006).

Pang, M.Y.C. and Yang, J.F., "The Initiation of the Swing Phase in Human Infact Stepping: Importance of Hip Position and Leg Loading," *Journal of Physiology*, 528(2):389-404 (2000).

Dubowsky, S., "Transactions of the ASME," *Journal of Mechanisms, Transmissions, and Automation in Design*, 106(1): 102-107 (1984).

Paul, C., et al., "Development of a Human Neuro-Musculo-Skeletal Model for Investigation of Spinal Cord Injury," *Biol. Cybern.*, 93:153-170 (2005).

Pearson, K., et al., "Assessing Sensory Function in Locomotor Systems Using neurp-mechanical Simulations," *Trends in Neurosciences*, 29(11): 626-631 (2006).

Pearson, K.G., "Generating the Walking Gait: Role of Sensory Feedback," Progress in Brain Research, 143:123-129 (2004).

Perry, J., et al., "Efficiency of Dynamic Elastic Response Prosthetic Feet," *Journal of Rehabilitation Research*, 30(1):137-143 (1993).

Davids, J.R., "Book Reviews" Journal of Pediatric Orthopedics, pp. 815, No date given.

Petrofsky, J.S.., et al., "Feedback Control System for Walking in Man," *Comput. Biol. Med*. 14(2):135-149 (1984).

Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).

Popovic, M., et al., "Angular Momentum Primitives for Human Walking: Biomechanics and Control," paper presented at the Proceedings IEEE/RSJ International Conference on Intelligent Robots and Systems, 1685-1691 (2004).

Popovic, M., et al., "Angular Momentum Regulation During Human Walking: Biomechanics and Control," paper presented at the Proceedings IEEE International Conference on Robotics and Automation, 2405-2411 (2004).

Popovic, M., et al., "Conservation of Angular Momentum During Human Locomotion," *MIT Artificial Intelligence Laboratory*, pp. 231-232 (2002).

(56) References Cited

OTHER PUBLICATIONS

Popovic, D., et al., "Control Aspects of Active Above-Knee Prosthesis," *Int. J. Man-Machine Studies*, 35:751-767 (1991).
Popovic, D. and Sinkjaer, T., "Control of Movement for the Physically Disabled: Control for Rehabilitation Technology," (Springer Publisher) pp. 270-302, No date given.
Popovic, M.R., et al., "Gait Identification and Recognition Sensor," paper presented at the Proceedings of $6^{th}$ Vienna International Workshop on Functional Electrostiumlation (Sep. 1998).
Popovic, M.B. and Herr, H., "Global Motion Control and Support Base Planning," pp. 1-8.
Popovic, M.B. and Herr, H., "Ground Reference Points in Legged Locomotion: Definitions, Biological Trajectories and Control Implications," *Mobile Robots Towards New Applications*, ISBN 3-86611-314-5, pp. 79-104 (2006).
Popovic, M.B., et al., "Zero Spin Angular Momentum Control: Definition and Applicability," pp. 1-16.
Pratt, G.A., "Legged Robots at MIT: What's New Since Raibert." Paper presented at the meeting of the IEEE, Robotics and Automation Magazine (Sep. 2000).
Pratt, G.A., "Low Impedance Walking Robots," *Integ. and Comp. Biol.*, 42: 174-181 (2002).
Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).
Pratt, G.A. and Williamson, M.M., "Series Elastic Actuators." Paper presented at the meeting of the IEEE, pp. 399-406 (1995).
Prochazka, A. and Yakovenko, S., "The Neuromechanical Tuning Hypothesis," *Progress in Brain Research*, 165: 257-267 (2007).
Prochazka, A., et al., "Sensory Control of Locomotion: Reflexes Versus Higher-Level Control," *Sensorimotor Control of Movement and Posture*, pp. 357-367 (2002).
Prochazka, A., et al., "Positive Force Feedback Control of Muscles," *The American Physiological Society*, pp. 3226-3236 (1997).
Raibert, M.H., "Legged Robots that Balance," MIT Press, Cambridge, MA, p. 89 (1985).
Rassier, D.E., et al., "Length Dependence of Active Force Production in Skeletal Muscle," *The American Physiological Society*, pp. 1445-1457 (1999).
Riener, R., et al., "Stair Ascent and Descent at Different Inclinations," *Gait and Posture*, 15: 32-44 (2002).
Rietman, J.S., et al., "Gait Analysis in Prosthetics: Opinions, Ideas and Conclusions," *Prosthetics and Orthotics International*, 26: 50-57 (2002).
Robinson, D.W., "Design and Analysis of Series Elasticity in Closed-Loop Actuator Force Control." Unpublished doctoral dissertation, Massachusetts Institute of Technology (2000).
Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).
Rosen, J., et al., "A Myosignal-Based Powered Exoskeleton System," *IEEE Transaction on Systems, Man, and Cybernetics—Part A: Systems and Humans*, 31(3): 210-222 (2001).
Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).
Rybak, I.A., et al., "Modelling Spinal Circuitry Involved in Locomotor Pattern Generation: Insights from Deletions During Fictive Locomotion," *J. Physiol.*, 577(2): 617-639 (2006).
Rybak, I.A., et al., "Modelling Spinal Circuitry Involved in Locomotor Pattern Generation: Insights from the Effects of Afferent Stimulation," *J. Physiol.*, 577(2): 641-658 (2006).
Sanderson, D.J. and Martin. P.E., "Lower Extremity Kinematic and Kinetic Adaptations in Unilateral Below-Knee Amputees During Walking," *Gait & Posture*, 6(2): 126-136 (1997).
Sanger, T.D., "Human Arm Movements Described by a Low-Dimensional Superposition of Principal Components," *The J. of Neuroscience*, 20(3): 1066-1072 (2000).
Saranli, U., et al., "RHex: A Simple and Highly Mobile Hexapod Robot," *The International Journal of Robotics Research*, pp. 616-631 (2001).
Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).
Schaal, S. and Atkeson, C.G., "Constructive Incremental Learning from Only Local Information," *Neural Computation*, 10(8): 2047-2084 (1998).
Schaal, S., "Is Imitation Learning the Route to Humanoid Robots?", *Trends in Cognitive Sciences*, 3: 233-242 (1999).
Scott, S.H. and Winter, D.A., "Biomechanical Model of the Human Foot: Kinematics and Kinetics During the Stance Phase of Walking," *J. Biomechanics*, 26(9): 1091-1104 (1993).
Sentis, L. and Khatib, O., "Task-Oriented Control of Humanoid Robots Through Prioritization." Paper presented at the IEEE-RAS/RSJ International Conference on Humanoid Robots, pp. 1-16.
Seyfarth, A., et al., "A Movement Criterion for Running," *J. of Biomechanics*, 35: 649-655 (2002).
Seyfarth, A., et al., "Stable Operation of an Elastic Three-Segment Leg," *Biol. Cybern.*, 84: 365-382 (2001).
Seyfarth, A., et al., "Swing-Leg Retraction: A Simple Control Model for Stable Running," *The J. of Experimental Biology*, 206: 2547-2555 (2003).
Giszter et al., "Convergent Force Fields Organized in the Frog's Spinal Cord," The Journal of Neuroscience, Feb. 1993, pp. 467-491.
Sinkjacr, T., et al., "Major role for sensory feedback in soleus EMG activity in the stance phase of walking in man," *Journal of Physiology*, 523.3: 817-827 (2000).
Skinner, H.B., and Effeney, D.J., "Gait Analysis in Amputees," *American Journal of Physical Medicine*, 64(2): 82-89 (1985).
Smidt, G.L., et al., "An Automated Accelerometry System for Gait Analysis," *J. Biomechanics*, 10: 367-375 (1977).
Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5.
Stepien, J., et al., "Activity Levels Among Lower-Limb Amputees: Self-Report Versus Step Activity Monitor," *Arch. Phys. Med. Rehabil.*, 88: 896-900 (2007).
Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).
Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).
Sup, F., et al., "Design and Control of a Powered Transfemoral Prosthesis," *The International Journal of Robotics Research*, 27(2): 263-273 (2008).
Taga, G., "A model of the neuro-musculo-skeletal system for human locomotion," *Biol. Cybern.*, 73: 97-111 (1995).
Takayuki, F., et al., "Biped Locomotion using Multiple Link Virtual Inverted Pendulum Model," *T.IEE Japan*, 120-C (2): 208-214 (2000).
Thoroughman, K., and Shadmehr, R., "Learning of action through adaptive combination of motor primitives," *Nature*, 407: 742-747(2000).
Tomović, R., and McHee, R.B., "A Finite State Approach to the Synthesis of Bioengineering Control Systems," *IEEE Transactions on Human Factors in Electronics*, 7(2): 65-69 (1966).
Tong, K., and Granat, M., "A practical gait analysis system using gyroscopes," *Medical Engineering & Physics*, 21: 87-94 (1999).
Türker, K., "Electromyography: Some Methodological Problems and Issues," *Phys. Ther.*, 73: 698-710 (1993).
Van den Bogert, A. J., et al., "A Method for Inverse Dynamic Analysis Using Accelerometry," *J. Biochemechanics*, 29(7): 949-954 (1996).

(56) References Cited

OTHER PUBLICATIONS

Van den Bogert, A. J., "Exotendons for Assistance of Human Locomotion," Biomedical Engineering OnLine, BioMed Central, 2(17):1-8 (2003).

Veltink, P.H., et al., "The Feasibility of Posture and Movement Detection by Accelerometry," paper presented at the IEEE meeting (1993).

Vukobratovic, M., Juricic, D., "Contribution to the Synthesis of Biped Gait," paper presented at the IEEE Transactions on Bio-Medical Engineering, BME-16(1) (Jan. 1969).

Vukobratovic, M., and Stepanenko, J., :Mathematical Models of General Anthropomorphic Systems, Mathematical Biosciences, 17: 191-242 (1973).

Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).

Waters, R.L., et al., "Energy Cost of Walking of Amputees: The Influence of Level of Amputation," *The Journal of Bone and Joint Surgery*, 58A(1): 42-46 (1976).

Wilkenfeld, A., and Herr, H., "An Auto-Adaptive External Knee Prosthesis," MIT Lab., No date given.

Wilkenfeld, A., "Biologically Inspired Autoadaptive Control of a Knee Prosthesis," unpublished doctoral dissertation, Massachusetts Institute of Technology, Cambridge, MA (2000).

Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).

Willemsen, A.Th.M., et al., "Real-Time Gait Assessment Utilizing a New Way of Accelerometry," *J. Biomechanics*, 23(8):859-863 (1990).

Williams, B.C., et al., "Mode Estimation of Model-Based Programs: Monitoring Systems with Complex Behavior," paper submitted to Massachusetts Institute of Technology, Cambridge, MA, No date given.

Williamson, M.M., "Series Elastic Actuators," A.I. Technical Report submitted to Massachusetts Institute of Technology, Cambridge, Massachusetts (Jan. 1995).

Winter, D.A., and Sienko, S.E., "Biomechanics of Below-Knee Amputee Gait," *J. Biomechanics*, 21(5):361-367 (1988).

Winter, D.A., "Energy Generation and Absorption at the Ankle and Knee during Fast, Natural, and Slow Cadences," *Clinical Orthopedics and Related Research*, 175: 147-154 (1983).

Winter, D.A., and Robertson, D.G.E., "Joint Torque and Energy Patterns in Normal Gait," Biol. Cybernetics, 29:137-142 (1978).

Wisse, M., "Essentials of Dynamic Walking: Analysis and Design of Two-legged Robots," No date given.

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3): 193-200 (1996).

Yakovenko, S., et al., "Contribution of Stretch Reflexes to Locomotor Control: A Modeling Study," *Biol. Cybern.*, 90: 146-155 (2004).

Yun, X., "Dynamic State Feedback Control of Constrained Robot Manipulators." Paper presented at the Proceedings of the 27th Conference on Decision and Control, Austin, TX (Dec. 1988).

Zlatnik, D., et al., "Finite-State Control of a Trans-Femoral (TF) Prosthesis," *IEEE Transactions on Control Systems Technology*, 10(3): 408-420 (2002).

Au, S.K. et al., "Initial Experimental Study on Dynamic Interaction Between an Amputee and a Powered Ankle-Foot Prostheses," Harvard—MIT Division of Health Sciences and Technology, MIT, Cambridge, MA. (2006).

Chang, M.D., L., et al. "Ischemic Colitis and Complications of Constipation Associated With the Use of Alosetron Under a Risk Management Plan: Clinical Characteristics, Outcomes, and Incidences," *Am J Gastroenterol*, 105(4):866-875 (2010).

Colborne, G.R., et al., "Analysis of mechanical and metabolic factors in the gait of congenital below knee amputees," *Am. J. Phys. Med. Rehabil.*, vol. 92, pp. 272-278, Oct. 1992.

Collins, S.H., et al., "A Bipedal Walking Robot with Efficient and Human-Like Gait," 2005 IEEE, Int'l Conference on Robotics and Automation, Barcelona, Spain, pp. 1983-1988, (Apr. 2005).

Drake, C., "Ankle & Foot Splints or Orthoses (AFOs)," HemiHelp Information Sheet, pp. 1-6, last revision Dec. 2011.

Eilenberg, et al., "Control of a Powered Ankle-Foot Prosthesis Based on a Neuromuscular Model, *IEEE Transactions on Neural Systems & Rehabilitation Eng.*", vol. 18(2):164-173 (2010).

Hanafusa, et al., "A Robot Hand with Elastic Fingers and Its Application to Assembly Process," pp. 337-359, Robot Motion, Brady, et al., MIT Press, Cambridge, MA 1982.

Holgate, M.A., et al., "The SPARKy (Spring Ankle with Regenerative Kinetics) Project: Choosing a DC Motor Based Actuation Method," Proceedings of the 2nd Biennial IEEE-EMBS International Conf. on Biomedical Robotics and Biomechatronics, Scottsdale, AZ, pp. 163-168, Oct. 19-22, 2008.

International Search Report for PCT/US2010/022783, "Model-Based Neuromechanical Controller for a Robotic Leg", dated May 4, 2010.

Pasch, K.A., et al., "On the drive systems for high performance machines," *AMSE J. Mechanisms, Transmissions, and Automation in Design* 106(1):102-108 (Mar. 1984).

Supplementary European Search Report Application No. 10736533.0, dated Aug. 16, 2013.

Supplementary European Search Report Application No. 10736550.0, dated Aug. 1, 2013.

Aeyels, B., et al., "An EMG-Based Finite State Approach for a Microcomputer-Controlled Above-Knee Prosthesis," Engineering in Medicine and Biology Society 1995, pp. 1315-1316 (1997).

Peeraer, L., et al., "Development of EMG-based mode and intent recognition algorithms for a computer-controlled above-knee prosthesis," J. Biomed. Eng., 12: 178-182 (1990).

Saxena, S. C., and Mukhopadhyay, P., "E.M.G. operated electronic artificial-leg controller," Med. & Biol. Eng. & Comput., 15: 553-557 (1977).

Notice of Allowance from U.S. Appl. No. 13/970,094, entitled, "Powered Ankle-Foot Prosthesis," dated Jul. 12, 2018.

\* cited by examiner

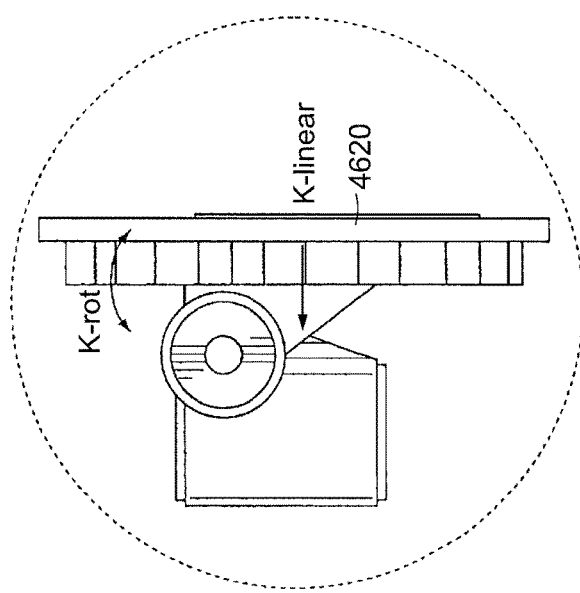
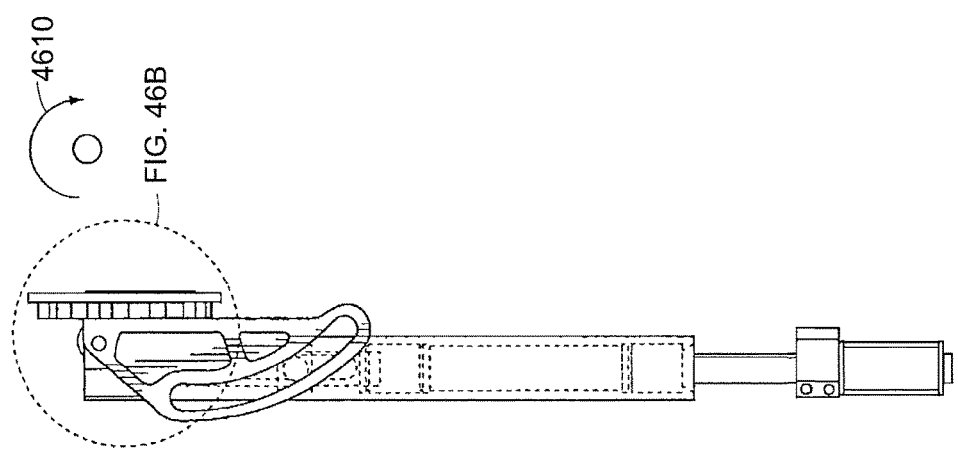
FIG. 46B
FIG. 46A

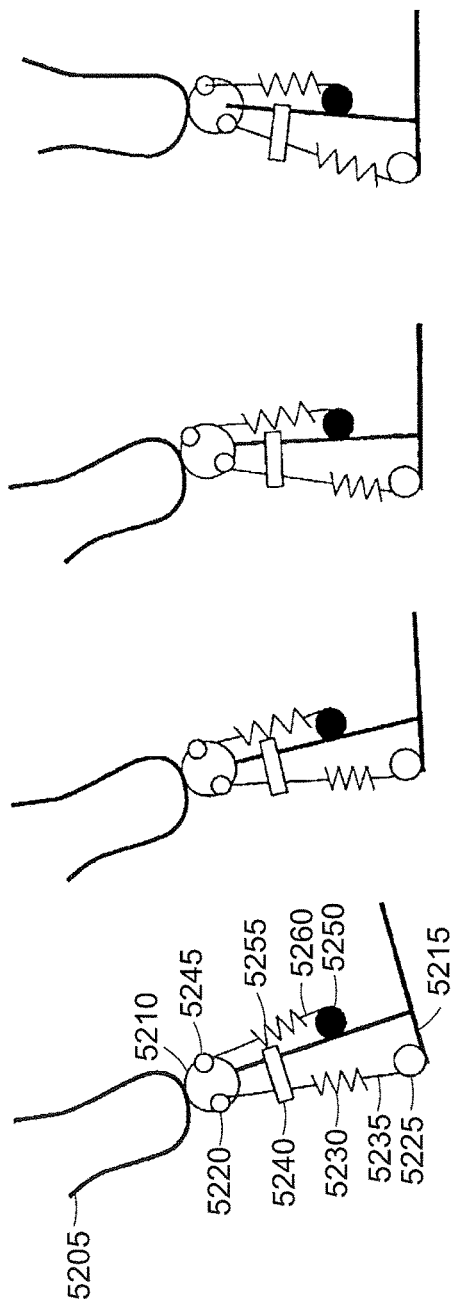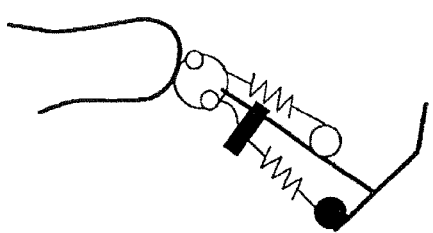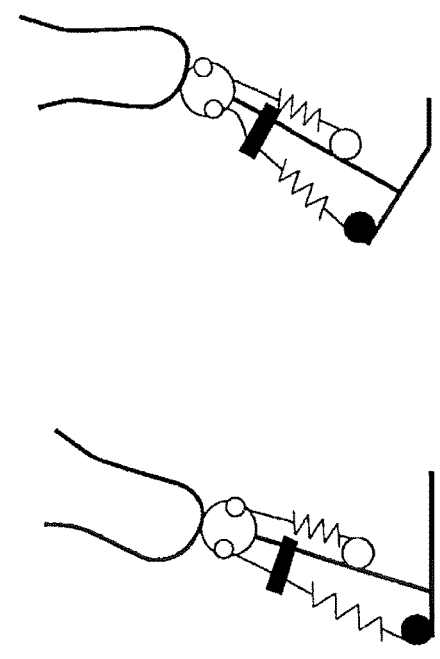
FIG. 52A FIG. 52B FIG. 52C FIG. 52D FIG. 52E FIG. 52F FIG. 52G

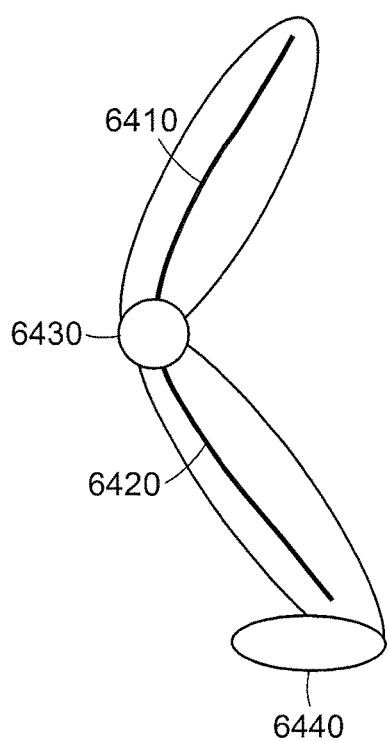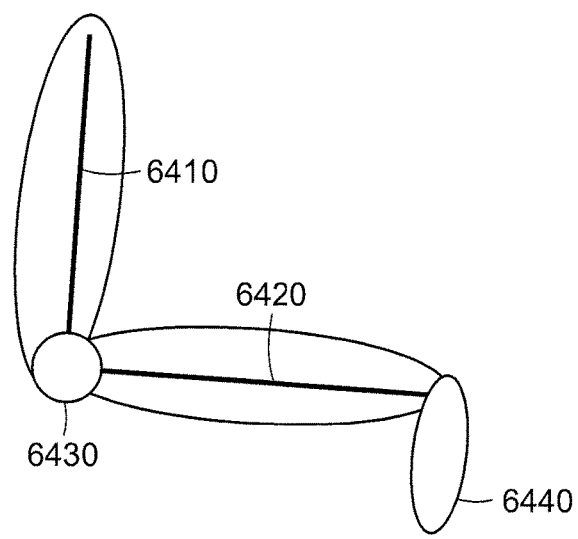
FIG. 64A
FIG. 64B

EXOSKELETONS FOR RUNNING AND WALKING

CROSS REFERENCE TO RELATED APPLICATIONS

This application is a continuation of U.S. patent application Ser. No. 11/600,291, filed Nov. 15, 2006, now abandoned, which claims the benefit of U.S. Provisional Patent Application Ser. No. 60/736,929, filed Nov. 15, 2005.

This application is also a continuation in part of U.S. patent application Ser. No. 11/395,448, filed on Mar. 31, 2006. Application Ser. No. 11/395,448 claims the benefit of the filing date of U.S. Provisional Patent Application Ser. No. 60/666,876, filed on Mar. 31, 2005, and the benefit of the filing date of U.S. Provisional Patent Application Ser. No. 60/704,517, filed on Aug. 1, 2005.

This application is also a continuation in part of U.S. patent application Ser. No. 11/499,853, filed on Aug. 4, 2006. Application Ser. No. 11/499,853 claims the benefit of the filing date of U.S. Provisional Patent Application Ser. No. 60/705,651, filed on Aug. 4, 2005.

This application is also a continuation in part of U.S. patent application Ser. No. 11/495,140, filed on Jul. 29, 2006. Application Ser. No. 11/495,140 claims the benefit of the filing date of U.S. Provisional Patent Application Ser. No. 60/704,517, filed on Aug. 1, 2005 and was also a continuation in part of the above-noted application Ser. No. 11/395,448.

This application claims the benefit of the filing date of each of the foregoing patent applications and incorporates the disclosure of each of the foregoing applications herein by reference.

STATEMENT REGARDING FEDERALLY SPONSORED RESEARCH OR DEVELOPMENT

This invention was made with government support under grant number NBCHC040122 awarded by the Department of the Interior. The government has certain rights in this invention.

FIELD OF THE TECHNOLOGY

This invention relates to load bearing exoskeletal systems for running and walking.

BACKGROUND

A leg exoskeleton could benefit people who engage in load-carrying by increasing load capacity, lessening the likelihood of injury, improving efficiency, and reducing the perceived level of difficulty. Lightweight, efficient exoskeletons could also be used to lower the metabolic cost of walking and running. By analyzing biomechanical data, design principles for efficient actuation strategies can be extracted. The exoskeleton must have a structure for supporting the weight of a payload or wearer. The system must also be capable of varying its position and impedance in a comparable manner to that of a normal, healthy biological limb and applying the appropriate torque and power at the joints to assist in forward locomotion.

Exoskeletons have been developed that amplify the strength of the wearer, apply assistive torques to the wearer's joints, and support a payload being carried by the wearer. General Electric (1968) developed and tested a prototype man-amplifier, a master-slave system called the Hardiman. It was a set of overlapping exoskeletons worn by the human operator. An outer exoskeleton followed the motions of the inner exoskeleton which followed the motions of the human operator. Difficulties in human sensing, stability of the servomechanisms, safety, power requirements and system complexity kept it from walking.

The Berkeley Lower Extremity Exoskeleton is described in the paper by Chu, A., Kazerooni, H. and Zoss, A., 'On the Biomimetic Design of the Berkeley Lower Extremity Exoskeleton (BLEEX)', Proceedings of the 2005 IEEE International Conference on Robotics and Automation, Barcelona, Spain, pp. 4356-4363 (April, 2005). This lower extremity exoskeleton is attached at the human foot and at the back. The hip, knee, and ankle joints are powered in the sagital plane with linear hydraulic actuators. The system is powered with an internal combustion engine that is also supported by the exoskeleton. Sarcos has developed a similar exoskeleton with rotary hydraulics at the joints. Both systems sense the intent of the wearer and the robotic legs walk so as to track the human legs so the wearer does not 'feel' the exoskeleton.

Liu, X., Low, K. H., Yu, H. Y., (2004) 'Development of a Lower Extremity Exoskeleton for Human performance Enhancement', IEEE Conf. on Intelligent Robots and Systems, Sendai, Japan, describes initial prototypes and experiments of an exoskeleton to support a payload and are currently developing a full working prototype.

Vukobratovi, M., Borovac, B., Surla, D., Stoki, D. (1990), Biped Locomotion: Dynamics, Stability, Control, and Application, Springer-Verlag, Berlin, pp. 321-330, describes several exoskeletons to aid walking for paraplegics. Pre-defined trajectories were commanded by the devices and they had limited success in assisting subjects to walk. The devices were greatly limited by material, actuation, and battery technology available at that time. Prof. Sankai from University of Tsukuba in Japan has developed an exoskeleton power assist system to aid people with a gait disorder. This system includes sensors for the joint angles, myoelectric signals of the muscles and floor sensors etc. in order to obtain the condition of the HAL and the operator.

Pratt, J., Krupp, B., Morse, C., Collins, S., (2004) "The RoboKnee: An Exoskeleton for Enhancing Strength and Endurance During Walking", IEEE Conf. on Robotics and Automation, New Orleans, describes a powered, wearable device called the RoboWalker. The objective for this device was to augment or replace muscular function about the human knee by powering the knee joint using series elastic actuators.

Several exoskeleton design approaches have employed hydraulic actuators to power hip, knee, and ankle joints in the sagittal plane. Such an exoskeleton design demands a great deal of power, requiring a heavy power supply to achieve system autonomy. For example, the Bleex, developed at the University of California, Berkeley (Chu et al 2005), consumes approximately 2.27 kW of hydraulic power, 220 Watts of electrical power, and has a total system weight of 100 lbs. This approach leads to a noisy device that has a very low payload to system weight ratio. Further, this type of exoskeleton is heavy and, if failure were to occur, could significantly harm the wearer.

SUMMARY

The following summary provides a simplified introduction to some aspects of the invention as a prelude to the more detailed description that is presented later, but is not intended to define nor delineate the scope of the invention.

The detailed description that follows presents two exoskeleton embodiments of the present invention. In a first implementation, the exoskeleton assists the human user by transferring backpack payload mass to the ground. In a second, the exoskeleton carries the weight of the human. For both exoskeleton designs, a parallel exoskeleton structure is the fundamental architecture to transfer the backpack or human load forces to the ground in walking, running, or jumping.

For the backpack load-carrying exoskeleton for walking, the system interfaces to the human by means of shoulder straps, a hip harness, thigh cuffs, and a shoe attachment. Natural walking kinematics are preserved by collocating the exoskeleton hip, knee, and ankle joints to their biological counterparts. A cam mechanism is implemented at the hip joint to project the exoskeleton hip center near the biological hip center. The cam mechanism corrects for discrepancies between the exoskeleton and biological leg lengths during abduction and adduction. Passive spring elements are implemented at the hip and ankle and a variable damper is implemented at the knee. A non-conservative actuator can add to the hip flexion spring output at the hip, in order to add significant positive power during walking. Control systems are proposed to control the exoskeleton as a function of gait cycle, both for knee variable-dampers and hip motor components.

For the human-carrying exoskeleton for running and jumping, a parallel leaf spring architecture is disclosed that stores energy during jumping and running to efficiently transfer the weight of the wearer to the ground. Simple force or contact sensing may be employed to activate a clutch or variable damper at the knee. To activate the exoskeleton knees passively, a weight activated knee unit may be used wherein the knee automatically locks upon knee compression loading and unlocks when compression forces are no longer borne by the knee unit. Additional elements may be included in the leg design, including a motor in parallel with the leg spring that stores additional energy into the leg spring to augment leg extension in jumping or stair/hill ascent.

The parallel spring and variable damping architectures presented here offer a number of advantages over other devices. Having the exoskeleton architecture in parallel with the human leg allows the stability of the wearer to be maintained. Springs in series with the human raise the center of mass of the wearer and thus destabilize the wearer. Springs in parallel can be disengaged to allow the human leg to swing freely in the swing phase. Also, by allowing the wearer's foot to remain in contact with the ground, overall stability of the wearer is maintained.

BRIEF DESCRIPTION OF THE DRAWINGS

In the detailed description which follows, frequent reference will be made to the attached drawings, in which:

FIGS. 46A and 46B illustrate how the abduction spring is compressed during the stance phase of walking;

FIGS. 52A-G are show the operation of a mechanism for transferring energy from the hip and knee mechanical work to the ankle work;

FIGS. 64A-B depict the motion of the knee joint clutch and the leg springs for an exoskeleton leaf spring mechanism;

DETAILED DESCRIPTION

Biomechanics of Walking and Running. In this section, the biomechanics of human walking and running are examined. In later sections, these biomechanics will motivate the design of the exoskeleton system described herein.

Walking

Figure 1:
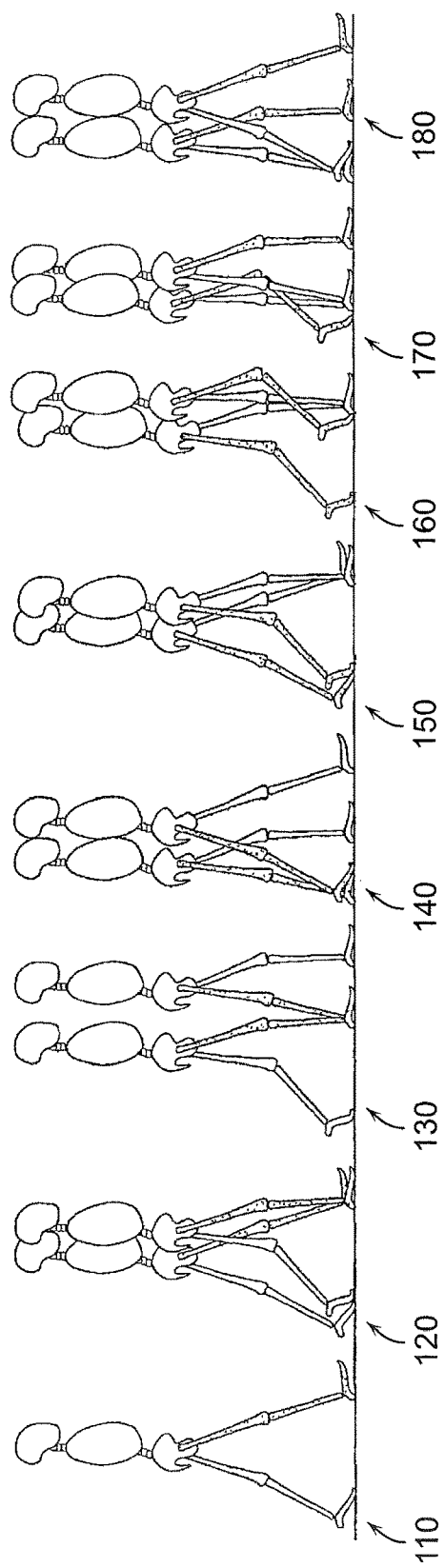
FIG. 1 illustrates the eight phases of the walking cycle from heel strike to heel strike on the same foot.

Walking consists of two phases, a stance phase and a swing phase. During the early stance phase, the muscles at the hip, knee and ankle generally act to decelerate and stabilize the body. At the end of stance, the ankle undergoes powered plantar flexion where it provides the energy to power the body forward and upwards. Additionally, at the start of the swing phase, the hip gives a burst of energy to raise the lower leg from the ground surface. FIG. 1 outlines eight phases of the walking cycle: initial contact (110), loading response (120); mid-stance (130); terminal stance (140); pre-swing (150); initial swing (160); mid-swing (170); and terminal swing (180).

The kinetic energy and gravitational potential energy of the center of mass are approximately 180 degrees out of phase in walking. At mid-stance in walking, the gravitational potential energy is at its maximum and the kinetic energy is at its minimum. Because these energies are approximately 180 degrees out of phase with each other and their fluctuations are similar in magnitude, substantial pendulum-like exchange occurs in walking. In human walking, as much as 60-70% of the mechanical energy required to lift and accelerate the center of mass is conserved by this energy transfer mechanism. Mechanical energy savings are maximized at moderate walking speeds, and fall toward zero at very low and very high walking speeds.

Figure 2:
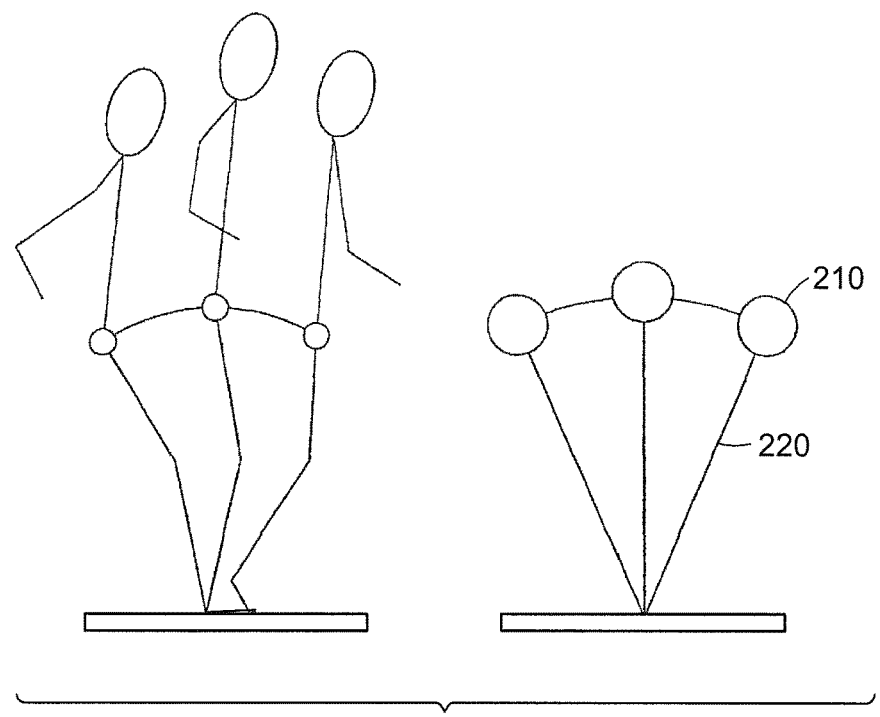
FIG. 2 illustrates the inverted pendulum model of human walking.
Figure 3:
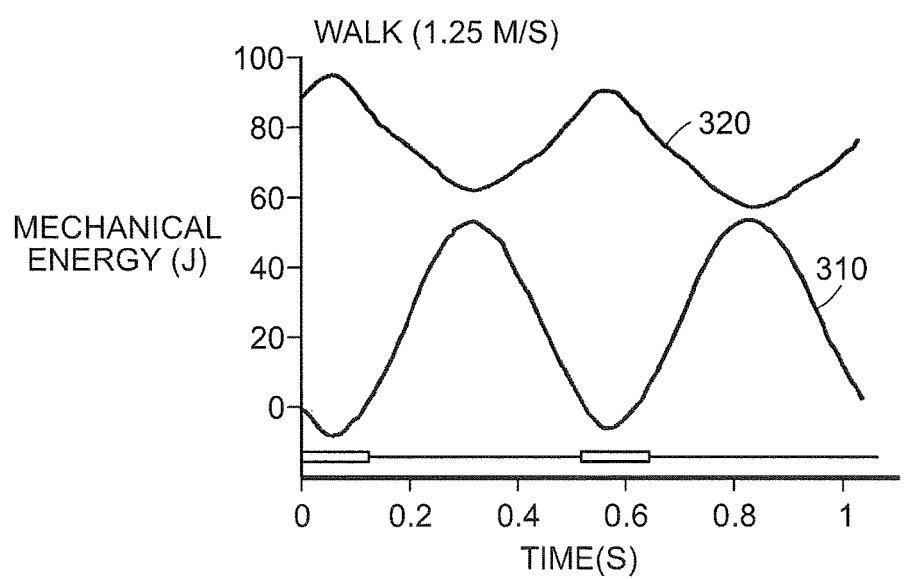
FIG. 3 is a graph depicting how kinetic and potential energy are exchanged during walking.

FIG. 2 illustrates the inverted pendulum model of human walking, showing mass 210 and leg 220, and FIG. 3 is a graph showing the manner in which gravitational potential energy 310 and kinetic energy 320 are exchanged during walking.

Metabolic Studies on External Forces Applied During Walking

Figure 4:
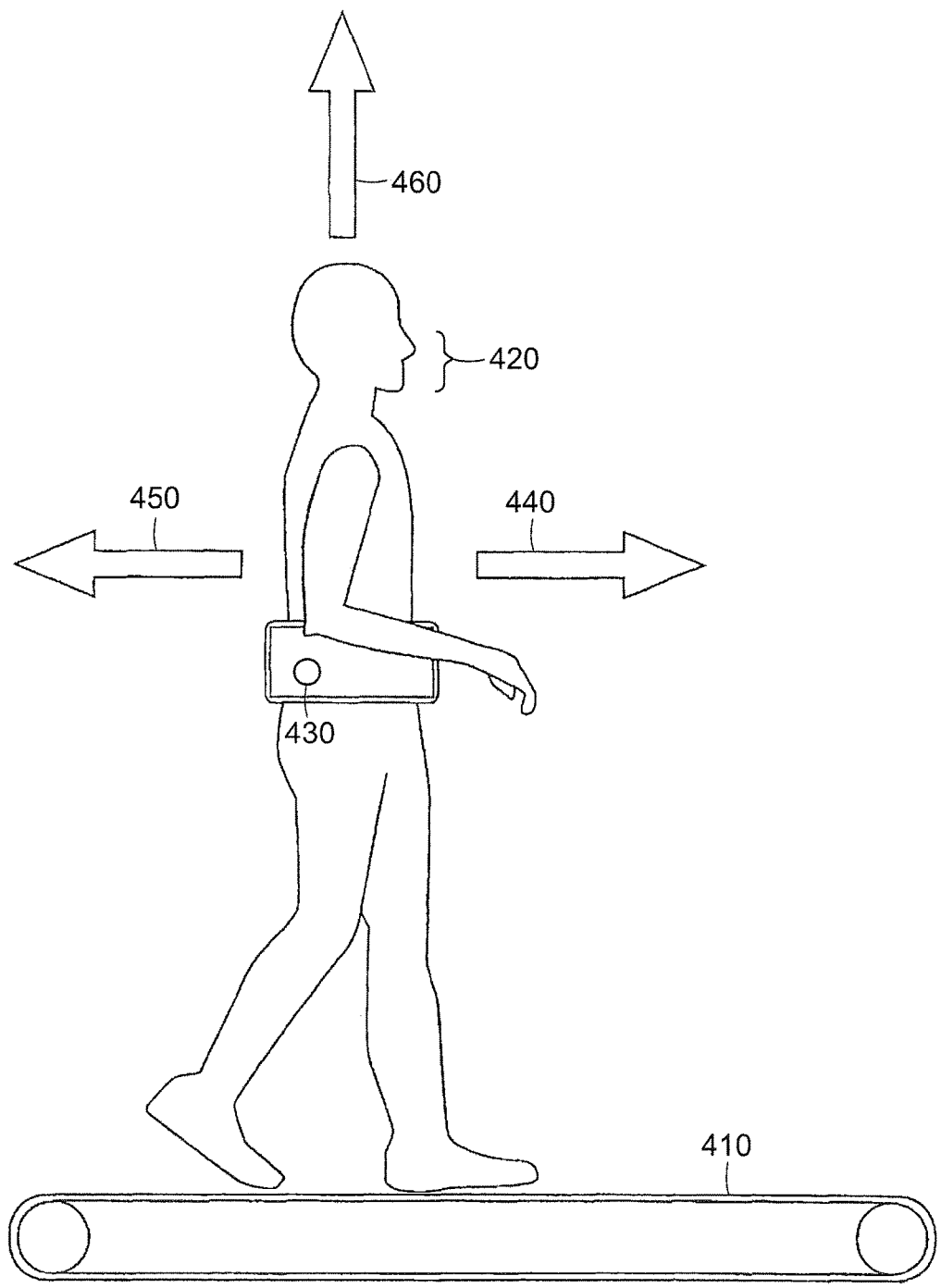
FIG. 4 summarizes the effect of external forces on human walking.

Walking metabolism is set by muscles that act to perform work on the center of mass, swing the legs relative to the center of mass, and support the body weight. A number of researchers have performed experiments on subjects while walking where they apply external loads in the vertical and horizontal direction in order to examine the effect on metabolic rate and muscle activity. The results are summarized in FIG. 4. Shown in FIG. 4 are treadmill 410, VO$_2$ monitor 420, additional mass 430 (10% BM addition; 15% increase [Griffin et al., 2003]), forward assist force 440 (10% BW assist; 47% reduction [Gottschall & Kram, 2003]), drag force 450 (10% BW impeding; 150% increasen [Gottschall & Kram, 2003]), and unweighting force 460 (50% antigravity; 25% reduction [Farley & McMahon, 1992]).

Motivation for a Semi-Active Approach

Evidence from biology and passive walkers suggests that legged locomotion can be very energy efficient. The exchange between potential and kinetic energy suggests that walking may be approximated as a passive mechanical process. Passive walkers reinforce this fact. In such a device, a human-like pair of legs settles into a natural gait pattern generated by the interaction of gravity and inertia. Although a purely passive walker requires a modest incline to power its movements, researchers have enabled robots to walk on level ground by adding just a small amount of energy solely at the hip or the ankle joint. See Wisse, Martijn, Essentails of Dynamic Walking, Analysis and Design of two-legged robots, Phd Thesis (2004), Technical University of Delft. Recent evidence suggests that elastic energy storage is also critical for efficient bipedal ambulation. Palmer, M. L., (2002) 'Sagital Plane Characterization of Normal Human Ankle Function Across a Range of Walking Gait Speeds' MS Thesis, MIT, showed that by characterizing the human ankle during the stance phase of walking in terms of simple mechanical spring elements, sagittal plane dynamics of a normal ankle can be reproduced at least at slow to moderate walking speeds. Further, van den Bogert, van den Bogert, A. J. (2003), 'Exotendons for assistance of human locomotion'. Biomedical Engineering Online, 2:17, showed in numerical simulation that an exoskeleton using passive elastic devices can substantially reduce muscle force and metabolic energy in walking.

Muscle Activity in Gait

Figure 5:
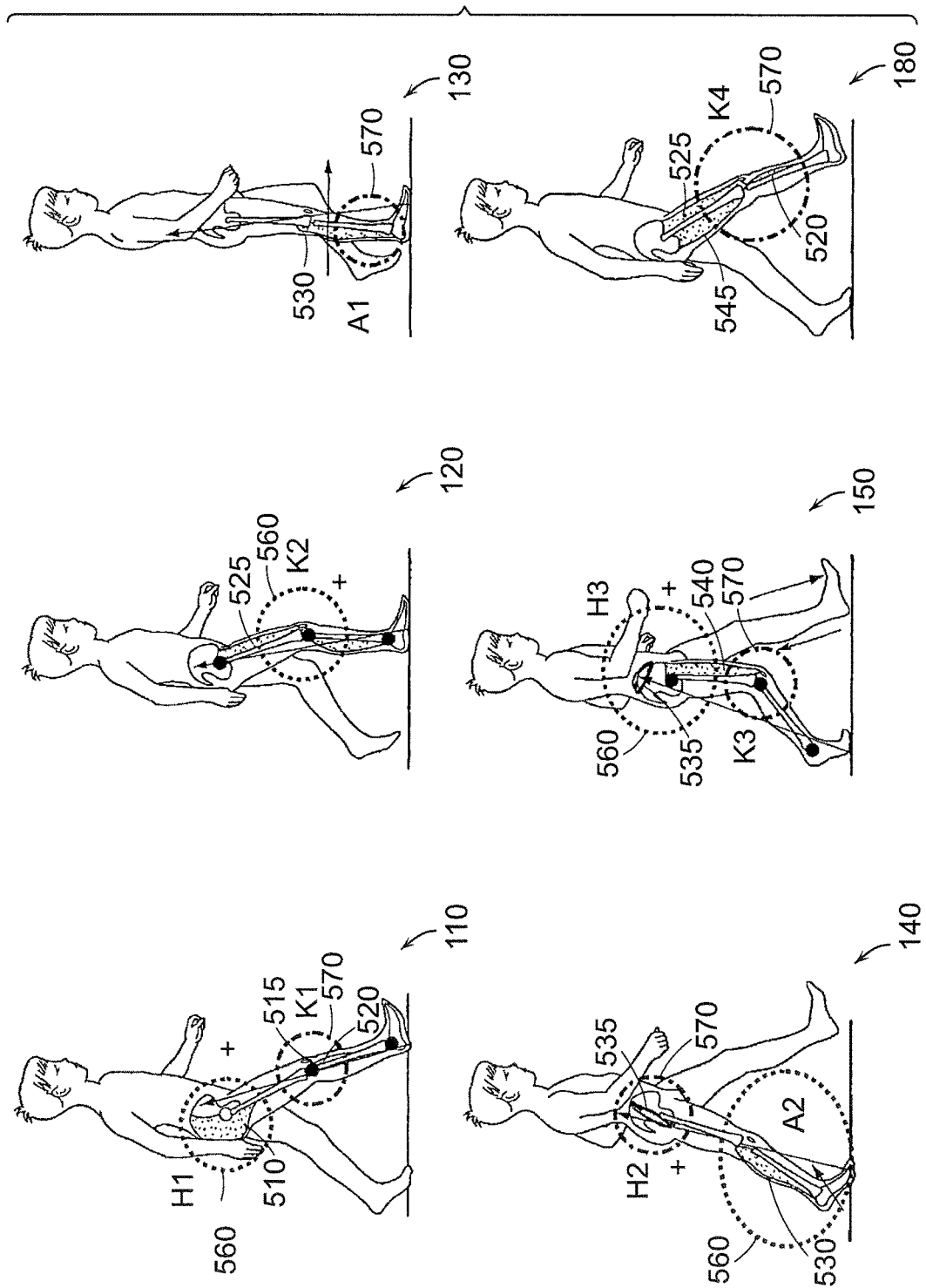
FIG. 5 illustrates the regions of positive and negative work during walking.

FIG. 5 illustrates the significant regions of positive and negative power during the gait cycle. Specifications for actuation components as well as control strategies are extracted from angle, torque and power data at the human hip, knee and ankle joints in the sagittal plane. Muscle groups highlighted in FIG. 5 include Gluteus maximus 510, posterior capsule 515, Tibalis anterior 520, Quadriceps femoris 525, Triceps surae 530, Iliopsoas 535, Rectus femoris 540, and Hamstrings 545. The dotted areas represent regions of positive 560 and negative 570 power exertion.

Many muscles responsible for walking contract isometrically to allow maintenance of upright posture against gravity or transfer or storage from one limb segment to another. Brief bursts of more energy expensive shortening contraction of muscle are added when needed to provide power for forward motion. Positive work is performed when a muscle is concentrically contracting. Negative work is said to be performed when a muscle is eccentrically contracting (elongating while active). Much muscle activity in walking is isometric or eccentric. Negative work allows the limbs to absorb energy while resisting the pull of gravity yet remain metabolically efficient. Positive work of muscles during walking allows acceleration of limbs and powers such activities as push off and extension of the hip after foot strike.

Joint Sagittal Plane Angles, Torques, and Powers

Human walking data were used in order to specify the design requirements for actuation at the exoskeleton joints. A number of assumptions were made in the application of the human biomechanical data to exoskeleton design. The first is that the exoskeleton carries its own weight, power supply and payload. The second assumption is that joint torques and joint powers scale linearly with mass. This second assumptions seems reasonable given that increases in vertical ground reaction force have been found to be proportional to increases in the load being carried as described by Lloyd R., & Cooke C. B. (2000) 'Kinetic changes associated with load carriage using two rucksack designs' Ergonomics 43(9), 1331-1341. The third assumption is that the exoskeleton will not greatly affect the gait of the wearer. This is important because changes in gait have been shown to increase the physiological energy expended during locomotion as described by McMahon, T. A., Valiant, G., & Frederick, E. C. (1987). Groucho Running, Journal of Applied Physiology, 62(6) 2326-2337.

Hip Kinematics and Kinetics

Figure 6:
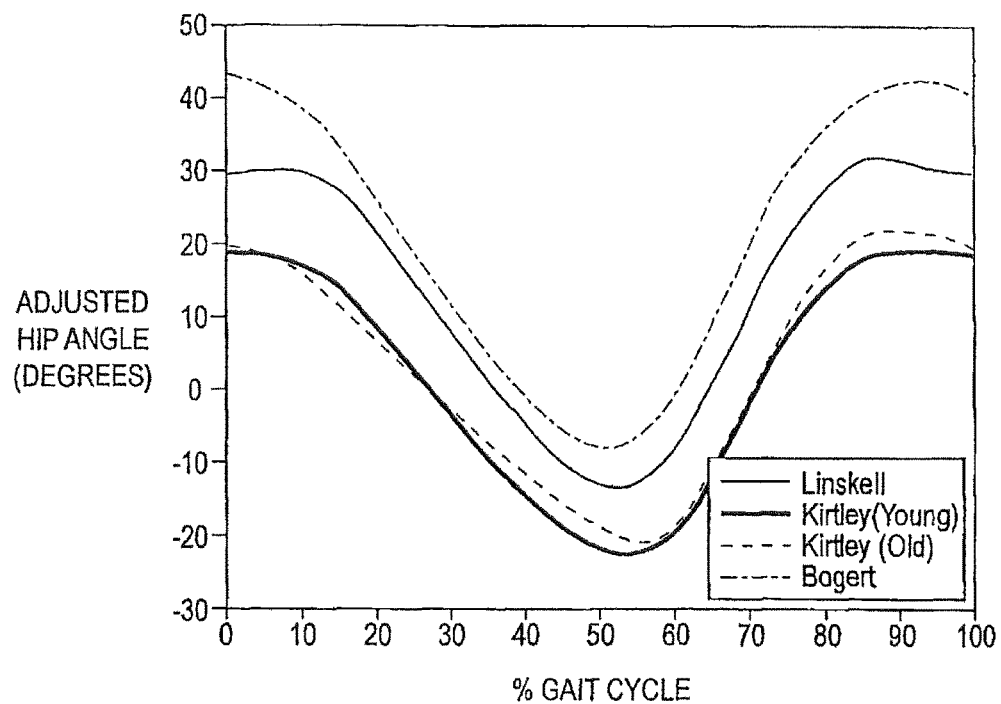
FIG. 6 is a graph showing how hip angle varies during the walking cycle.
Figure 7:
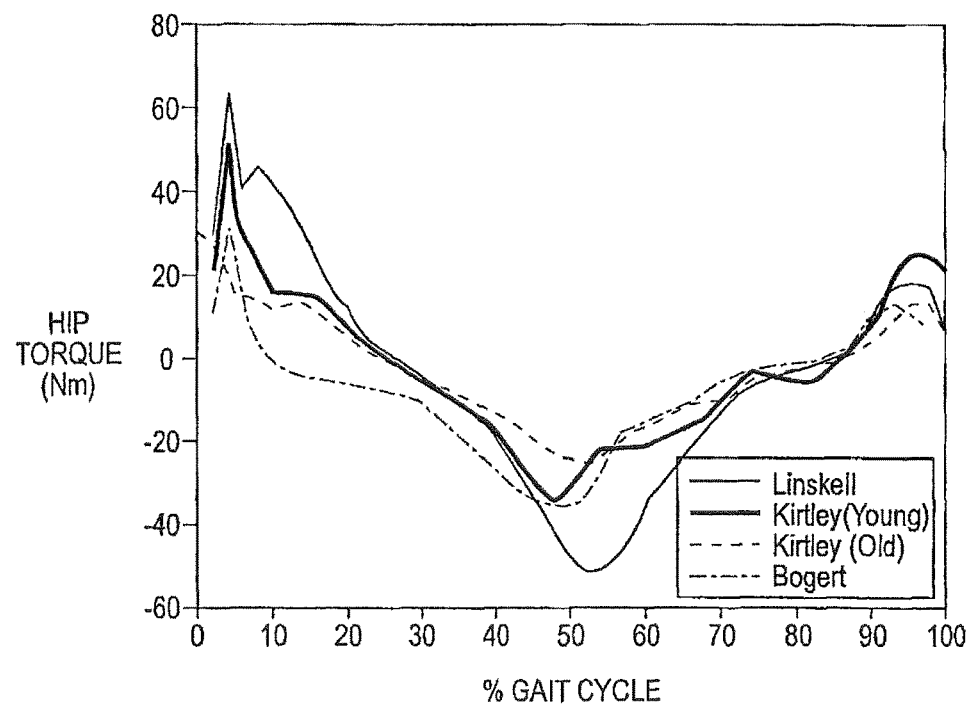
FIG. 7 is a graph showing how hip torque varies during the walking cycle.

FIGS. 6 and 7 graph hip angle and torque scaled for a 60 kg. person. During normal walking the human hip joint follows an approximate sinusoidal pattern with the thigh flexed forward on heel strike and then the hip moves through extension during stance as the body is pivoted over the stance leg in a pendulum-like motion. Positive power is required on heel-strike to raise the center of mass of the human over the stance leg. A peak negative hip torque of approximately −60 Nm is experienced in late stance hip extension just before the leg enters the swing phase. A maximum positive torque of about 50 Nm occurs during the swing phase as the hip muscles provide energy to swing the leg forward. This action is sometimes referred to as "pull off," and is the muscular system's second largest contribution of propulsive power during the gait cycle.

Figure 8:
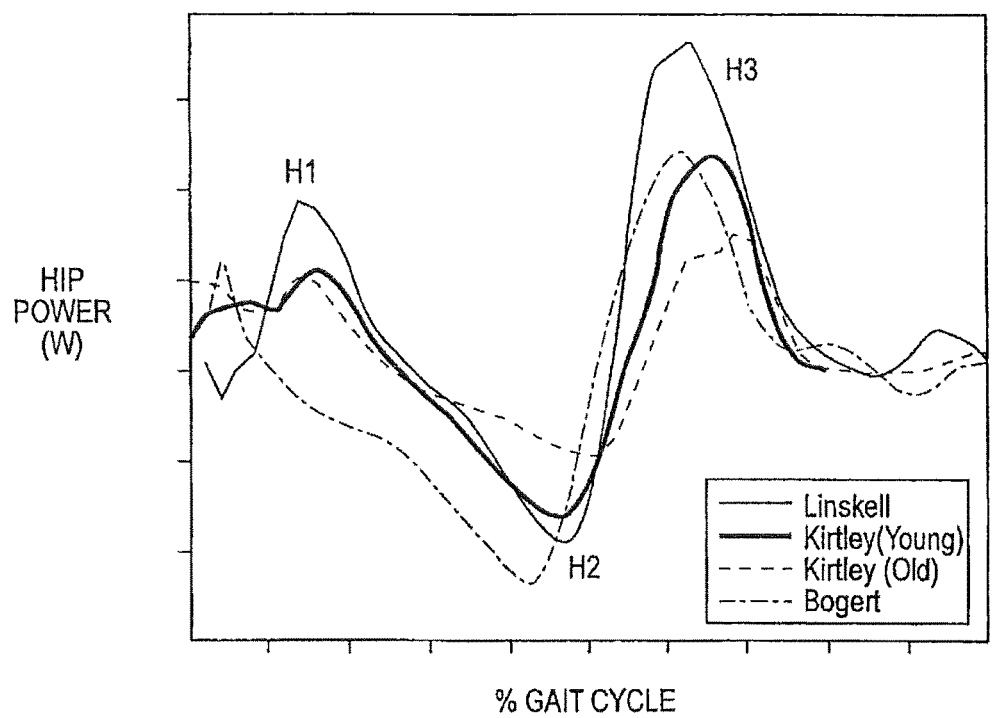
FIG. 8 is graph showing how hip power varies during the walking cycle.
Figure 9:
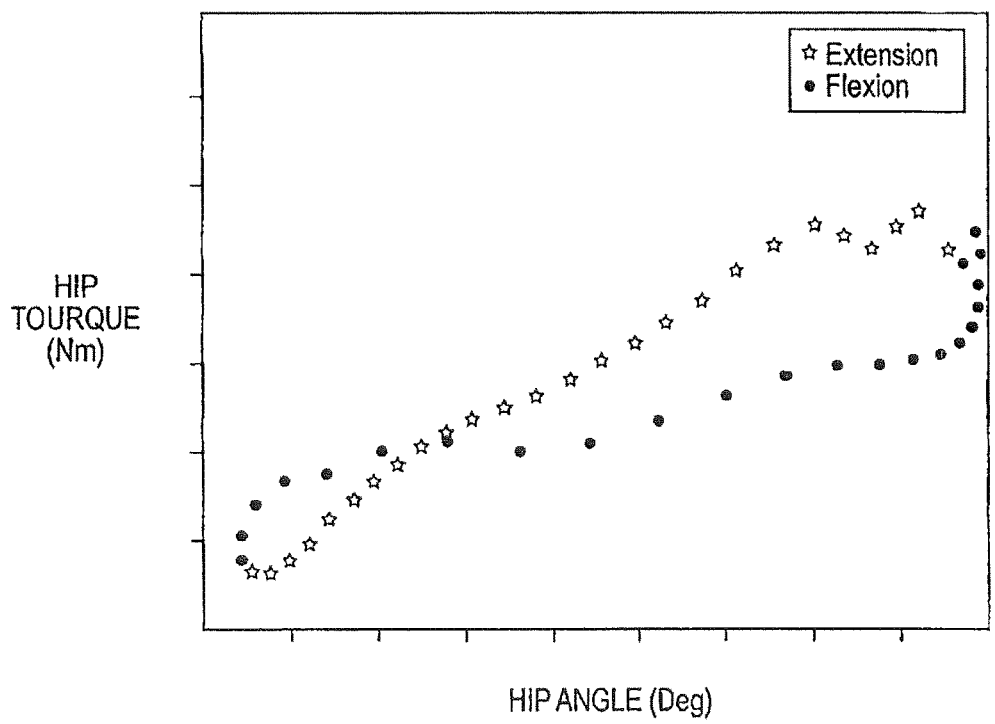
FIG. 9 is a graph showing the relationship between hip torque and hip angle.

The power profile at the hip as a function of gait cycle is shown in FIGS. 8 and 9. H1 is a small region of positive power, not always present, which corresponds to concentric hip extensor activity during loading response, H2 is a region of negative power, corresponding to eccentric hip flexor activity during mid-stance and H3 is a region of positive power, corresponding to concentric activity in the hip flexors during pre-swing and initial swing. Hip torque versus angle is shown on the left plot for a walking speed of 0.8 m/s.

Hip abductors move from eccentric to isometric to concentric activity, elevating the pelvis in preparation for swing. Following this action, there continues to be eccentric hip flexor activity at the hip. During mid-stance the center of gravity of the body has reached its highest point and is carried forward by momentum. Eccentric hip flexor activity resists the body during this falling period. The hip contributes to propulsion as it shifts from eccentric to concentric activity which will advance the extremity into the swing phase by lifting the leg from the ground surface and then swinging it forward. This region is the muscular system's second largest contribution of propulsive power during the gait cycle.

The hip joint is the preferred location for a non-conservative actuator as proximal mass is less expensive metabolically in walking than distal mass. An actuator could assist in adding power in the H1 and H3 regions. From FIGS. 8 and 9, it can also be seen that a spring placed at the hip joint could absorb energy in the negative power region of H2 and release that stored energy during the H3 region to assist in swinging the leg forward. A passive hip spring exoskeleton joint design is very appropriate for slow walking speeds. In FIG. 9, an approximate linear relationship can be seen between the hip torque and angle for slow walking (0.8 m/s). As well as adding power throughout the gait cycle, a force-controllable actuator at the hip could be programmed to experiment with various hip stiffness values.

Knee Kinematics and Kinetics

Figure 10:
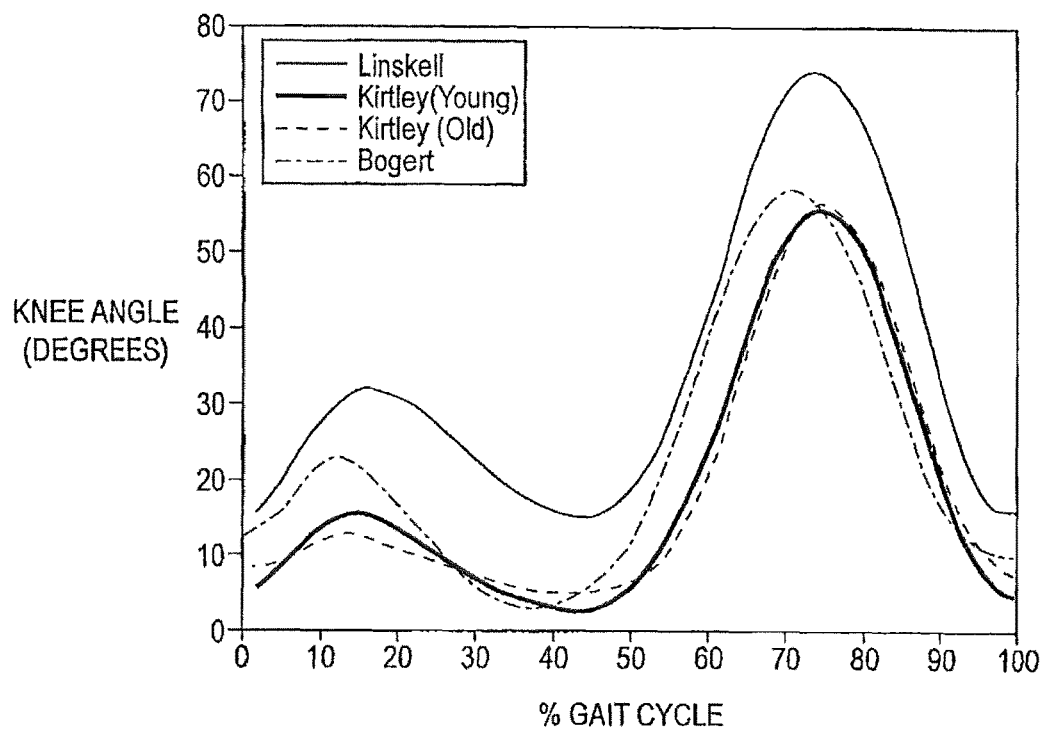
FIG. 10 is a graph showing how knee angle varies during the walking cycle.
Figure 11:
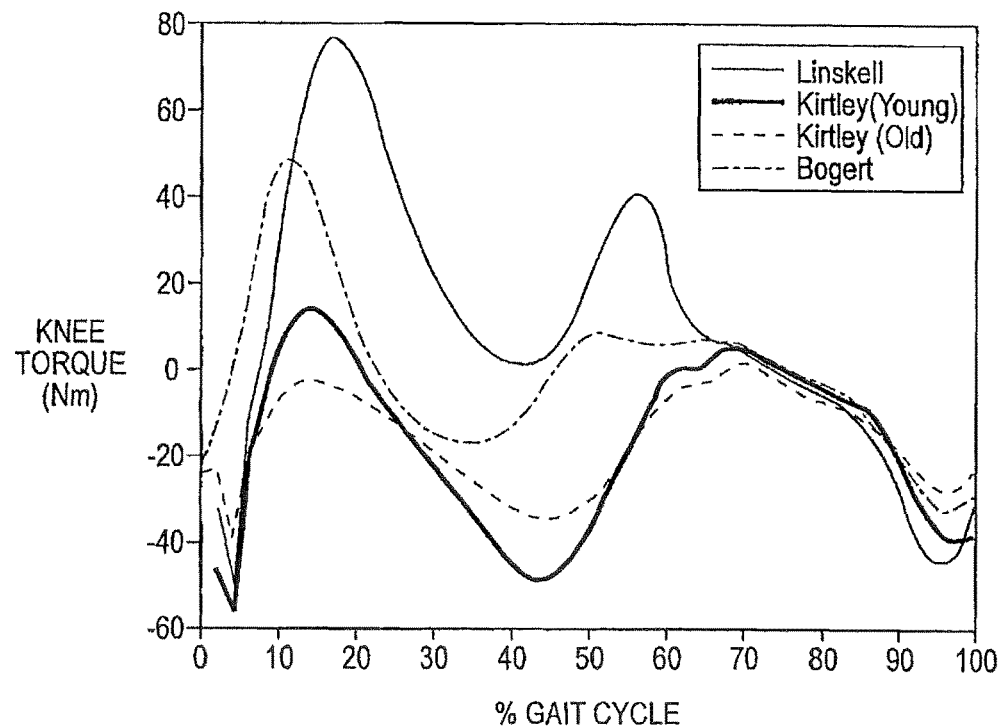
FIG. 11 is a graph showing how knee torque varies during the walking cycle.

FIGS. 10 and 11 show plots of the angle and torque profile of the human knee joint as a function of gait cycle. There is an initial knee flexion-extension period as the leg accepts weight after heel strike, and then a rapid knee flexion during terminal stance occurs to allow for foot clearance during the swing phase. On heel strike the knee bends slightly while exerting a maximum negative torque of 40 Nm as the weight is transferred to the leg.

Figure 12:
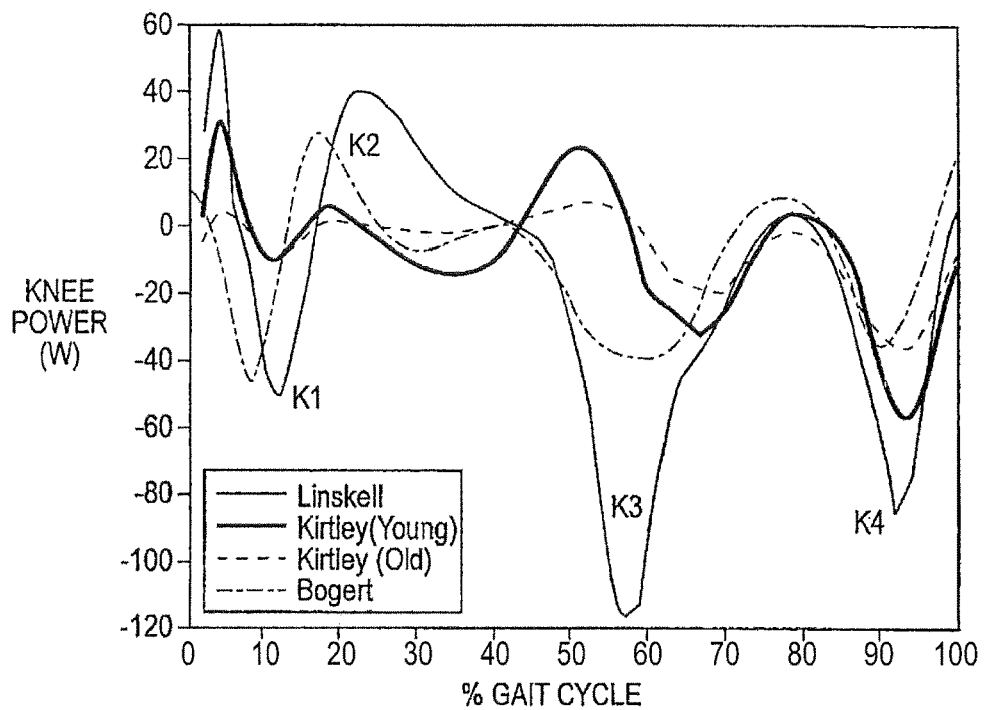
FIG. 12 is a graph showing how knee power varies during the walking cycle.
Figure 13:
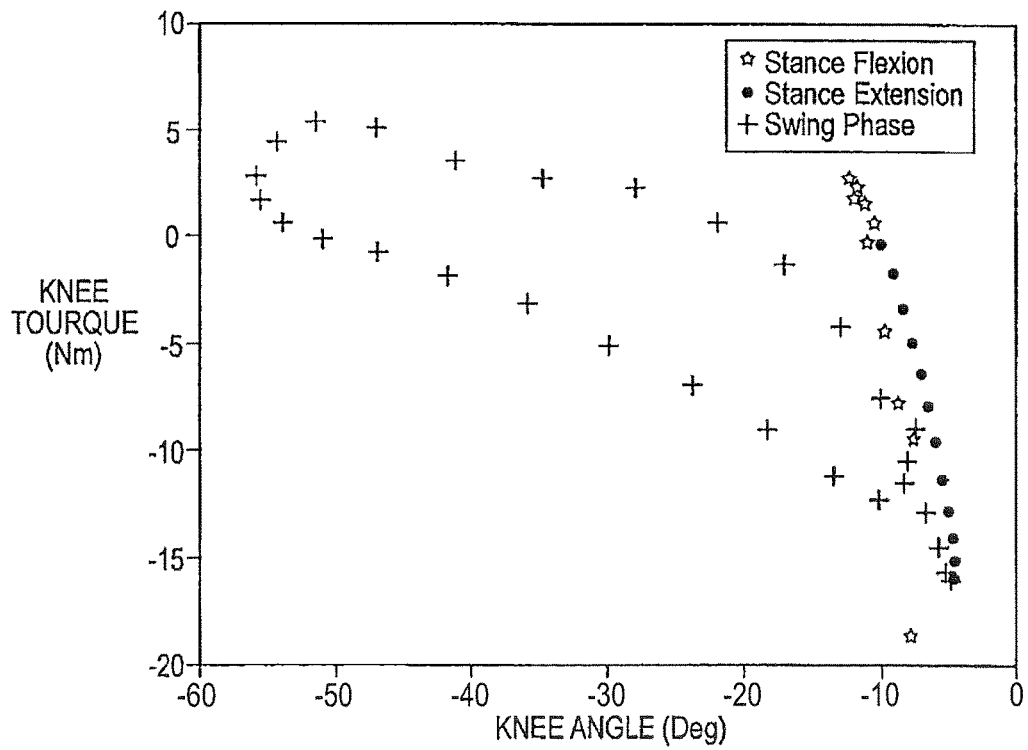
FIG. 13 is a graph showing the relationship between knee torque and knee angle.

FIGS. 12 and 13 depict the power of the knee as a function of gait cycle and it can be seen that the power is largely negative. At heal strike there is a region of negative power followed by positive power as the knee goes through stance flexion-extension. This is followed by a period of negligible joint power as the knee is passively extended as the quadriceps are inactive as ground reaction forces, as well as activity in the ankle plantar flexors keep the knee stabilized in extension due to the ground reaction force. For a large part of swing, the leg has a pendulum-like motion, and the knee undergoes eccentric activity to dampen the swinging leg.

FIGS. 12 and 13 show the knee joint power profile scaled for a 60 kg person as a function of gait cycle. K1 is a region of negative power, corresponding to eccentric knee extensor activity during the loading response, and K2 is a region of positive power, corresponding to concentric knee extensor activity during mid-stance. K3 is a region of negative power, corresponding to eccentric activity in the rectus femoris during pre-swing, and K4 is a region of negative power, corresponding to eccentric activity in the hamstrings during terminal swing. Plotted in FIG. 13 is knee angle versus knee torque for the walking cycle. It can be seen that the knee can be modeled as a variable-damping device throughout the gait cycle with the exception of region K2.

It can be seen in the knee torque vs. angle plot that during early stance phase the knee behaves like a spring, but for the remainder of the gait cycle, the knee response can be modeled as a variable damper. From this observation, a variable-damping device at the knee seems sufficient for actuation at the exoskeleton knee.

Ankle Kinematics and Kinetics

Figure 14:
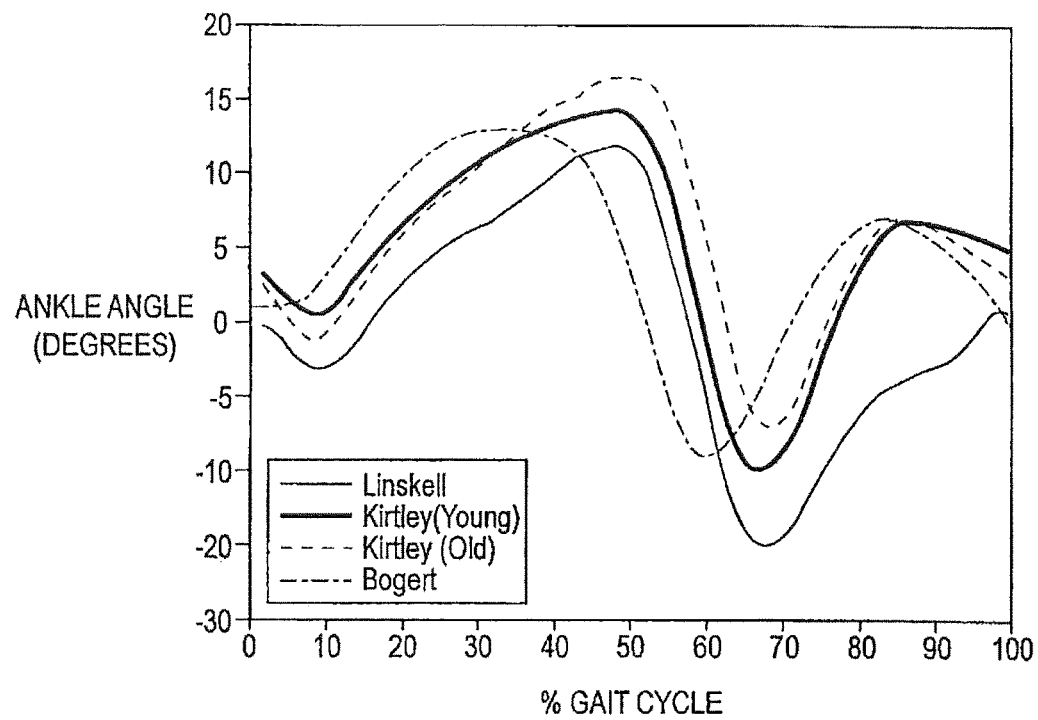
FIG. 14 is a graph showing how ankle angle varies during the walking cycle.
Figure 15:
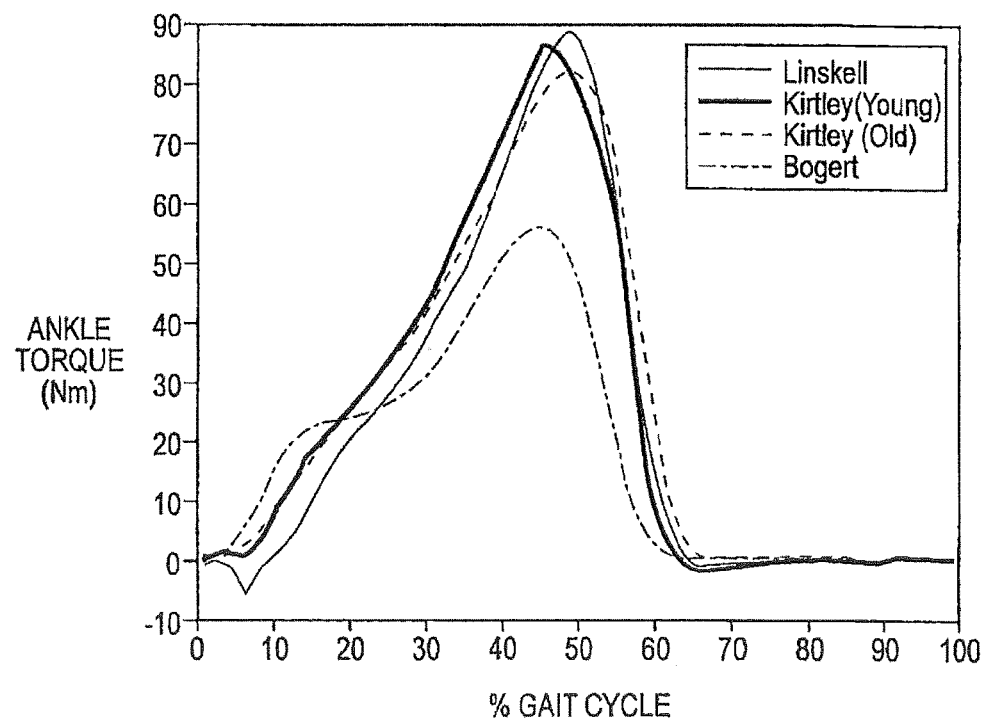
FIG. 15 is a graph showing how ankle torque varies during the walking cycle.

FIGS. 14 and 15 show ankle angle and torque profiles scaled for a 60 kg person. The ankle joint experiences approximately 15 degrees of rotation in both directions throughout the gait cycle. During the mid and late stance phases of walking, the ankle eccentric plantar flexor activity creates negative joint torque as the ankle controls the forward movement of the center of mass. The peak torque experienced by the ankle is approximately 90 Nm.

Figure 16:
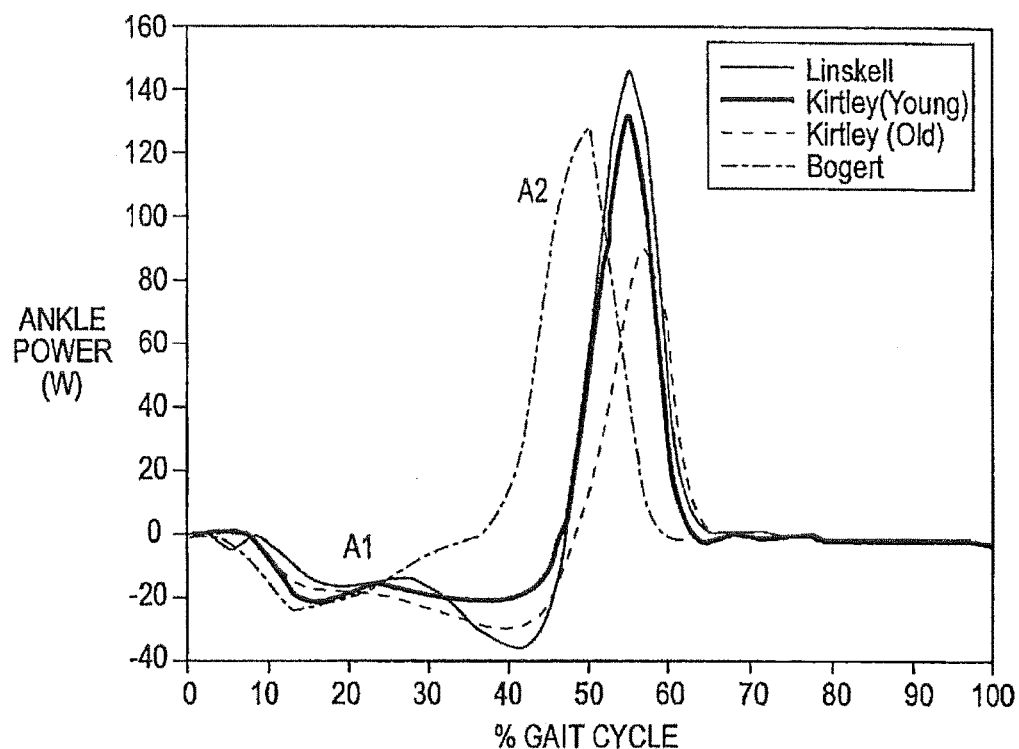
FIG. 16 is graph showing how ankle power varies during the walking cycle.
Figure 17:
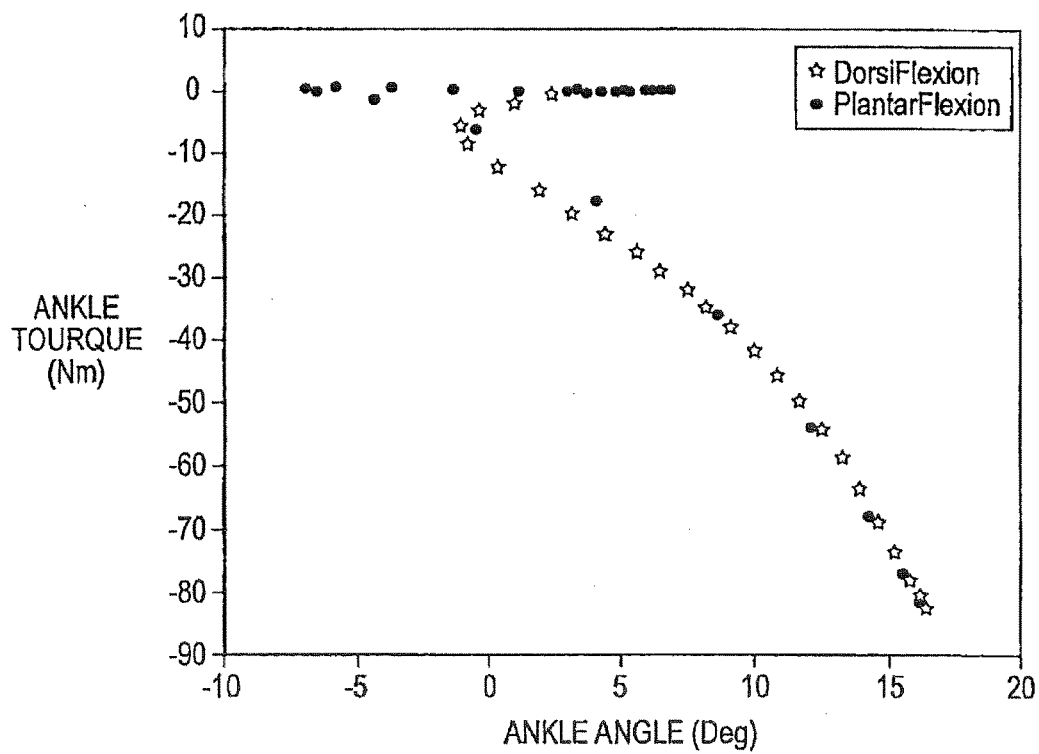
FIG. 17 is a graph showing the relationship between ankle torque and ankle angle.

FIGS. 16 and 17 show the joint power profile scaled for a 60 kg person as a function of gait cycle. A1 is a region of negative power, corresponding to eccentric plantar flexor activity at the ankle during mid-stance and terminal stance, and A2 is a region of positive power, corresponding to the concentric burst of propulsive plantar flexor activity during pre-swing. FIG. 17 is a plot of ankle angle versus ankle torque for the walking cycle. It can be seen that the ankle behaves like a spring at a walking speed of 0.8 m/s.

For slow walking the region of negative work, A1, is approximately equal to the region of positive power, A2 suggesting that a spring at the ankle may be an appropriate choice for actuation the exoskeleton ankle. At faster walking speeds A2 is significantly larger indicating that a non-conservative actuator is required. A linear fit yields a spring constant for the ankle of 229 Nm/rad for this walking speed. This implies that, for slow walking, a spring could be placed at the ankle of the exoskeleton, thus helping to minimize the negative effects of distal exoskeleton mass.

Running

Figure 18:
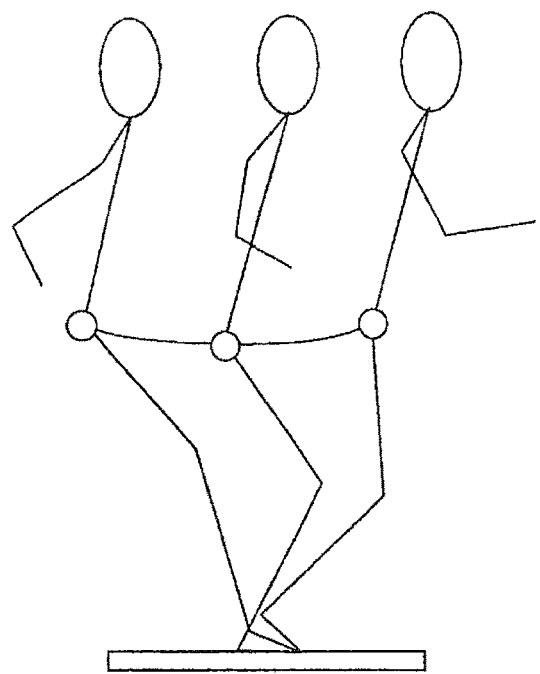
FIG. 18 illustrates human running.
Figure 19:
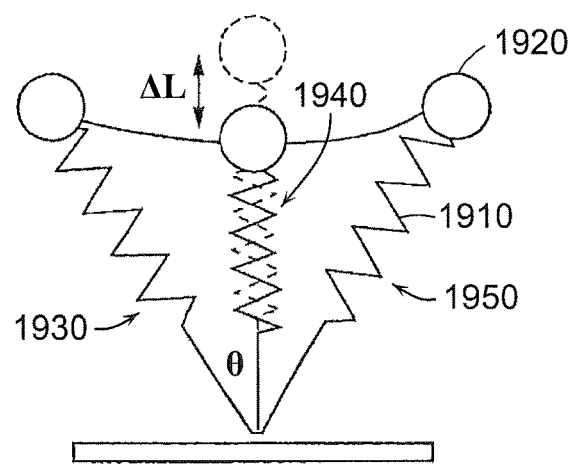
FIG. 19 illustrates the spring model of human running.

A simple model of running is shown in FIGS. 18 and 19. FIG. 19 is a spring-mass model and FIG. 18 is a stick figure representation of a single stance phase of human running. The model of FIG. 19 consists of linear spring 1910 representing the leg and point mass 1920 equivalent to body mass. This figure depicts the model at the beginning 1930 of the stance phase (left-most position), at the middle 1940 of the stance phase (leg spring is oriented vertically), and at the end 1950 of the stance phase (right-most position). For running, the biological leg can be modeled as a linear spring between the runner's center of mass and the ground. The center of mass has a parabolic trajectory.

Technical Description

Exoskeleton for Walking

Carrying the Human Vs. Carrying a Backpack

Based on the results of Farley & McMahon, as well as those of Gottschall and Kram, an exoskeleton or orthosis that supports the weight of the wearer and that provides a forward propulsive force will dramatically lower metabolic transport requirements. See Farley, C. & McMahon, T. (1992), 'Energetics of walking and running: insights from simulated reduced-gravity experiments', The American Physiological Society pp. 2709-2712 and McMahon, T. A., Valiant, G., & Frederick, E. C. (1987). Groucho Running, Journal of Applied Physiology, 62(6) 2326-2337

The weight of the wearer can be supported with various types of harnesses and pelvic attachments.

The first of these designs is a compliant off the shelf stunt harness shown in FIG. 19 that employs a back pack and leg exoskeleton arrangement where the load of the back pack is transmitted to the ground. A harness is flexible, and causes a problem with the exoskeleton side mounts. The mounts, when the exoskeleton is loaded, bend inward digging into the wearer above the pelvis.

Figure 20:
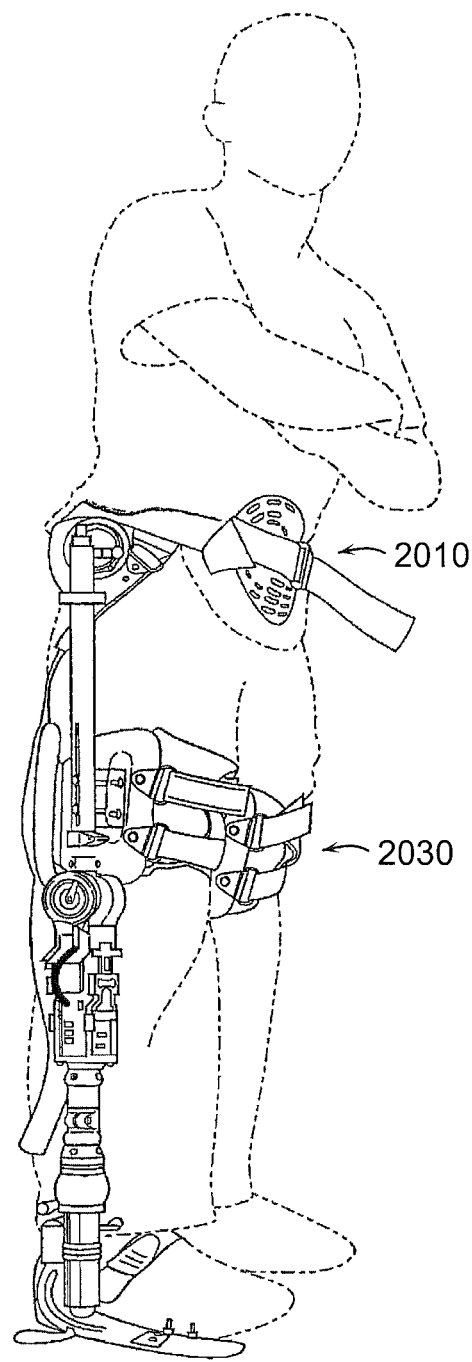
FIG. 20 depicts a backpack and connected leg exoskeleton where the load of the backpack is transmitted to the ground.
Figure 21:
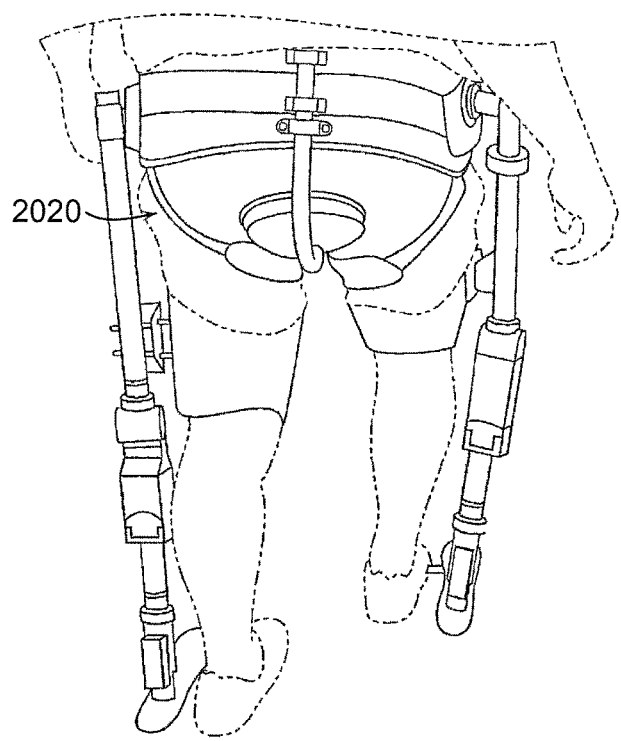
FIG. 21 depicts a harness with a bicycle seat for supporting the wearer's weight on a leg exoskeleton.

As a resolution to this difficulty, the arrangement shown in FIGS. 20 and 21 employs a carbon fiber pelvic girdle 2010 with a seat 2020 and strapping system 2030. The device provides rigid mounting planes on the sides of the pelvis for the exoskeleton legs. A fabricated, light-weight carbon composite belt and seat with supporting straps is coupled to the exoskeleton for supporting a user's weight and a bike seat or the like is used to transfer the weight of the user to the ground surface.

Intimate Form-Fit Vs. Adjacent Robotic Structure

Figure 22:
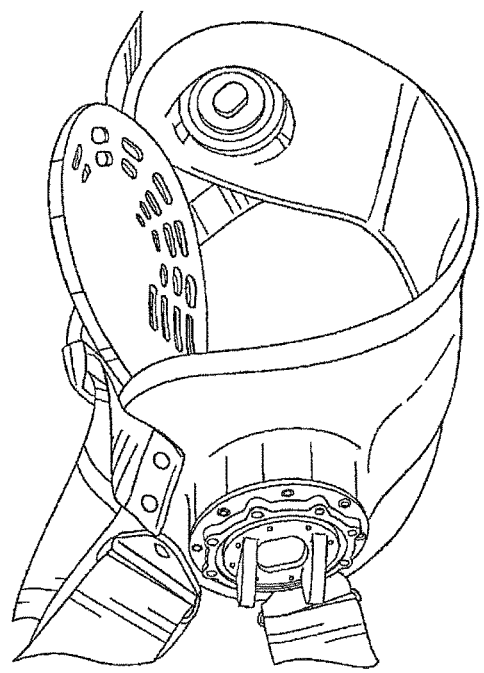
FIG. 22 depicts a carbon fiber pelvic harness and seat with a hip joint attachment to the exoskeleton legs.

In the design of an exoskeleton to support the weight of the wearer and to provide a forward propulsive force, two strategies are pursued. The first strategy, shown in FIG. 22, is a lightweight, intimate carbon fiber composite suit molded to the wearer at the foot, shank, thigh and pelvis, and the second strategy, shown in FIG. 24 is an adjacent robotic leg in parallel with the human leg connected at the foot, thigh, and pelvis.

Figure 23:
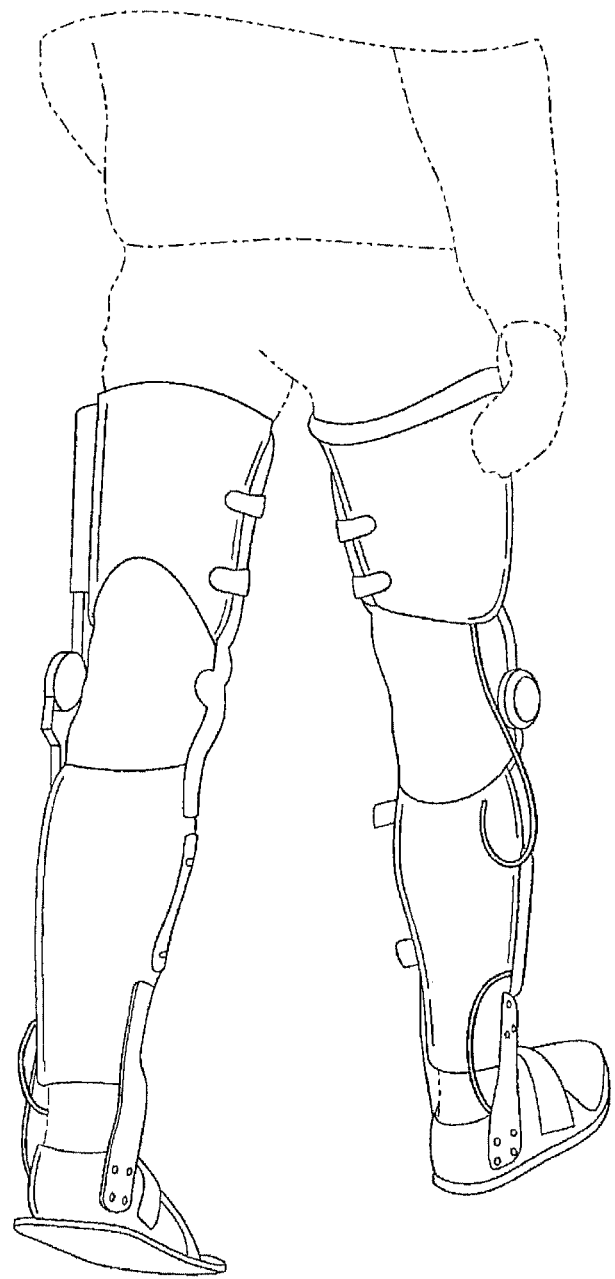
FIG. 23 depicts a carbon molded thigh and exoskeleton shin sections used in an alternative support structure.

In the arrangement shown in FIG. 23, electromagnetic clutches are placed at the exoskeleton knee joints, and series elastic actuators power the hips. This strategy requires torso, thigh, shank, and foot attachments to provide support at the hip, knee, and ankle joints. The carbon fiber structure is custom fit to the wearer. Using this method it is possible that the interface between the human and the exoskeleton, in the regions of the shank and thigh, take some of the weight of the wearer. This approach lends itself to providing power to augment the wearer's hips due to the high stiffness of the thigh and torso sections, although it would be difficult to generalize the carbon sections to many users.

Figure 24:
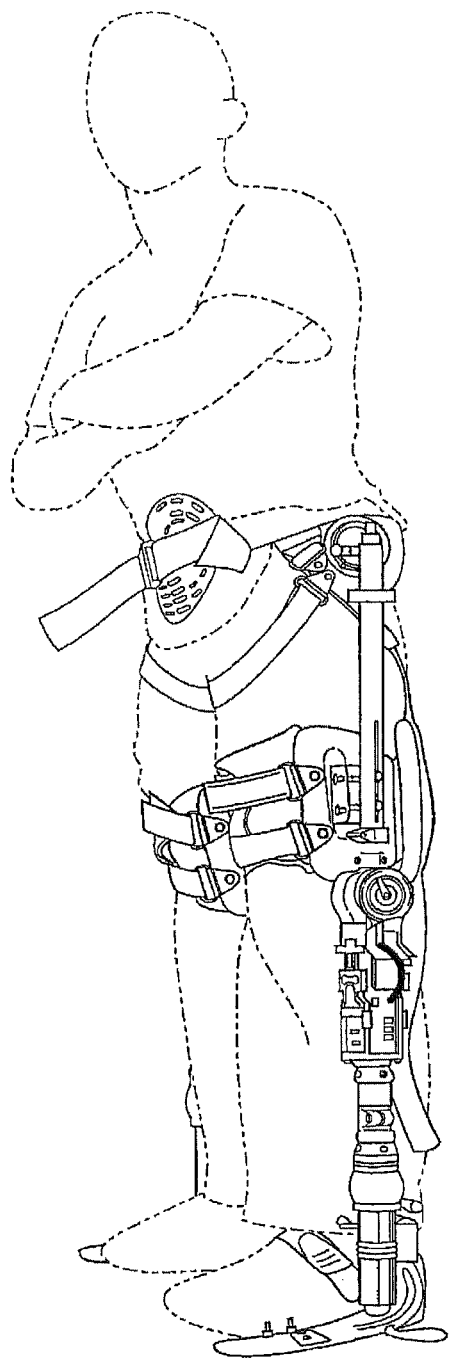
FIG. 24 depicts an exoskeleton leg system adjacent to the human leg connected at the foot, thigh and pelvis.

The second architecture, shown in FIG. 24, employs a parallel robotic leg adjacent to the human leg, instead of the molded carbon fiber structure. This architecture is deemed preferable to the molded architecture because 1) the system only interfaces with the human at the foot, thigh, and pelvis; and 2) the system is more readily adjustable to different human morphologies.

Overall Joint Actuation Strategy

Figure 25:
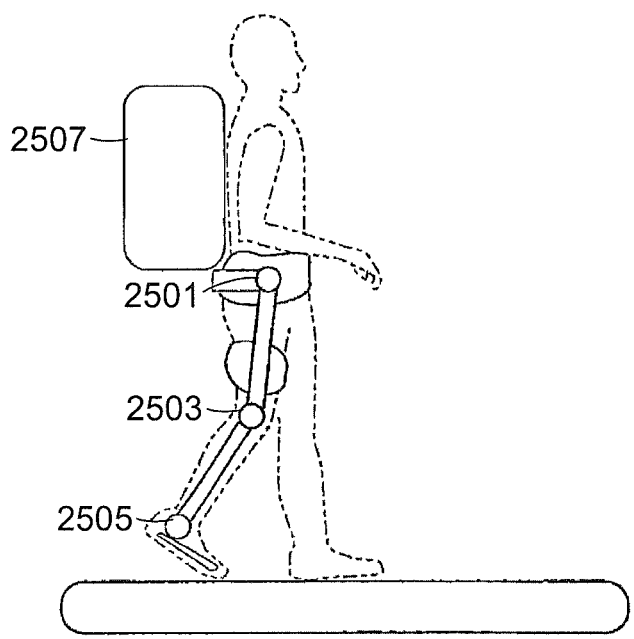
FIG. 25 illustrates the main components of a walking load-carrying exoskeleton.

Two exoskeleton joint architectures are examined for walking. The main components of the walking, load-carrying exoskeleton are shown in FIG. 25.

A first architecture consists of springs at the hip 2501, a variable impedance device at the knee 2503, and springs at the ankle 2505. In a second architecture, non-conservative actuators are placed at the hip 2501 to further augment hip flexion and extension to examine the effect of adding power at desired instances throughout the gait cycle.

A state-machine control strategy is written based on joint angle sensing as well as ground-exoskeleton force interaction sensing. When the human foot is on the ground, the exoskeleton transfers the forces from the loaded backpack to the ground. For level ground ambulation, a passive extension spring at the hip 2501 engages in mid-stance and stores energy and then that stored energy is released at the beginning of the hip flexion phase to assist in lifting the exoskeleton and human leg from the ground surface.

Using the second exoskeleton architecture, positive power from hip actuators is added at the hip 2501 during the stance phase to propel the mass of the human and the payload 2507 forward, and to cancel the mass of the human and exoskeleton leg during the swing phase. For level ground ambulation, the variable damper at the knee 2503 is turned on during early stance to provide support for the load and is then switched off during terminal stance and swing to minimize resistance at the knee joint. For slope descent, the variable-damper knee is turned on throughout the entire stance period to assist the human knee in lowering the backpack mass 2507. Finally, the passive spring structure at the ankle 2505 engages in controlled dorsiflexion to store energy that is later released to assist in powered plantar flexion.

Hybrid Actuators

The above-noted co-pending application Ser. No. 11/395, 448, entitled "Artificial human limbs and joints employing actuators, springs, and Variable-Damper Elements", filed on Mar. 31, 2006, describes Biomimetic Hybrid Actuators which use an electric motor for supplying positive energy to and storing negative energy from one or more joints which connect skeletal members, as well as elastic elements such as springs, and controllable variable damper components, for passively storing and releasing energy and providing adaptive stiffness to accommodate level ground walking as well as movement on stairs and surfaces having different slopes. These hybrid actuators are described in detail in application Ser. No. 11/395,448, the disclosure of which is incorporated herein by reference. Actuators used to implement hip, knee and ankle joints are described which may be used to implement an exoskeleton of the type contemplated by the present invention.

These hybrid actuators manipulate first and second skeletal members connected at one or more joints for movement relative to one another. A motor applies a force to move one member with respect to the other. One or more passive elastic members are connected between the skeletal members for storing energy when the members move relative to one another in one direction and for releasing energy when the members relative to one another in the opposite direction, and one or more controllable variable damping elements dissipate mechanical energy to arrest the relative motion of the first and second members at controllable times. Some of the hybrid actuators provide additional force by using a catapult mechanism in which the motion of the members is arrested by a controllable damping element while the motor stores energy in one or more elastic members and the damping element thereafter releases the members which are then moved by the energy stored in the elastic member. One or more damping elements may be operatively connected in parallel with the motor to arrest its motion while energy is stored in one or more elastic members and thereafter the motor parallel damping element releases the motor to release the energy previously stored in the elastic member.

The hybrid actuator may employ an elastic member operatively connected in series with a controllable damping member. When the controllable damping member exhibits a higher damping level, energy is stored in the series elastic member and thereafter, when the controllable damping member exhibits a lower damping level, energy is released from the series elastic member. The motor in the hybrid actuator may apply torque to a joint or joints through a gearbox and a first controllable variable damping element can be employed to arrest the motion of the motor at controllable times, and a further controllable variable damping element operatively connected between the motor and the gearbox can disconnect the motor and the gearbox at controllable times, such that the gearbox can be used as a damping element to arrest the motion of skeletal members at some times, and be used to apply force to move the members at other times.

As described in application Ser. No. 11/395,448, an artificial ankle may employ an elastic member operatively connected in series with the motor between the shin member and the foot member to store energy when the relative motion of the foot and shin members is being arrested by a controllable variable damping element and to thereafter apply an additional torque to the ankle joint when the variable damping element no longer arrests the relative motion of the two members.

Copending patent application Ser. No. 11/495,140, entitled "An Artificial Ankle-Foot System with Spring, Variable-Damping, and Series-Elastic Actuator Components", filed on Jul. 29, 2006, describes an artificial ankle and foot system in which a foot and ankle structure is mounted for rotation with respect to a shin member at an ankle joint. The foot and ankle structure includes a curved flexible elastic foot member that defines an arch between a heel extremity and a toe extremity, and a flexible elastic ankle member that connects said foot member for rotation at the ankle joint. A variable damper is employed to arresting the motion of said foot and ankle structure with respect to said shin member under predetermined conditions, and preferably includes a stop mechanism that prevents the foot and ankle structure from rotating with respect to the shin member beyond a predetermined limit position. The variable damper may further include a controllable damper, such as a magnetorheological (MR) brake, which arrests the rotation of the ankle joint by controllable amount at controlled times during the walking cycle. The ankle and foot system may include an actuator motor for applying torque to the ankle joint to rotate the foot and ankle structure with respect to said shin member, and/or a catapult mechanism comprising a series elastic member operatively connected in series with the motor between the shin member and the foot and ankle structure in which the series elastic member stores energy from the motor during a first portion of each walking cycle and then releases the stored energy to help propel the user forward over the walking surface at a later time in each walking cycle. The actuator motor which applies torque to the ankle joint may be employed to adjust the position of the foot and ankle structure relative to the shin member when the foot and ankle member is not in contact with a support surface. Inertial sensing means may be employed to determine the relative elevation of the foot and angle structure and to actuate the motor in response to changes in the relative elevation, thereby automatically positioning the foot member for toe first engagement if the wearer is descending stairs.

Mechanical Design

The exoskeleton is designed to provide a parallel load path that transfers the weight of the backpack or wearer directly to the ground. The exoskeleton has sufficient degrees of freedom to minimize kinematic constraints experienced by the wearer. The system is designed so that the distal mass of the exoskeleton is minimized. Hip actuation in the sagittal plane is designed so as to minimize the interaction forces between the exoskeleton and the wearer.

Exoskeleton Structure

The design of an exoskeleton structure must address the fact that the structure's primary function is to support the payload and provide the mechanical interface to the operator so that an assistive propulsive force can be applied to the operator. In essence, the exoskeleton is wrapped around the operator and supports the payload as well as its own load with the objective of minimizing disturbances exerted on the operator. It is also important in exoskeleton design that proximal exoskeleton mass is minimized. A parallel orthotic structure, or the second strategy outlined earlier, is the preferred framework to transfer the load from the backpack to the ground. In the exoskeleton design described herein, the main structural elements consist of standard prosthetic aluminum tubing. This tubing was chosen since it is lightweight, rated for human use, and interfaces with standard prosthetic alignment connectors and components. The criteria for sizing the structural elements must take into consideration not only the stresses, but also the structural stiffness. Thus, minimizing the size and weight of the structural elements must be considered while also maintaining structural stiffness so that the payload can be adequately supported.

For an exoskeleton to move from the laboratory and be available for practical use it must be adjustable to accommodate a wide range of operator sizes. The goal is to accommodate from the 5% female to the 95% male by adjusting the upper and lower leg segments. Adjustable tube clamps are used to vary the length of the exoskeleton shank and thigh leg segments, and four-screw prosthetic alignment fixtures are used for alignment.

Exoskeleton Degrees of Freedom

Figure 26:
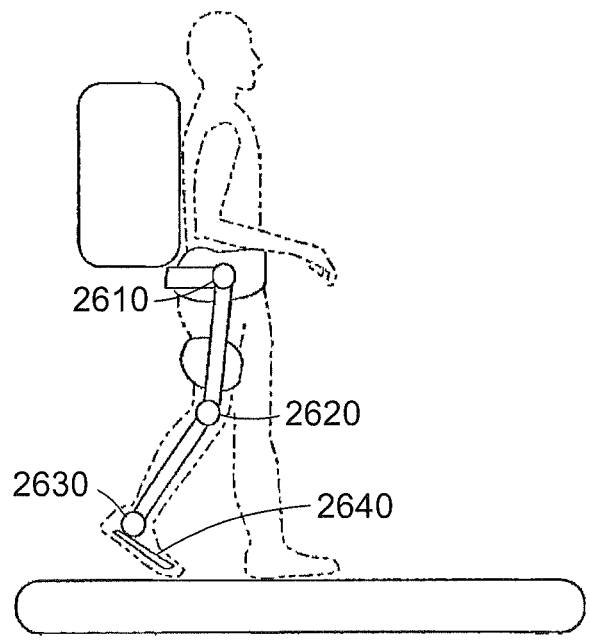
FIG. 26 illustrates the degrees of freedom of the exoskeleton structure.

As seen in FIG. 26, the exoskeleton is implemented with three degrees of freedom at the hip 2610 (flexion/extension, abduction/adduction), one at the knee 2620 (flexion/extension), two at the ankle 2630 (flexion/extension), and one at the foot 2640. The joint ranges of motion accommodate normal human walking. A cam mechanism is implemented at the hip joint to enable hip abduction/adduction.

Figure 27:
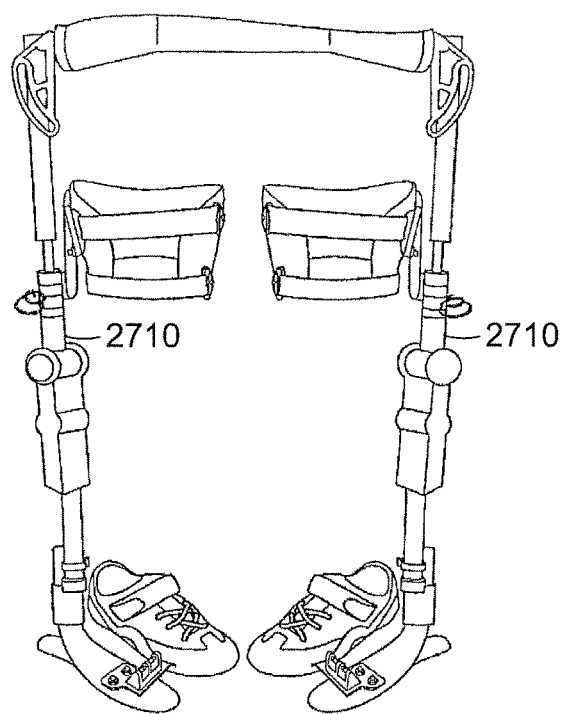
FIG. 27 depicts the exoskeleton system.

The exoskeleton hip joint can accommodate the hip's three degrees of freedom which are (1) flexion/extension, (2) abduction/adduction, and (3) medial/lateral rotation. As seen in FIG. 27, revolute joint and Ignus bearings 2710 allow hip and medial/lateral rotation. Medial/lateral rotation is realized in one embodiment by means of a ½ I.D. Igus GFI-080906 plain bearing located above the exoskeleton knee.

Figure 28:
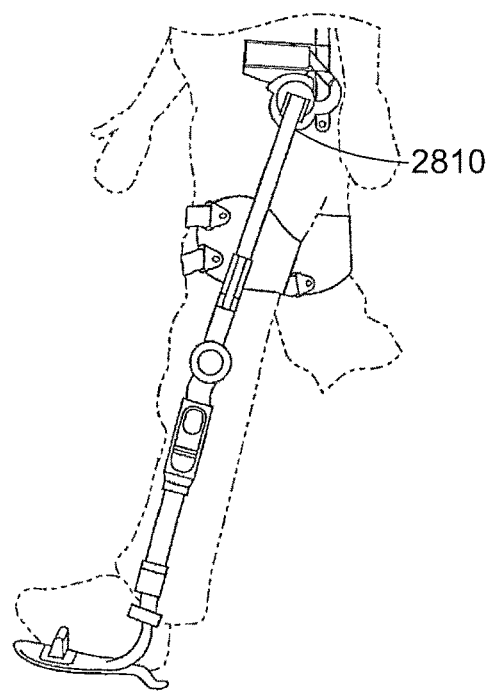
FIG. 28 is a side view of the exoskeleton system as worn.

As seen in FIG. 28, hip flexion/extension degree of freedom is realized by means of Revolute joint and Kaydon bearing 2810, implemented in the prototype using a 2" I.D. Kaydon JA020XP0 reali-slim ball bearing which permits hip flexion/extension.

Cam Mechanism

Figure 29:
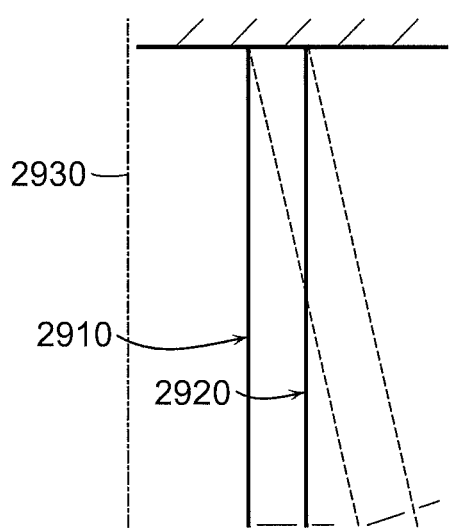
FIG. 29 is a diagram showing the length change required for an exoskeleton leg during hip abduction-adduction.

During abduction in the coronal plane, there is a length difference between the biological leg 2910 and the exoskeleton leg 2920 (FIG. 29) that results from dissimilar centers of rotation between the biological leg and the exoskeleton leg. This effect can impede normal walking motion and cause discomfort. The cam mechanism is designed to automatically adjust the exoskeleton leg length and project the center of rotation of the exoskeleton leg onto the biological hip center of rotation 2930, as seen in the frontal view shown in FIG. 29.

Figure 30:
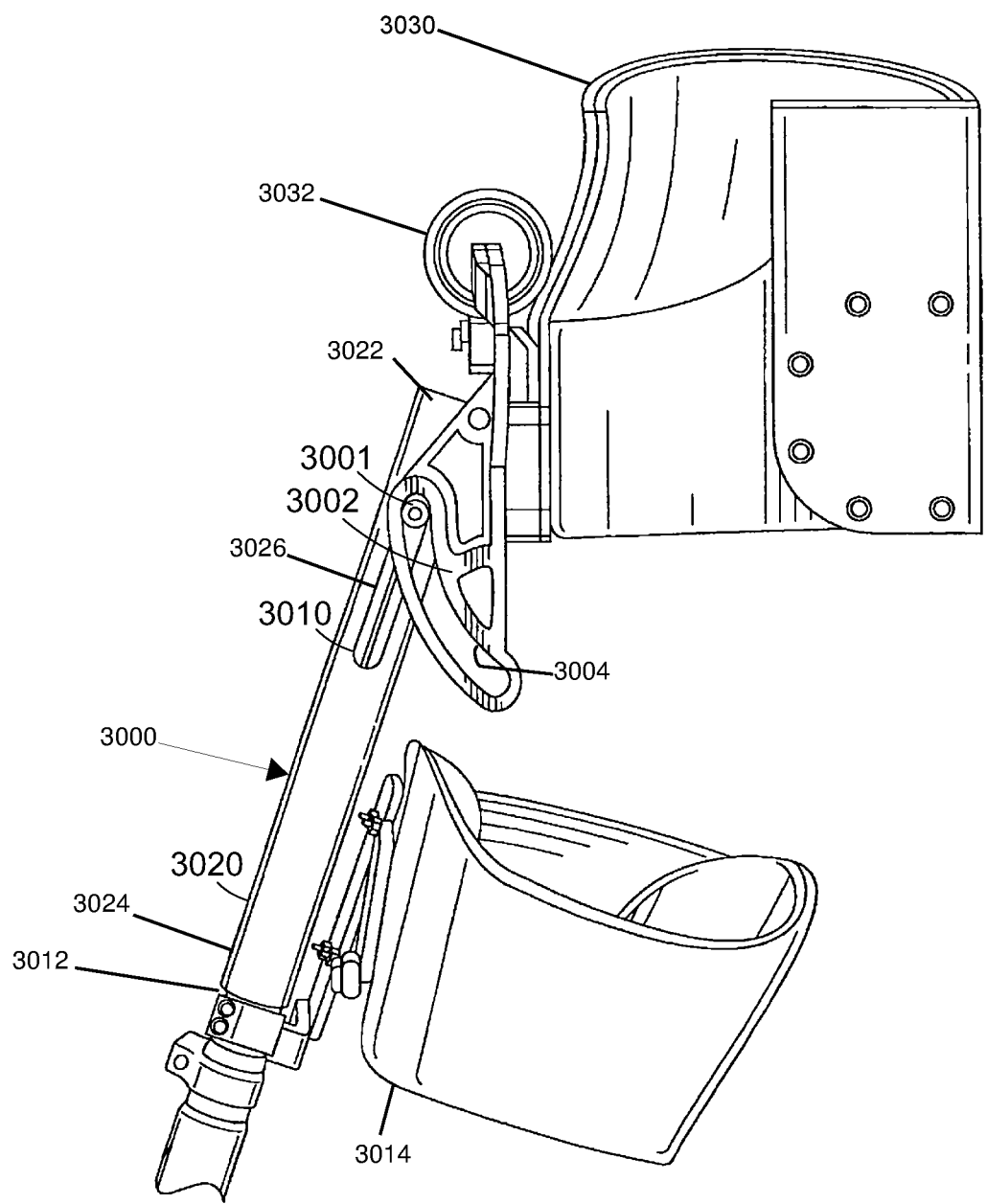
FIG. 30 depicts the cam assembly used to mitigate the change in leg length during abduction.

A cam-roller mechanism is designed to mitigate the change in leg length during abduction and still transmit the payload forces to the ground. The exoskeleton leg 3000 couples to pelvic harness 3030 by means of a slotted cam 3002 at hip joint 3032 located on the side of the hip, as seen in FIG. 30. Slotted cam 3002 defines arcuate cam slot 3004. As the biological leg abducts, a roller 3001, mechanically grounded to the exoskeleton leg, follows the contour of arcuate cam slot 3004 and the exoskeleton leg shortens and tracks the cam profile. The higher the roller 3001 moves up arcuate cam slot 3004 of slotted cam 3002, the more the exoskeleton leg shortens. The mechanism has one degree of freedom, so that for a given leg abduction angle there is a unique leg length. The profile of the cam is designed by modeling the exoskeleton leg kinematics as a four bar linkage. Also shown in FIG. 30 are shaft component 3010 and bearing housing component 3020. Bearing housing component 3020 has first end 3022 pivotally linked at longitudinal slot 3026 to slotted cam 3002 at arcuate cam slot 3004 by cam roller mechanism 3001 extending from proximal end of shaft component 3010 through longitudinal slot 3026 defined by bearing housing component 3020 and through arcuate slot 3004 of slotted cam 3002. Shaft component 3010 extends from within second end 3024 of bearing housing component 3020. Shaft component 3010 is linked at distal end 3012 to thigh member 3014.

Figure 31:
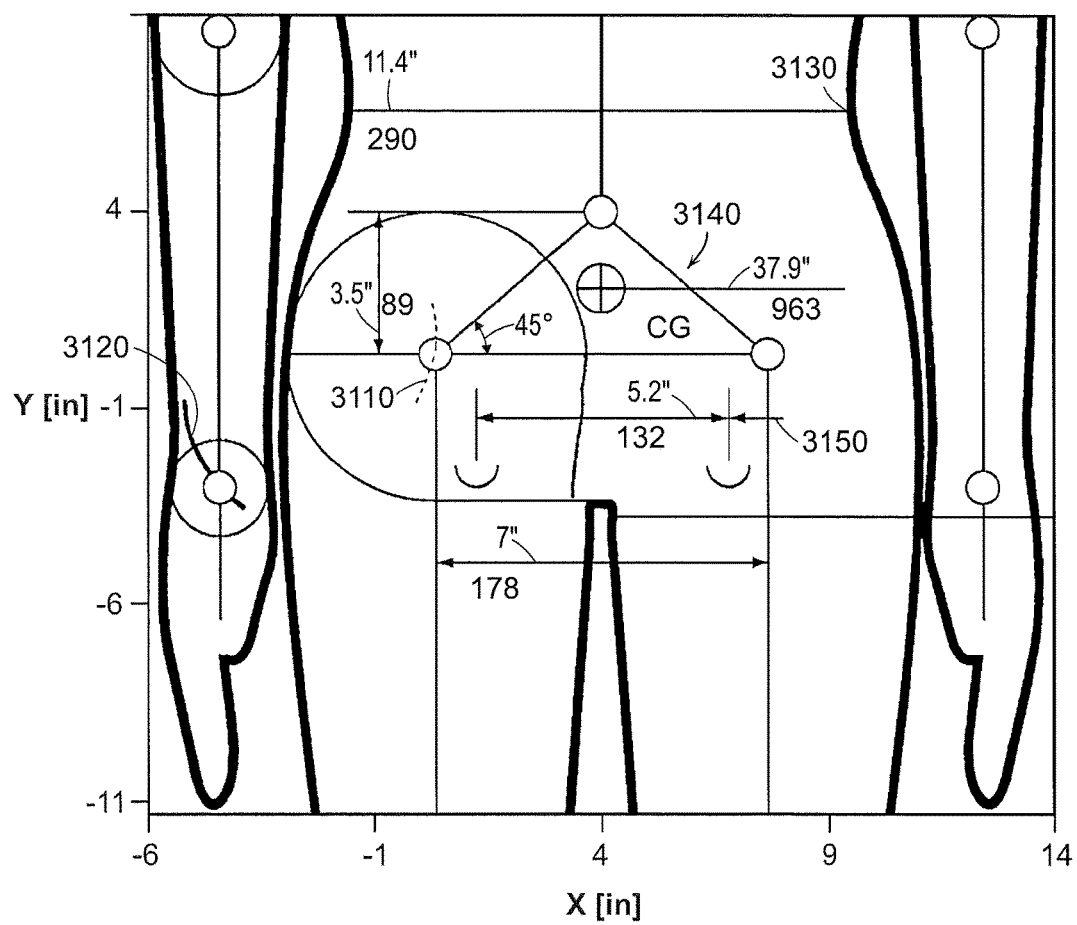
FIG. 31 is diagram illustrating the operation of the cam assembly.
Figure 47:
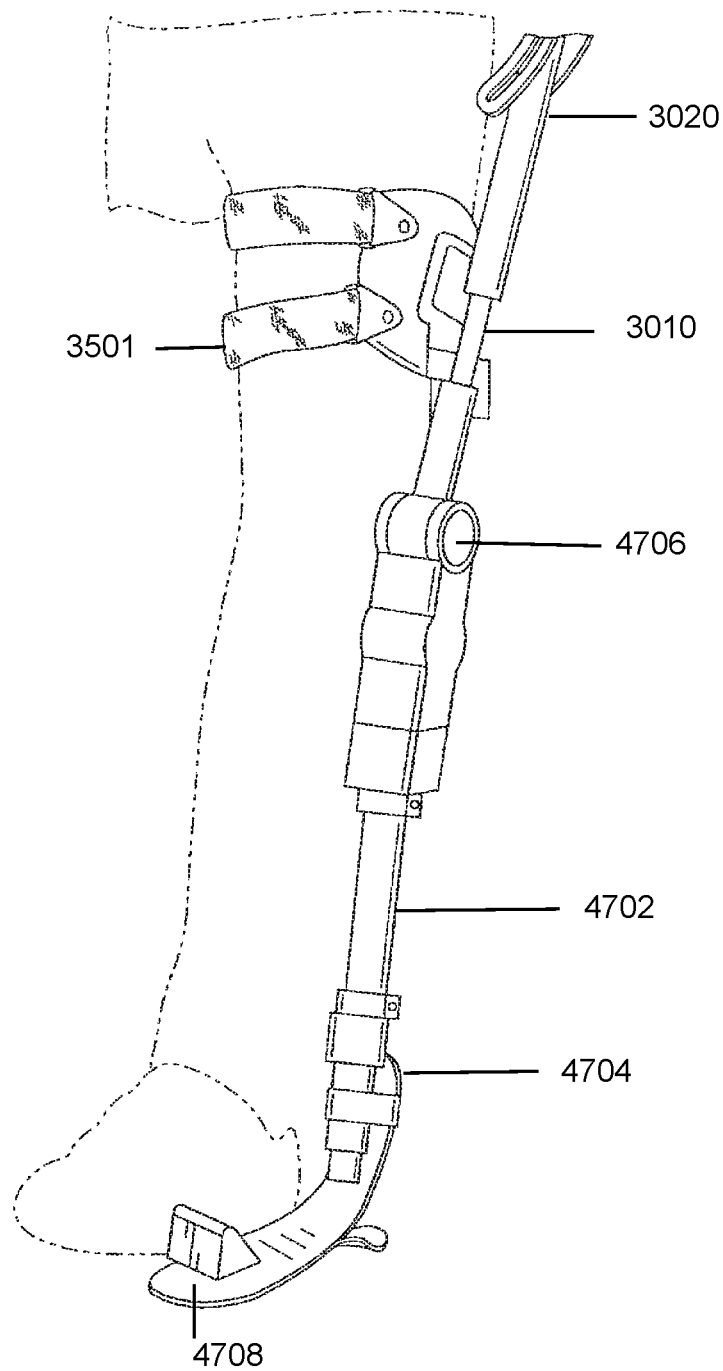
FIG. 47 depicts the knee joint of the exoskeleton containing a variable damper.

The cam is built out of titanium and installed on the exoskeleton. Titanium is chosen because its high degree of hardness lessens the rolling friction of the steel rollers while being lighter than hardened steel. Evaluations of the cam mechanism, as illustrated in FIG. 31, showed that the virtual center of rotation of the exoskeleton leg is centered on the human's biological hip center. A load bearing exoskeleton leg structure adapted to extend along the side of the leg of the human user is shown in FIG. 47. It includes a thigh member 3010, 3020 adapted to be positioned to the side of a thigh of the human user, a shin member 4702 adapted to be positioned to the side of a shin of the human user, and a knee joint 4706 joining the thigh member 3010 and the shin member 4702 and adapted to be positioned to the side of the knee of the human user. The thigh member comprises a bearing housing component 3020 and a shaft component 3010. A thigh cuff 3501 is attached to the exoskeleton leg structure at the thigh member 3010 distal to the pelvic harness, the thigh cuff being adapted to be attached to the thigh of the human user. An ankle joint 4704 joins the shin member 4702 to the foot member 4708 and is adapted to be positioned to the side of the ankle of the human user.

Spine and Pelvis

The motions of the legs are coordinated with motions of the spine, shoulders, and arms. Spine, shoulder and arm motions make walking efficient by reducing braking motions transmitted through the legs and pelvis to the upper body. Energy expenditure in walking is increased if the back is immobilized and rotational motions of the pelvis and shoulders are eliminated. This kind of restriction of the motions associated with walking requires a higher metabolic rate for walking [Carlson, S. (1972), 'How man moves', London: Heinemann].

Figure 32:
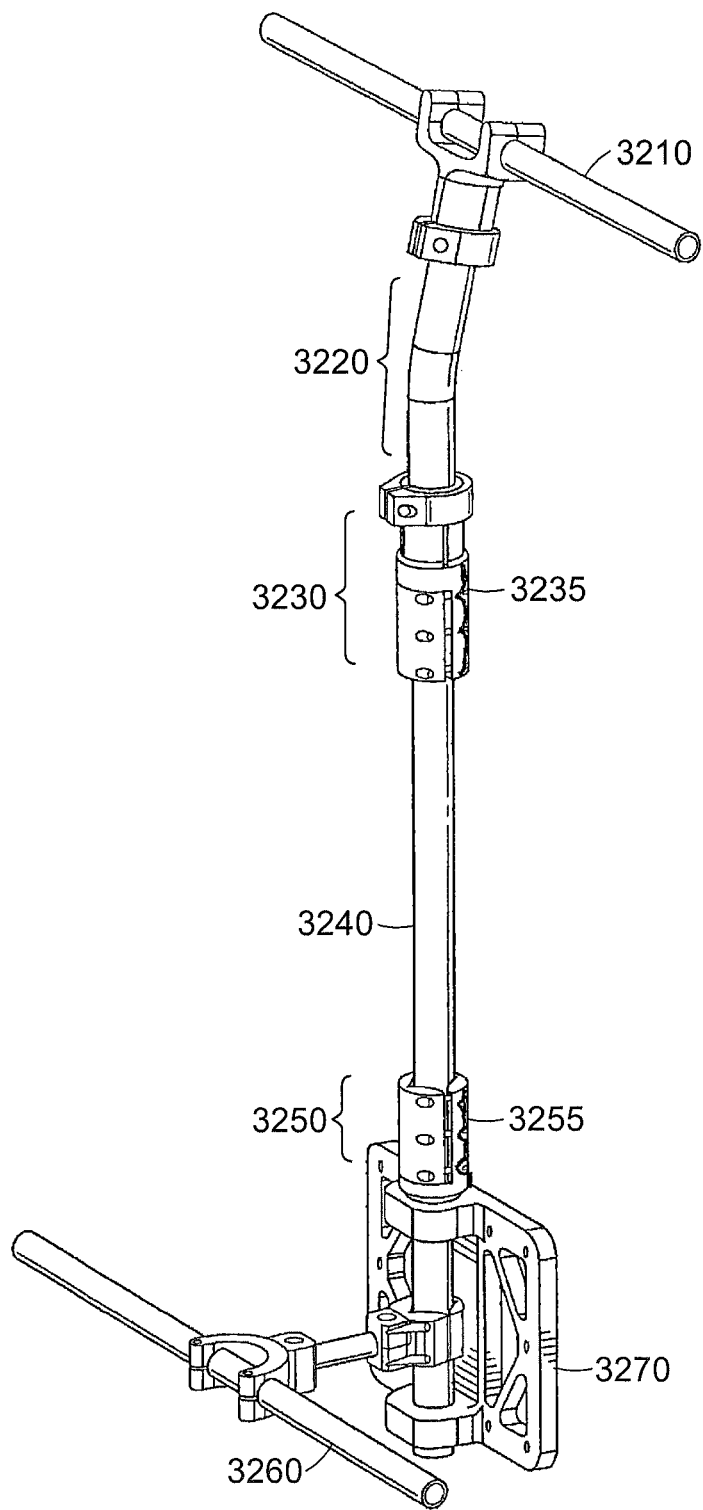
FIG. 32 is a perspective view of the exoskeleton spine assembly forming the backpack frame.

To allow more freedom for the subject during walking, the backpack frame, which was rigidly attached to the hip harness in the exoskeleton, is replaced by a flexible spine seen in FIG. 32. The backpack is supported by the top horizontal shaft 3210 of the spine. This shaft 3210 joins with a deformable tube 3220, fitted to the subject, which allows the exoskeleton spine to align with the arch of the subject's spine. A coupler 3230 joins the deformable tube 3220 to a flexible shaft 3240. The coupler 3230 contains a V-groove 3235 in order to adapt to various shafts of different diameters and stiffnesses. The flexible shaft fits into a yaw coupler 3250 that rotates freely about the vertical axis. Yaw coupler 3250 contains a V-groove 3255 in order to adapt to various shafts of different diameters and stiffnesses. A second horizontal shaft 3260 clamps onto the yaw coupler and plate 3270 bolts to the exoskeleton harness.

The human pelvis rotates from −10 to +10 degrees during normal walking. The yaw joint at the base of the spine of the exoskeleton that is connected to the pelvic harness allows the spine (and the backpack that is attached to it) to rotate as the human pelvis rotates. In addition to this movement, the flexible shaft bends during walking to allow for pelvic obliquity and tilt. By minimally constraining normal human movement, we can minimize any negative metabolic effect the exoskeleton may have on the wearer.

Exoskeleton Interface to Human

The exoskeleton interfaces to the human via shoulder straps, a waist belt, thigh cuffs, and a shoe connection. A compliant belt interfaces the lower torso to the backpack frame, and the backpack's shoulder straps interface the upper torso. The physical connection between the exoskeleton and the human enables the exoskeleton to passively track the human's leg motion. A standard military issued backpack, Alice Pack, is selected to carry the load. The exoskeleton is attached to the standard military backpack through a harness. The hip joints of the exoskeleton legs are mounted to the harness. There is sufficient clearance between the pelvic harness and the wearer to minimize disturbances to the wearer's gait.

CF Harness

The exoskeleton is attached to the standard military backpack through a harness that interfaces with the hip joint of the exoskeleton. The pelvic harness provides an intimate fit between the human and the exoskeleton in the region of the pelvis. The structure is made from carbon fiber and is attached to the backpack in a way that maximizes stiffness of the structure.

Figure 33:
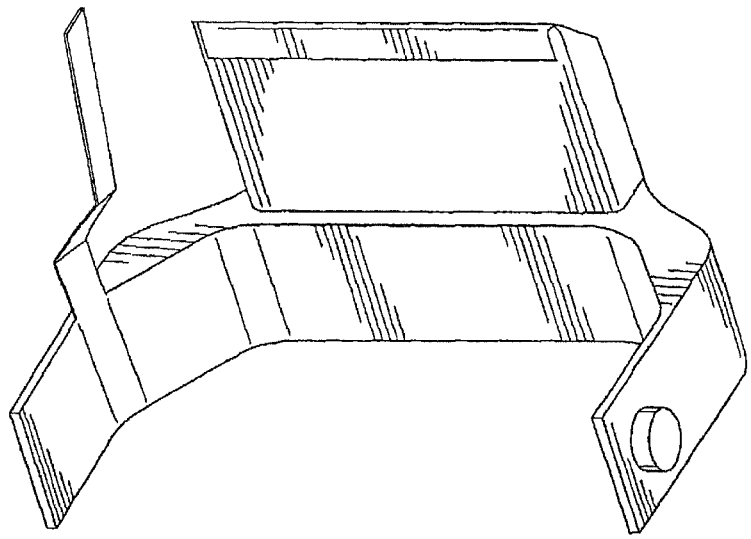
FIGS. 33 and 34 show the carbon fiber pelvic harness used in the exoskeleton.
Figure 34:
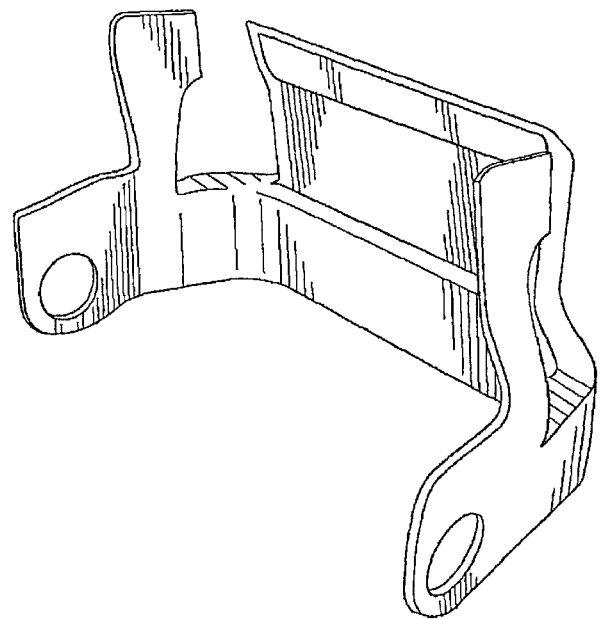

The harness connects rigidly to the backpack frame to transfer the load from the backpack to the exoskeleton. The pelvic harness is made from carbon fiber and the stiffness to weight ratio is optimized using finite element analysis. The structure consists of a hollow core with 1/16th inch thickness of carbon fiber layer over it. A box is also incorporated into the harness for electronic part storage while at the same time providing structural integrity. FIG. 33 depicts a model of the carbon fiber harness. The structure consists of a hollow core with 1/16th inch thickness of carbon fiber layer over it. FIG. 34 shows the final, constructed part.

Thigh Brace

Figure 35:
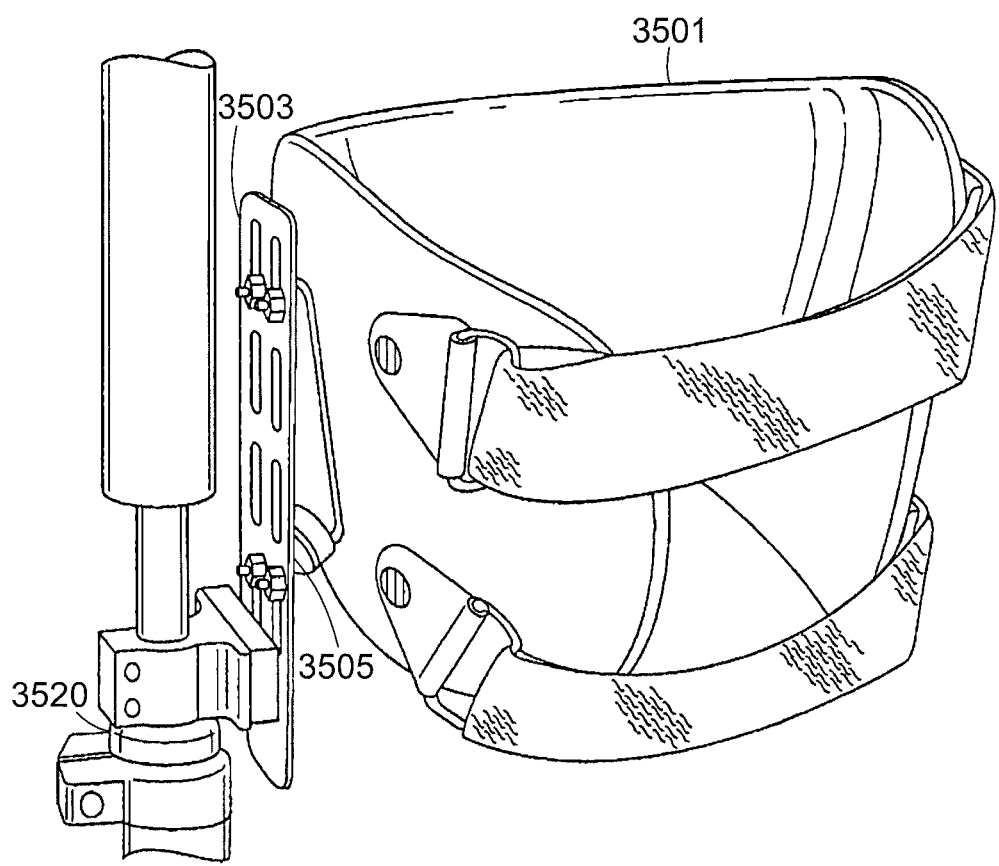
FIG. 35 depicts the thigh brace that attaches to a rotational joint allowing the human leg to rotate with respect to the exoskeleton leg.

In order for a passive system to track the knee, a body-exoskeleton attachment above and below the knee is required. A thigh cuff 3501 seen in FIG. 35 is used to help the exoskeleton track the kinematic motion of the human leg. The cuff 3501 is padded and Velcro is used to tighten the fit. A spring steel plate 3503 is installed between the exoskeleton leg and the thigh cuff. The steel plate is compliant in the coronal plane to adjust to the leg contours of different participants, but it is rigid in the sagittal plane to allow for good tracking during walking. A spacer 3505 is inserted to angle the thigh cuff inward for a better fit. Also shown is revolute joint 3520

Foot Attach

Figure 36:
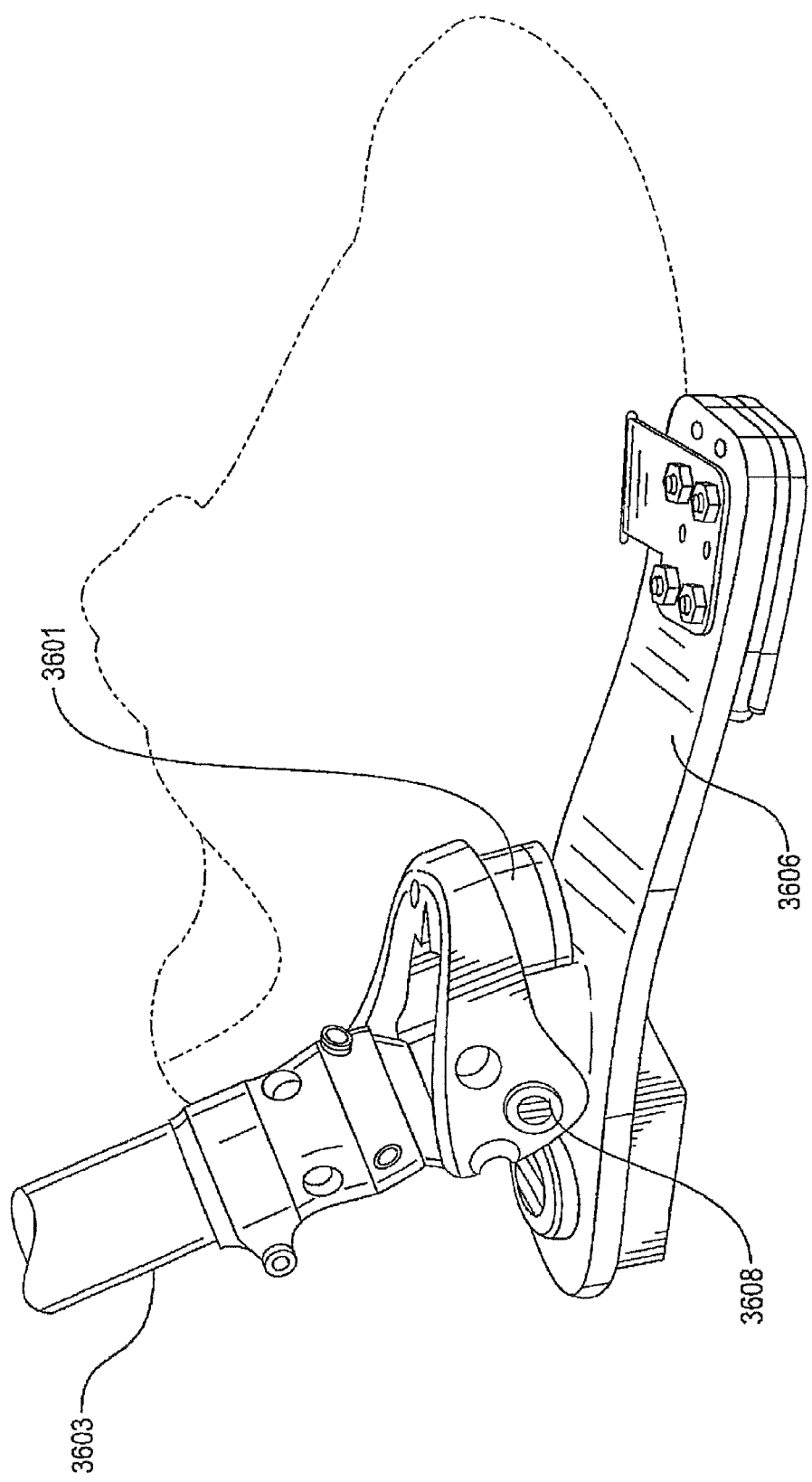
FIG. 36 depicts the ankle and foot structures used in the exoskeleton.

One approach that may be employed to attach the human foot to the exoskeleton is to attach an exoskeleton foot to the human foot with a unidirectional spring 3601 made from a piece of elastic, leaf spring material such as spring steel, as seen in FIG. 36. The exoskeleton shank 3603 attaches to a carbon fiber foot 3606 at a non-colocated ankle joint 3608. The connection is sufficiently rigid to keep the exoskeleton foot in line with the human foot and also to allow enough movement between the exoskeleton foot and the human foot in order to minimize discomfort in walking.

The design allows the payload of the exoskeleton to be transferred to the ground, but it significantly increases the foot print of the wearer plus exoskeleton and thus increases mediolateral center of mass oscillations in walking. A resolution to this difficulty is to integrate the exoskeleton seamlessly into a standard boot or shoe.

Figure 37:
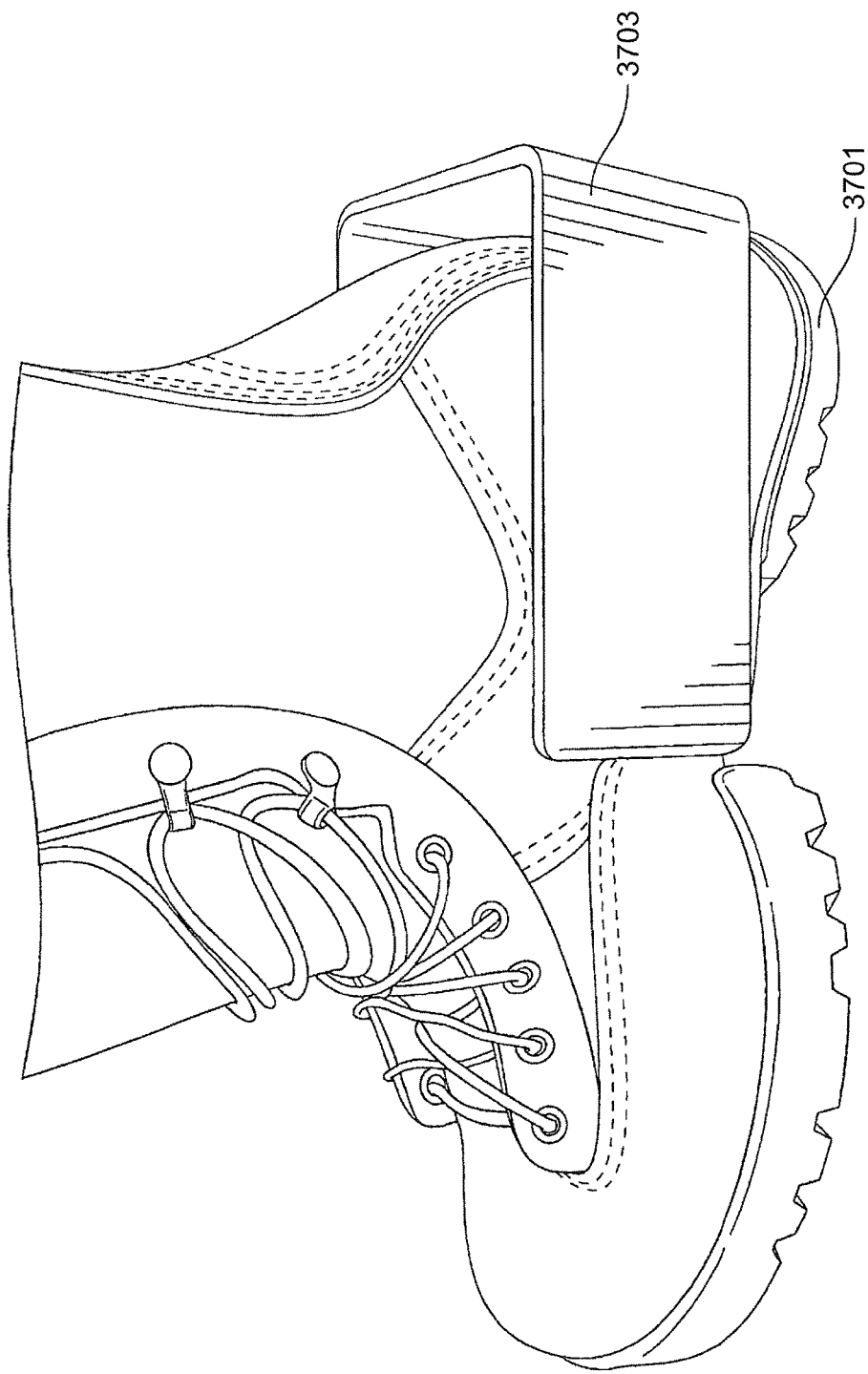
FIG. 37 depicts a modified military boot with an integrated exoskeleton attachment point and heel spring.

As a resolution to this difficulty, the exoskeleton ankle-foot joint can be integrated into a boot or shoe as is shown in FIG. 37. This design improves on the above design in that it allows the exoskeleton and human ankle joints to be collocated. Further, the exoskeleton foot is integrated into a standard military boot to greatly reduce the foot print compared to the design shown in FIG. 36. The foot print now is the same as the footprint of a standard military boot. In addition to a smaller foot print, the boot has a tuned carbon composite leaf spring at 3701. This spring acts to store energy on heel strike that is later released to help the human heel lift from the ground surface. Another benefit of the heel spring is that it adds improved shock absorption on heal strike and this minimize shock loads on the human joints. A carbon fiber plate 3703 is used to mount the exoskeleton ankle.

Hip Extension Spring

Figure 44:
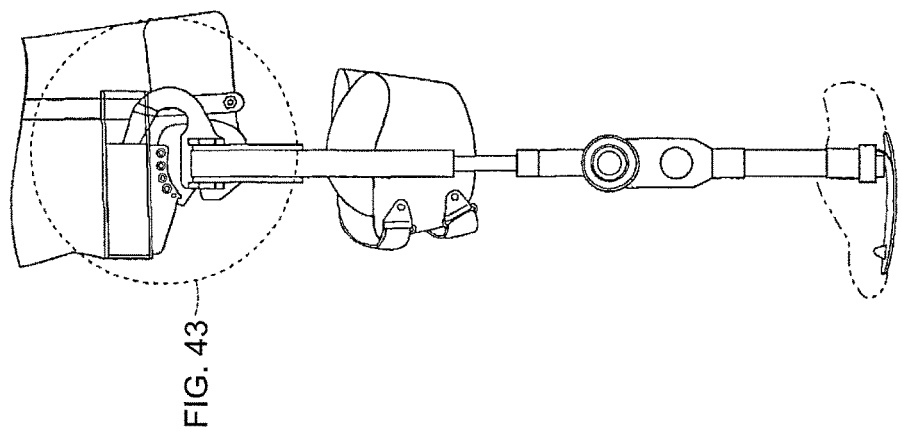
FIGS. 43 and 44 depict a hip structure with a hip spring for storing energy during late hip extension and released as the leg lifts from the ground.
Figure 43:
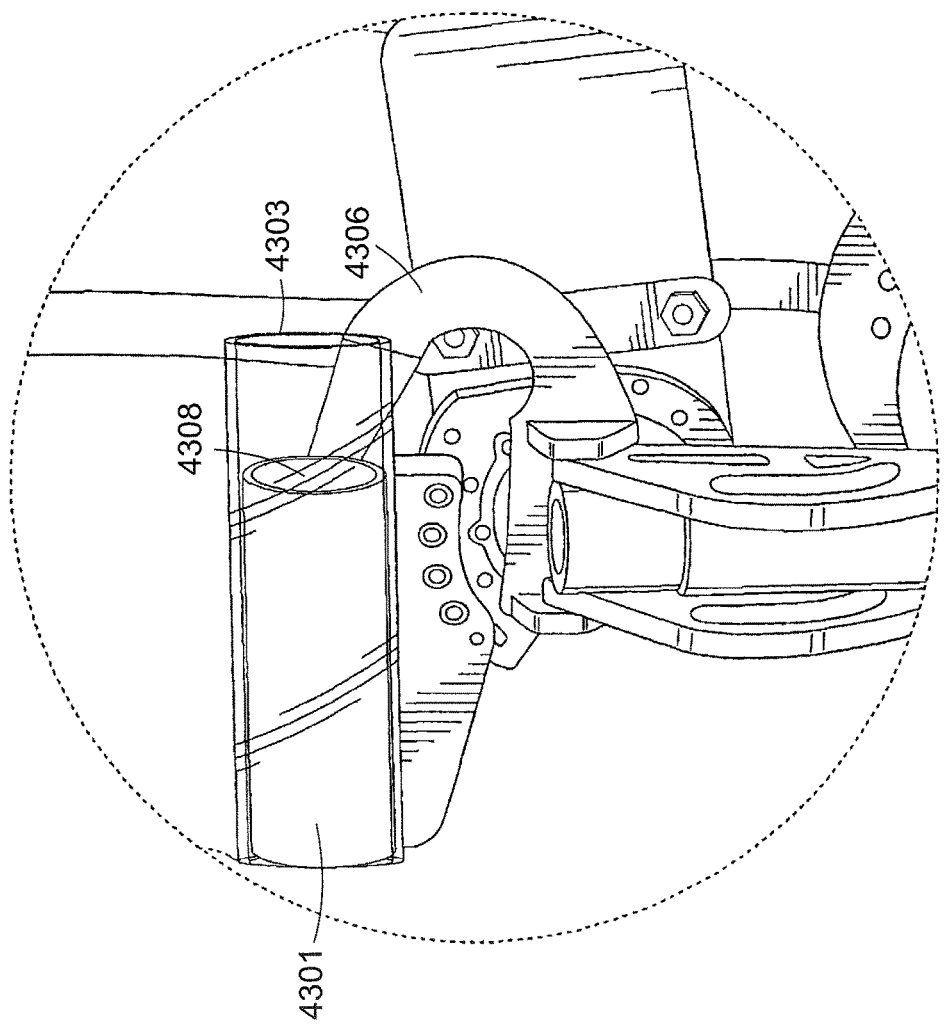

FIGS. 43 and 44 show the manner in which a hip spring inside a spring holder 4301 and a clear finger guard 4303 is compressed by a plunger 4306 that bears against a Delrin plate and retaining ring at 4308. The spring stores energy during late hip extension, and then that stored energy is released to augment rapid hip flexion as the leg lifts from the ground surface.

Motivated by the energy management analysis, a unidirectional hip spring is implemented at the hip joint. The LHC-187R-4-M compression spring from Lee Spring is selected since it has a spring constant of 99 lb/in with 2" travel and a 4" free length. Using this particular spring stiffness, the hip muscular work performed is minimized during late hip extension and early hip flexion (lift-off of leg from ground surface). The plunger can be adjusted to a variety of engagement angles. The clear plastic finger guard is installed for safety.

Figure 45:
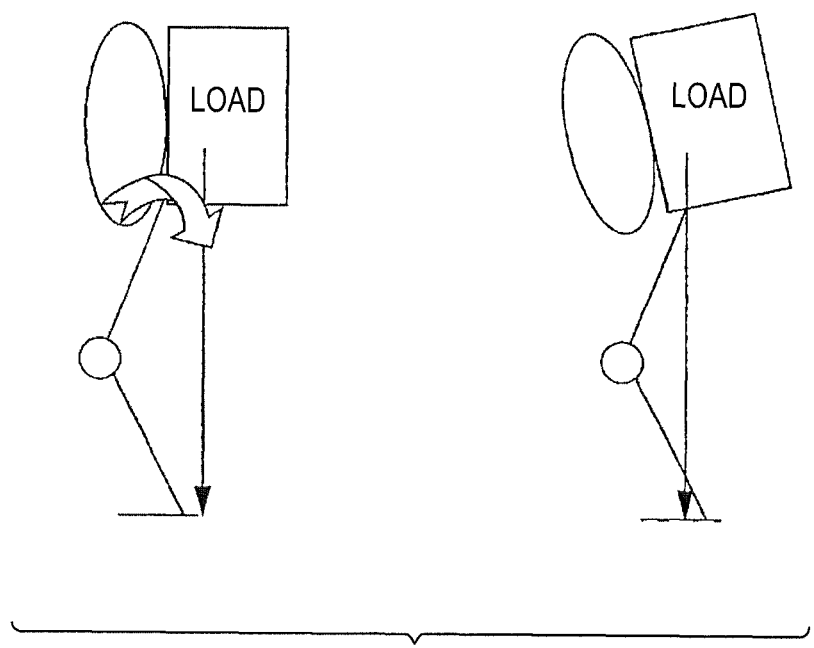
FIG. 45 is a diagram illustrating the moment created by the load during standing.

The exoskeleton wearer cannot stand upright since the backpack load is offset behind the human and creates an overturning moment that could cause the human to fall backwards as shown in the side view of FIG. 45. To counter this moment, the human user can lean forward so that the center of gravity of their upper body is placed over their feet. However, because of the hip extension spring, the human can stand upright. The hip flexion spring creates a counter moment that offsets the overturning backpack moment.

Hip Abduction/Adduction Spring

When the exoskeleton wearer stands on one leg, a moment is created by the backpack load since it is off center from the biological hip joint. The backpack load and the reaction force from the exoskeleton leg cause a moment 4610 about the biological hip center. This moment is undesirable and can cause discomfort. A 250 kN/m abduction spring 4620 is implemented to the hip joint to help counter the backpack moment. The spring is unidirectional, and is compressed as the exoskeleton leg undergoes adduction from a vertical orientation. The spring releases its stored energy to promote hip abduction from a maximally adducted state during level ground walking. The design is shown in FIGS. 46A-B.

During slow human walking, the knee behaves largely as a variable damper where minimal positive power is exerted. The knee of the exoskeleton is implemented with a magnetorheological damper with the fluid in the shear mode. The damper at the knee can exert a maximum braking torque of 60 Nm and consumes on average approximately 1 W of electrical power during level ground walking.

Knee Control is implemented as a virtual damper with applied current proportional to velocity. FIG. 47 shows the variable damper knee of the exoskeleton.

Spring at the Ankle

Figure 48:
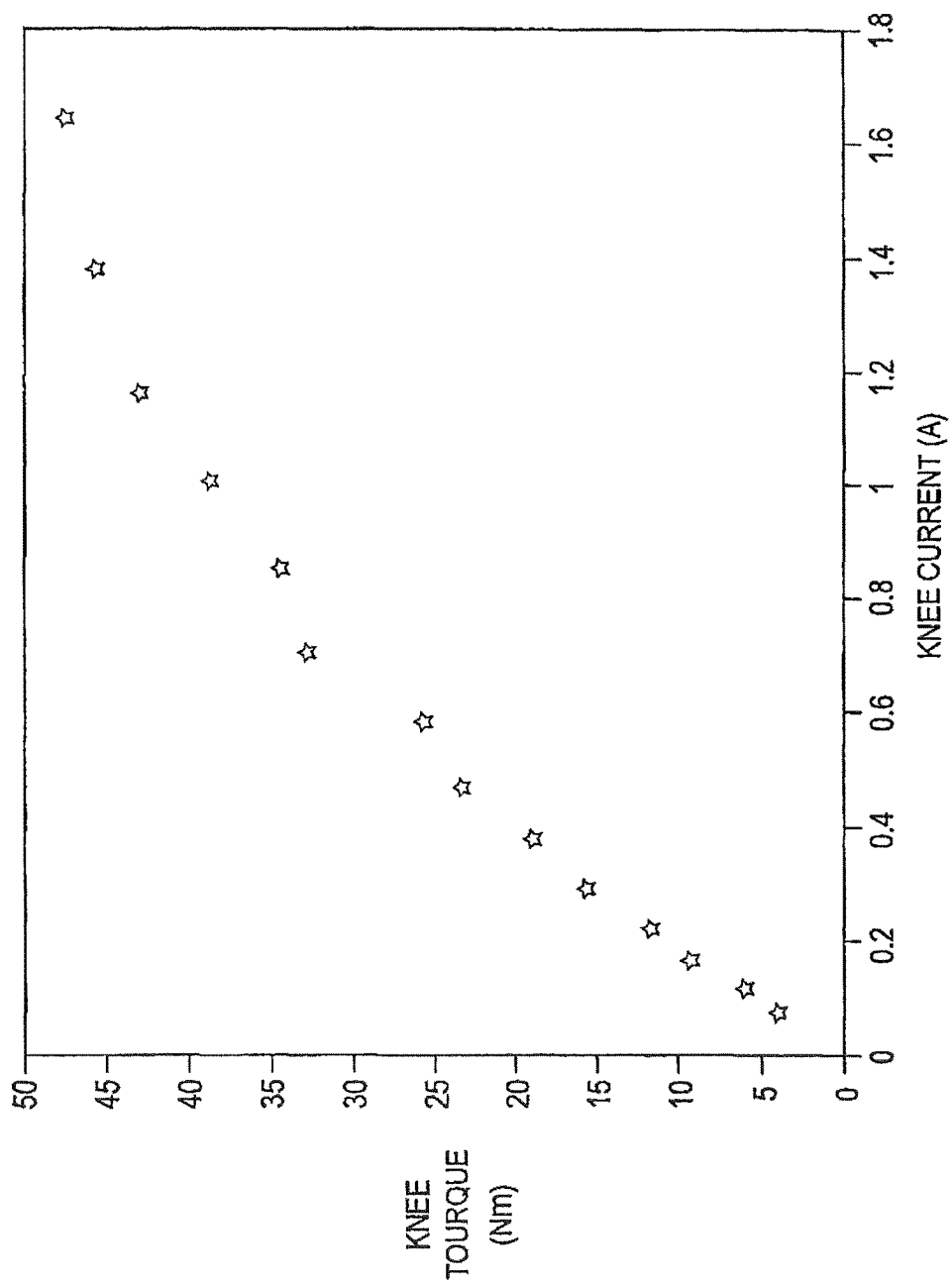
FIG. 48 is a graph of current vs. braking torque for the variable damper used in the knee joint.

For slow walking, it has been shown that the ankle behaves like a spring where ankle torque correlates with ankle position. For the exoskeleton, a spring located at the ankle joint is designed to store elastic energy during controlled dorsiflexion. This energy is subsequently released to assist the exoskeleton foot in plantar flexion as the foot comes off the ground. FIG. 48 shows the relationship between applied knee current and knee braking torque.

Exoskeleton Ankle Design for Exoskeleton Foot in Parallel with Human Foot

Figure 49:
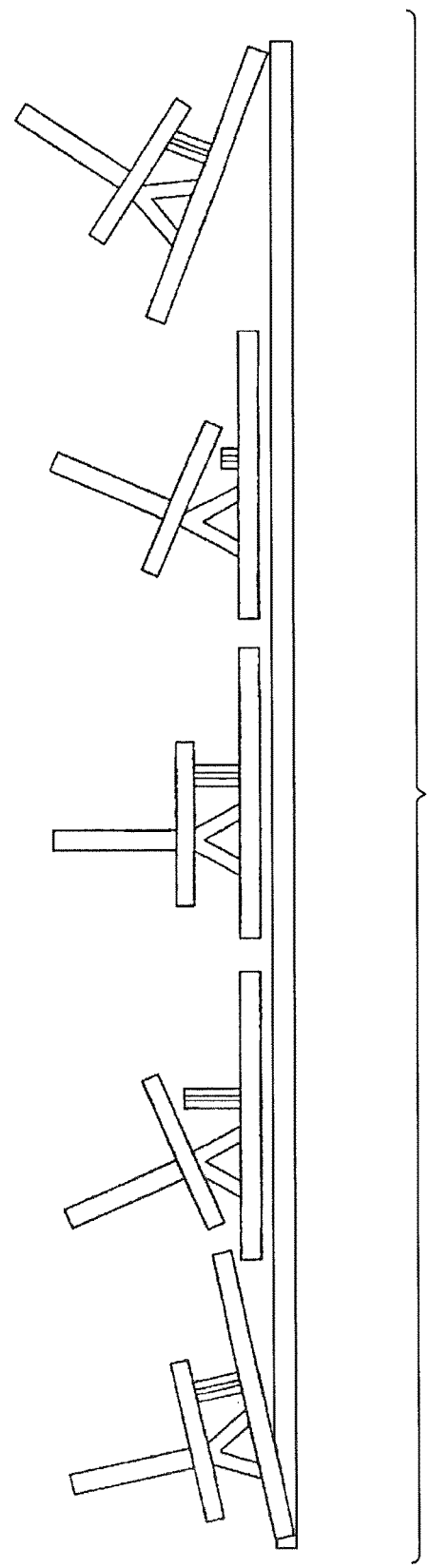
FIG. 49 is an illustration showing how energy is stored and released by the ankle spring.

One method of implementing a rotary ankle spring is by having a lever compress a linear urethane spring. FIG. 49 and FIG. 36 (discussed above) depict the concept. One could also add another spring on the other side of the lever to store energy in controlled plantar flexion.

Exoskeleton Ankle Design for Foot Integrated into Boot or Shoe

Figure 50:
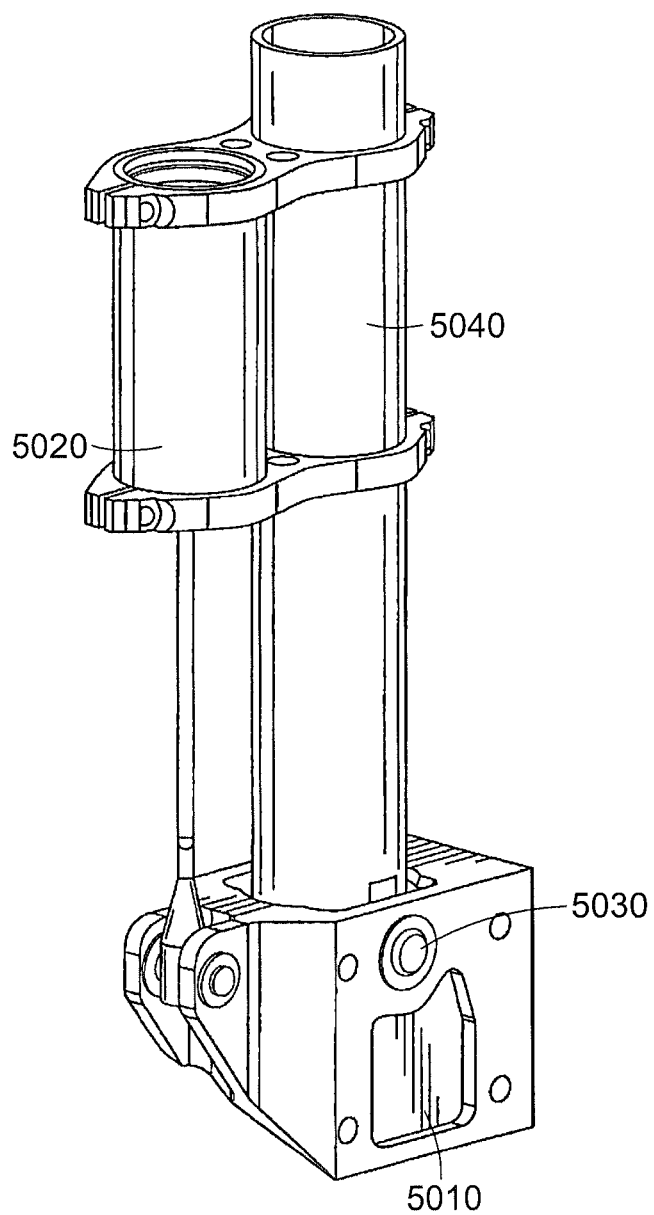
FIG. 50 is a perspective view illustrating the exoskeleton ankle design for the integrated exoskeleton and shoe.

The exoskeleton ankle design shown in FIG. 50 attaches to a carbon fiber mounting plate 5010 such as that shown earlier in FIG. 37. In the previous exoskeleton foot design, shown in FIG. 36, an elastomeric bumper spring is placed at the ankle to store energy during controlled dorsiflexion and then to release that energy to assist powered plantar flexion. The ankle design shown in FIG. 50 works in a similar manner, except that two springs are used instead of one (one for controlled plantar flexion and one for dorsiflexion). Both springs are placed in the spring holder 5020 shown in FIG. 50. The lightweight rod compresses the appropriate spring during the stance period of a walking cycle. Also depicted in FIG. 50 are collocated ankle joint 5030 and exoskeleton shank 5040.

Figure 51:
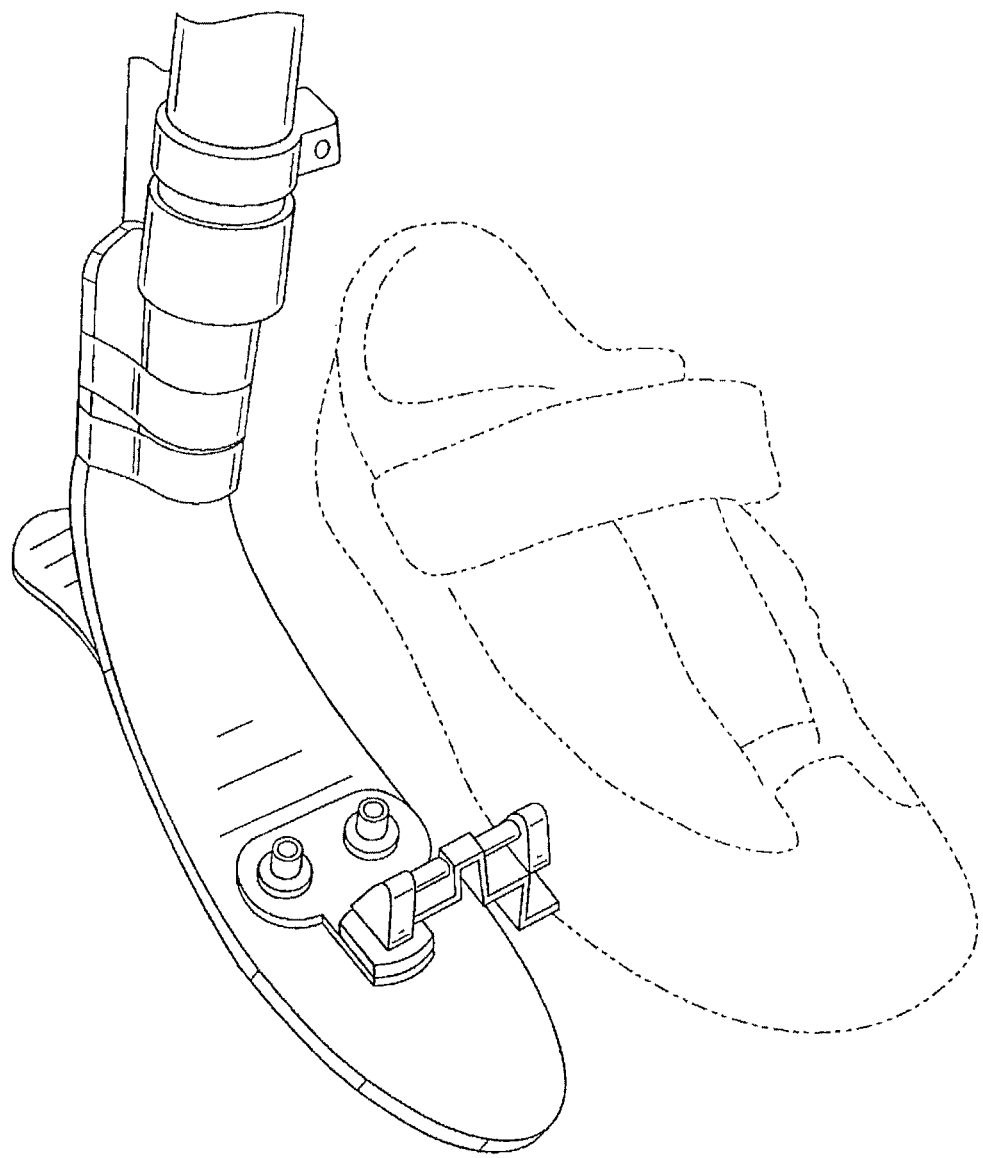
FIG. 51 depicts the bidirectional spring at the ankle.

A second approach for a bi-directional spring design is shown in FIG. 51. Here a carbon composite ankle-foot structure is positioned on the lateral side of the human foot. During a walking stance period, energy is stored in a heel spring during controlled plantar flexion, and then an ankle leaf spring stores energy during controlled dorsiflexion. Finally, these stored energies are released to augment powered plantar flexion.

Bi-Articular Mechanism

With an actuator at the hip of the exoskeleton, it is possible to transfer that energy down to the ankle via a bi-articular mechanism. An external, bi-articular transfemoral prosthesis, robotic limb, or orthotic brace is shown in a heel strike to toe-off walking sequence. The system comprises above-knee segment 5205, knee joint 5210, ankle joint 5215, posterior knee pivot 5220, posterior clutch 5225, posterior spring 5230, posterior cord 5235, knee-ankle transfer clutch 5240, anterior pivot 5245, anterior clutch 5250, anterior spring 5255, and anterior cord 5260, as seen in FIGS. 52A-G. The system of springs and clutches (or variable-dampers) allows for normal knee and ankle motions throughout the stance period of walking, including early stance knee flexion (FIGS. 52A-C) and ankle controlled plantar-flexion (FIGS. 52A-B), controlled dorsi-flexion (FIGS. 52B-E) and powered plantar flexion (FIGS. 52E-G). For posterior and anterior clutches 5225, 5250, and knee-ankle transfer clutch 5240, the clutch state is designated by an open or closed symbol. Closed symbols represent an engaged or locked clutch state, while open symbols represent a disengaged or unlocked state. For example, during late stance knee flexion (FIGS. 52F-G), anterior clutch 5250 is in the disengaged state and therefore is designated by with an open symbol. For this combination of series-elastic, variable-clutch or damping mechanisms, hip extension work causes the knee to extend and to elongate an artificial Achilles tendon spring 5230 and then that stored energy augments powered planter flexion.

If a clutch is implemented as a variable-damper, a sufficient amount of damping is applied such that the series spring is adequately engaged. A distinct advantage of the variable damper implementation compared with a binary locking or unlocking mechanism, is that energy can be dissipated from the spring if that energy is deemed unnecessary. For example, if energy is stored during a walking step but a leg prosthesis user wishes to stop walking, energy stored in the spring can be dissipated as heat via the series variable damper.

Controller Implementation

The above-noted U.S. patent application Ser. No. 11/499,853, entitled "Biomimetic motion and balance controllers for use in prosthetics, orthotics and robotics", filed on Aug. 4, 2006, the disclosure of which is incorporated herein by references, describes four different embodiments of motion controllers which operate in real time. These motion controllers are provide postural stability by employing biomechanically inspired optimization strategies in which joint angle trajectories are varied to achieve whole-body postural balance. The above-noted application Ser. No. 11/499,853 presents several embodiments of biomimetic motion and balance controllers that may be used to provide postural balance to an exoskeleton during walking.

As described below, the exoskeleton may be controlled by reading various sensor values into a central computer mounted on the exoskeleton. Based on these sensor values the appropriate actuation is applied at the hip series elastic actuator and knee variable-damper. This section outlines the electronics hardware used on the exoskeleton as well as the control strategies at the hip and knee joints.

Electronics Test Bed

The exoskeleton is made autonomous by means of an onboard computer with a data acquisition card, power supply and motor amplifiers. The system is powered by a 48V battery pack. Custom signal conditioning boards amplify sensor readings and provide a differential input to the data acquisition board in order to minimize common mode noise from pick-up in the system. A custom breakout board is designed that interfaces the sensors to the D/A board on the PC104 as well as providing power to the signal conditioning boards. The amplifiers for the actuator and brake are 48V digital amplifiers from Copley.

Figure 53:
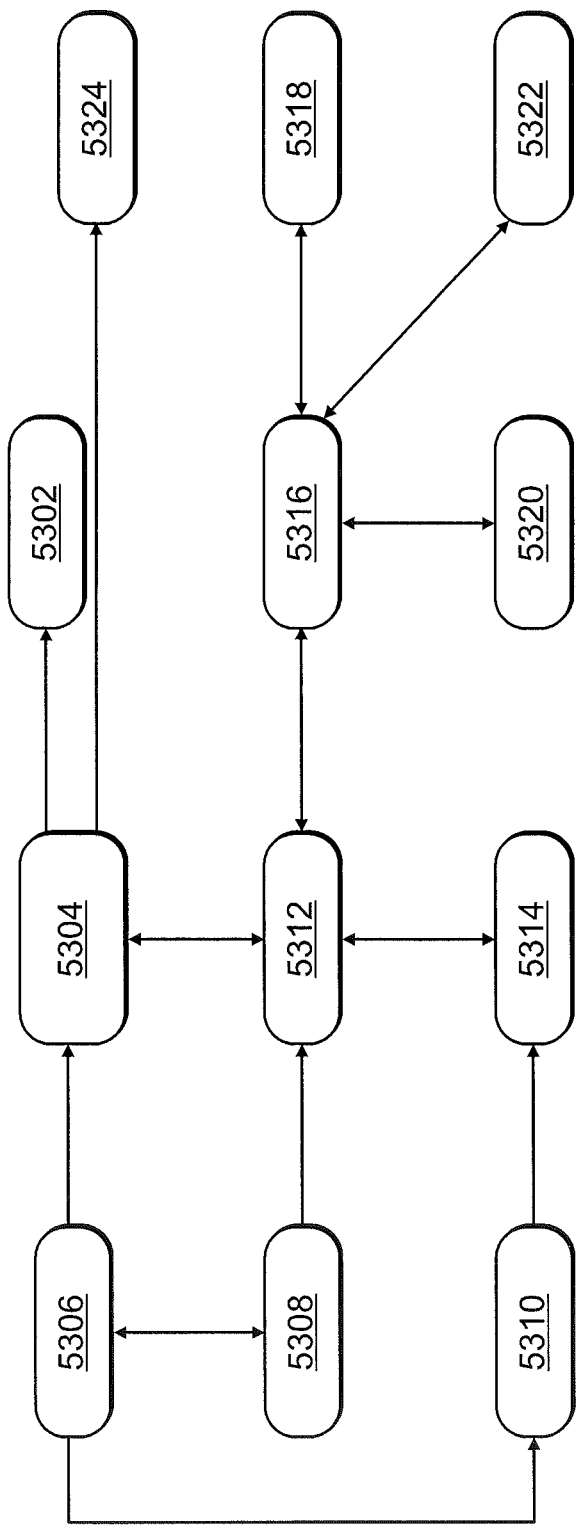
FIG. 53 is a schematic block diagram of the electronic components used to control hip actuators and variable dampers at the knees.

FIG. 53 is a schematic of the electronic components. The system consists of two actuators at the hips and two variable-dampers at the knee but only one of each is shown here for clarity. As shown in FIG. 53, system 5300 includes: actuator 5302; Copley motor amp 5304; 48v battery pack 5306; 48v>+−12v DC/DC 5308; 48v>5V DC/DC 5310; break out board 5312; PC104 A/D and D/A 5314; instrumentation 5316; actuator potentiometers 5318; joint potentiometers 5320; shank strain gauge 5322 and brakes 5324.

PC 104 and Data Acquisition

The PC used is a MICROSPCACE PC/104 from Digital Logic. It is a miniature modular device that incorporates most of the major elements of a PC compatible computer in a small form factor. It is powered with a PENTIUM III 700 MHz processor. A PC/104 format data acquisition board, Diamond-MM-32-AT, from Diamond Systems is connected to the PC/104. It has 32 total analog inputs and 4 analog outputs. The board is configured for 16 differential analog inputs in software and on the board with jumpers.

Matlab xPC Target is used to run the code for real-time control and data acquisition. The Matlab xPC real-time kernel is installed and run on the PC/104 (remote PC) which is attached to the exoskeleton. A desktop or laptop computer is then used to create a model in Simulink. xPC Target lets you add I/O blocks to your model and then use the host PC with Real-Time Workshop and a C/C++ compiler to create executable code. The executable code is downloaded from the host PC to the target PC via TCP/IP. After downloading the executable code, one can run and test your target application in real time. Data is recorded by using the xPC host scopes in the simulink model. After running the experiment the host pc is connected to the target pc to download the data.

Actuator Amplifier Boards

The amplifiers used in the system are general purpose digital servo amplifiers from Copley Controls. They can be used in brushed and brushless mode and offer current, position and velocity control modes (the latter two based on encoder input from the motor to the amplifier). For controlling the series elastic actuators, the Accelus model ASP-090-18 is used. It is rated for a continuous current of 6 Amps and a peak current of 18 Amps. This is chosen based on the fact that the continuous current for the RE40 motor used is 3.33 Amps. The Accelnet Micro Module is used to control the knee brake and is similar to the Accelus but it comes in a PCB mount version that has a much smaller form factor. A custom PCB breakout board is fabricated that interfaces to the Accelnet. The amplifiers are programmed via RS232 using the CME 2™ software from Copley.

After entering the motor specifications into the software the current loop P and I control gains are determined by using the current loop Auto-Tune feature in the software. The continuous and peak current limits are entered in the software and act as a good safety feature when tuning up the actuators in the early stages. The amplifier control parameters are then saved in flash memory and the RS232 connection can be terminated.

Signal Conditioning

The sensors on the exoskeleton are read into the computer as analog voltage signals. Due to relatively long connection cables there is a lot of noise pick-up from the amplifiers, motors and brake. In order achieve a good signal to noise ratio the sensor raw voltage readings are amplified with a differential line driver and the signal is also sent through an analog low pass filter with a cut off at 1.5 kHz.

Sensing

Figure 54:
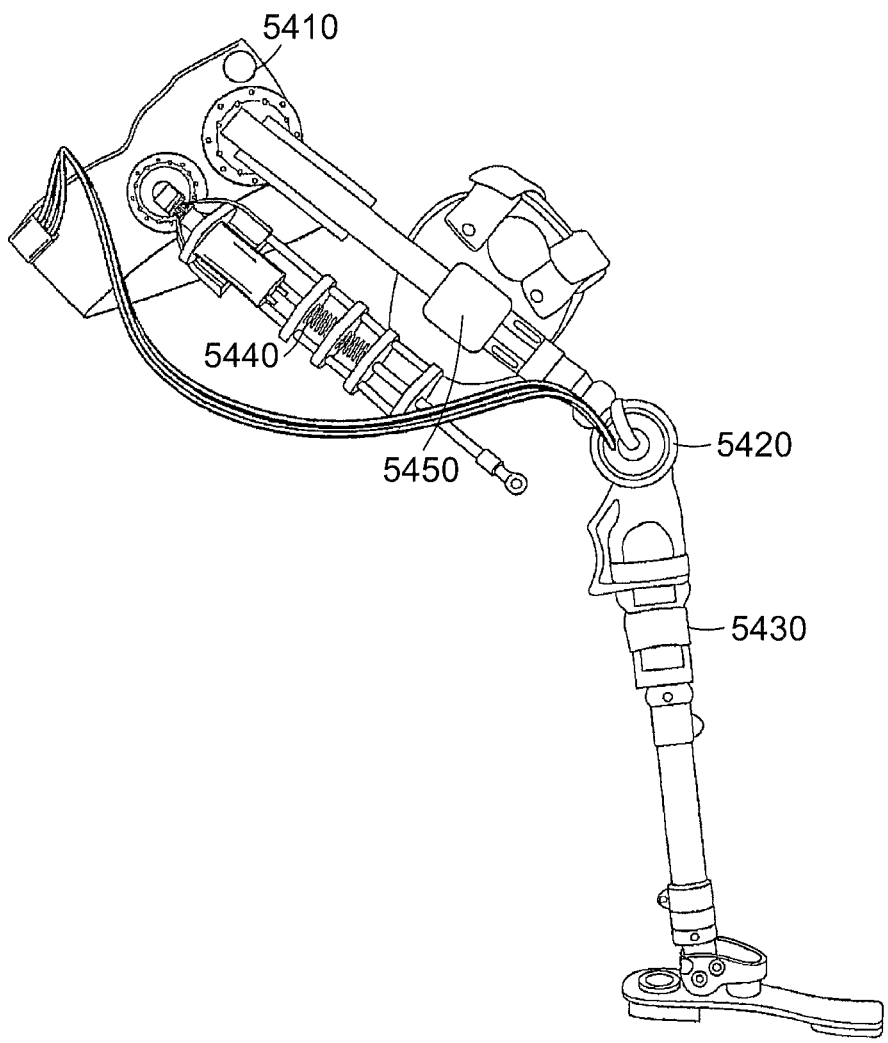
FIG. 54 illustrates the location of sensors on an exoskeleton leg.

The exoskeleton is instrumented with sensors in order to detect state transitions for real time control of actuation at the hip and knee, as seen in FIG. 54. The sensors also facilitate analysis of the kinematics and kinetics of gait of the exoskeleton as a function of gait cycle. The angle of the hip (thigh relative to pelvic harness) and the knee (shank relative to the thigh) are measured using rotary hip 5410 and knee 5420 potentiometers. Strain gauges 5430 on the structure of the exoskeleton shank measure the bending moment of the shank as well as the vertical force borne by exoskeleton leg. Also used are SEA spring potentiometer 5440 and thigh cuff force sensor 5450.

Angle Sensing

The angle of the hip (thigh relative to pelvic harness) and the knee (shank relative to the thigh) are measured using rotary potentiometers. The signals from these potentiometers are amplified and filtered using the signal conditioning board in potentiometer configuration with a gain of 1.

Hip Torque Measurements

The hip torque produced by the actuator can be measured by means of measuring the deflection of the spring pack of the series elastic actuator. This is the force that is used for the closed loop control of the actuator and by multiplying the force by the moment arm of the actuator the torque at the hip joint can be calculated.

Ground—Exoskeleton Interaction Sensing

Figure 55:
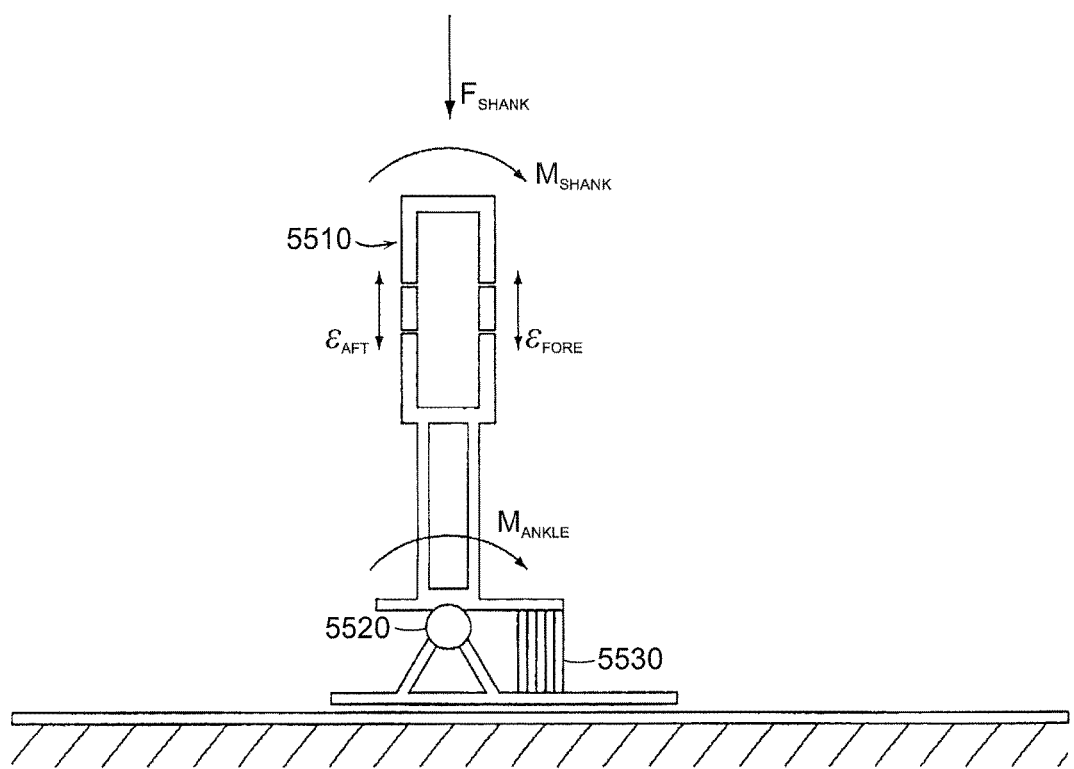
FIG. 55 is a schematic depiction of the exoskeleton shank and foot.

Strain gauges placed in the structure of the exoskeleton shank are used to measure the bending moment $M_{SHANK}$ of the shank as well as the vertical force $F_{SHANK}$ in the exoskeleton leg, as illustrated in FIG. 55. The signals from the strain gauges are amplified and filtered using the POT4 board in the strain gauge configuration with a gain of 500. The moment in the shank is calculated by subtracting the signals from the two strain gauge bridges 5510 and the vertical load by adding the two signals. Also shown in FIG. 55 are ankle joint 5520 and urethane spring 5530.

Human—Exoskeleton Interaction Sensing

Figure 56:
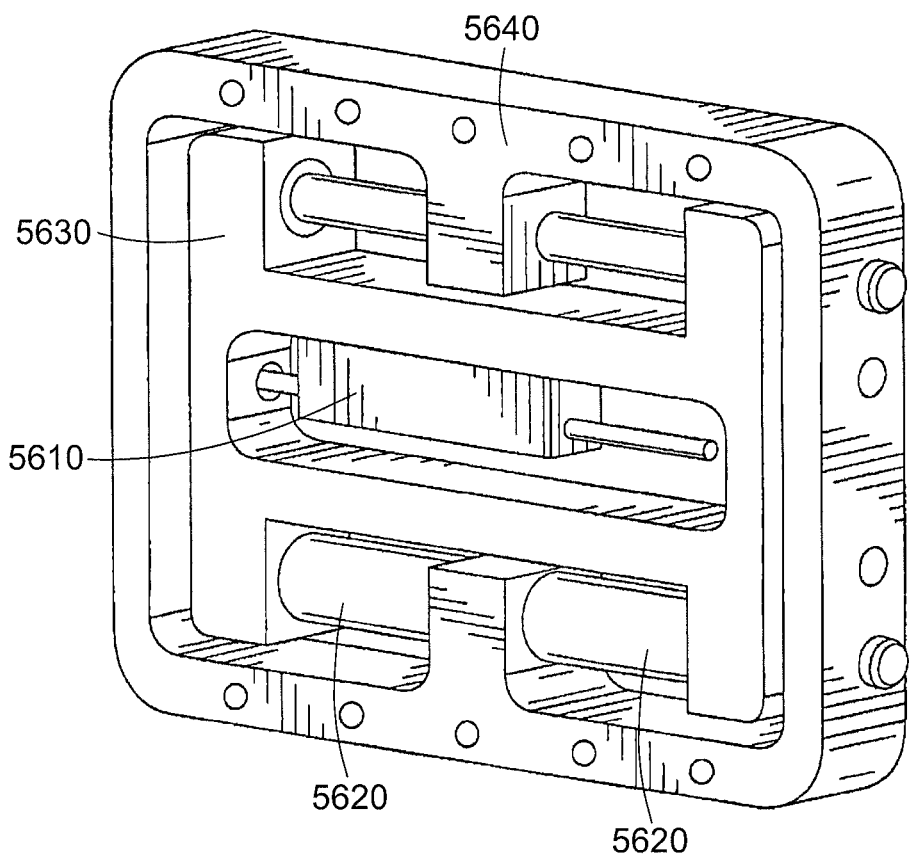
FIG. 56 depicts the thigh cuff sensor for measuring the force between the exoskeleton and the human thigh.

For the purpose of measuring the interaction force between the human thigh and exoskeleton leg a custom sensor is built. The sensor consists of a spring pack and the deflection of the springs is measured with a spring-loaded linear potentiometer 5610, as shown in FIG. 56. The device consists of die springs 5620 that are compressed due to relative movement of the two metal parts (one 5630 attached to the exoskeleton leg and one 5640 the human leg via a thigh cuff) and the displacement is measured with a linear potentiometer thus giving a reading of the force. This particular design is cheaper and more robust than a load cell.

One reason for knowing the force at the thigh is that a control strategy could be implemented where by a motor at the hip could servo the exoskeleton to zero the force at the thigh. This would effectively make the exoskeleton get out of the way of the wearer. Another reason for measuring the interaction force at the thigh is to estimate the power transfer between the exoskeleton and the wearer. The velocity at the thigh could be calculated by knowing the velocity of the hip.

Control Strategies

Figure 57:
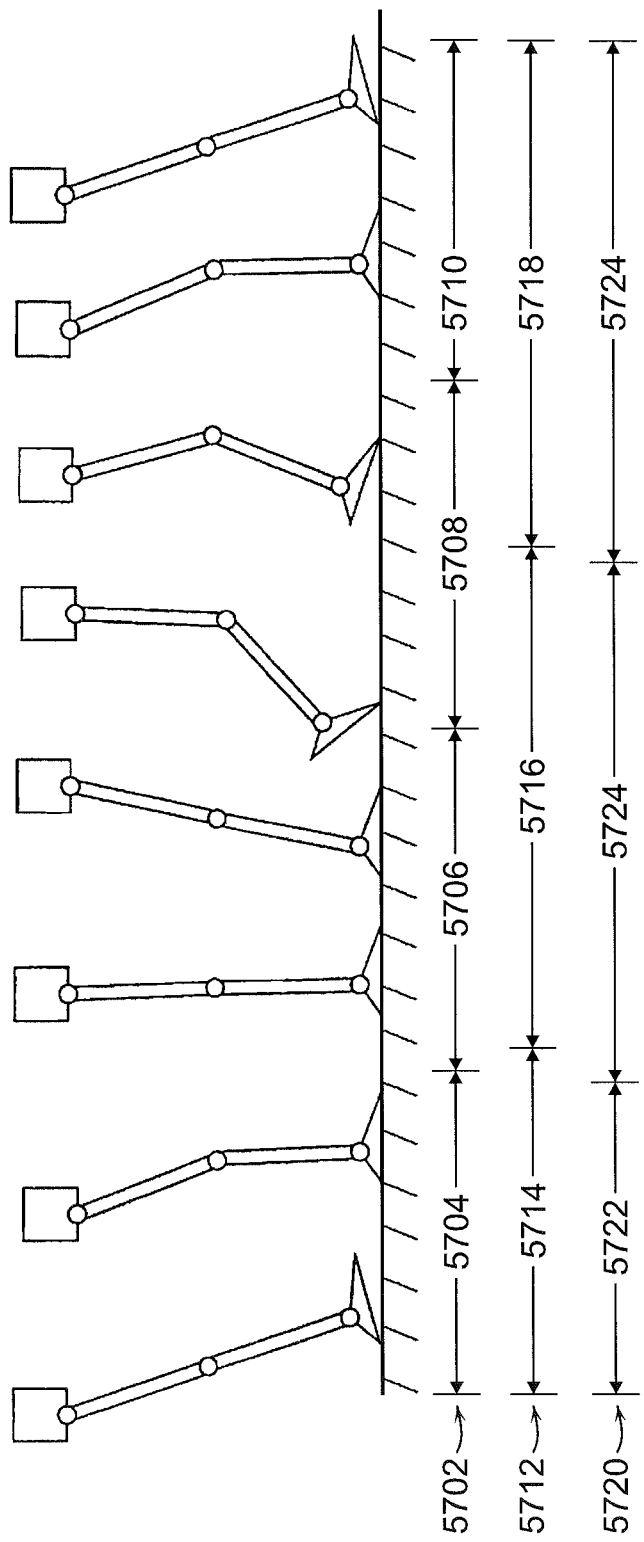
FIG. 57 is a diagram that summarizes the actuation control of the hip and knee during the gait cycle, as well as the operation of the ankle spring.

The controller for the exoskeleton is required to perform actuation at the hip and knee based on knowledge of the current phase of gait. A state machine control strategy is implemented based on angle and force sensory readings from the exoskeleton. Human walking kinematic and kinetic data motivated the actuation to be commanded in the individual states. FIG. 57 outlines the desired actuation as a function of gait cycle at: hip 5702, namely thrust 5704, extension spring 5706, swing assist 5708, and leg retraction 5710; knee 5712, namely knee on 5714, demagnetize knee 5716, and knee off 5718; and ankle 5720, namely ankle free 5722, spring compression and release 5724 and ankle free 5726.

(1) Hip

For the Thrust phase, the actuator at the hip exerts a torque to help raise the center of mass of the exoskeleton. During the next phase, Extension Spring, a virtual spring stiffness is programmed that is compressed as the center of mass of the exoskeleton moves forward. As the leg changes direction the Swing Assist phase is entered where the energy is released from the virtual spring, and a torque is applied to assist in swinging the leg forward. Leg Retraction is entered after full hip flexion, and a torque is applied to assist in foot placement and weight acceptance.

(2) Knee

Knee On occurs at heel strike, and the damper is programmed to exert a torque proportional to the rotational velocity of the knee joint. Two different gains are used, depending on the velocity sign, to control knee rotation for knee flexion and extension. After the knee is turned off, there is a residual magnetic field and hence a resistive torque. The knee is demagnetized when the knee joint remains locked at full extension during the late stance phase. After this phase, the damper is turned off throughout the entire swing phase.

Knee Controller

Figure 58:
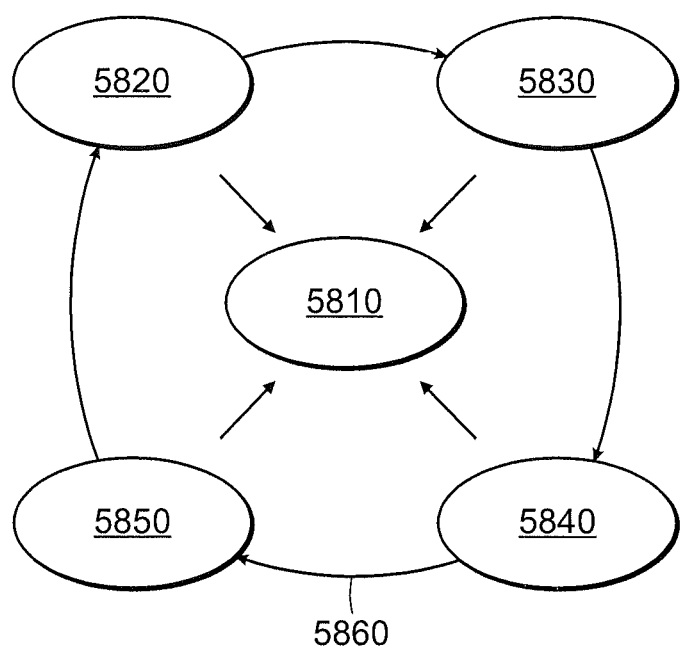
FIG. 58 is a state machine diagram of the knee controller.

The state-machine controller for the knee processes knee angle and the force and moment in the exoskeleton leg to define four stages of the walking cycle. FIG. 58 shows the states and the triggers used to switch between states. An off state is implemented so that any time the leg is raised off the ground the brake will turn off allowing the knee to bend freely.

The following table specifies the states and their respective triggers for the state-machine of the knee controller:

| State | Description | Trigger |
|---|---|---|
| 0 | Not walking and leg is unloaded | Load in exoskeleton leg |
| 1 | Stance Flexion and Extension | Load in exoskeleton leg |
| 2 | Pre-swing | Knee angle and moment in exoskeleton leg |
| 3 | Swing Flexion | Load in exoskeleton leg |
| 4 | Swing Extension | Knee angle |

Figure 59:
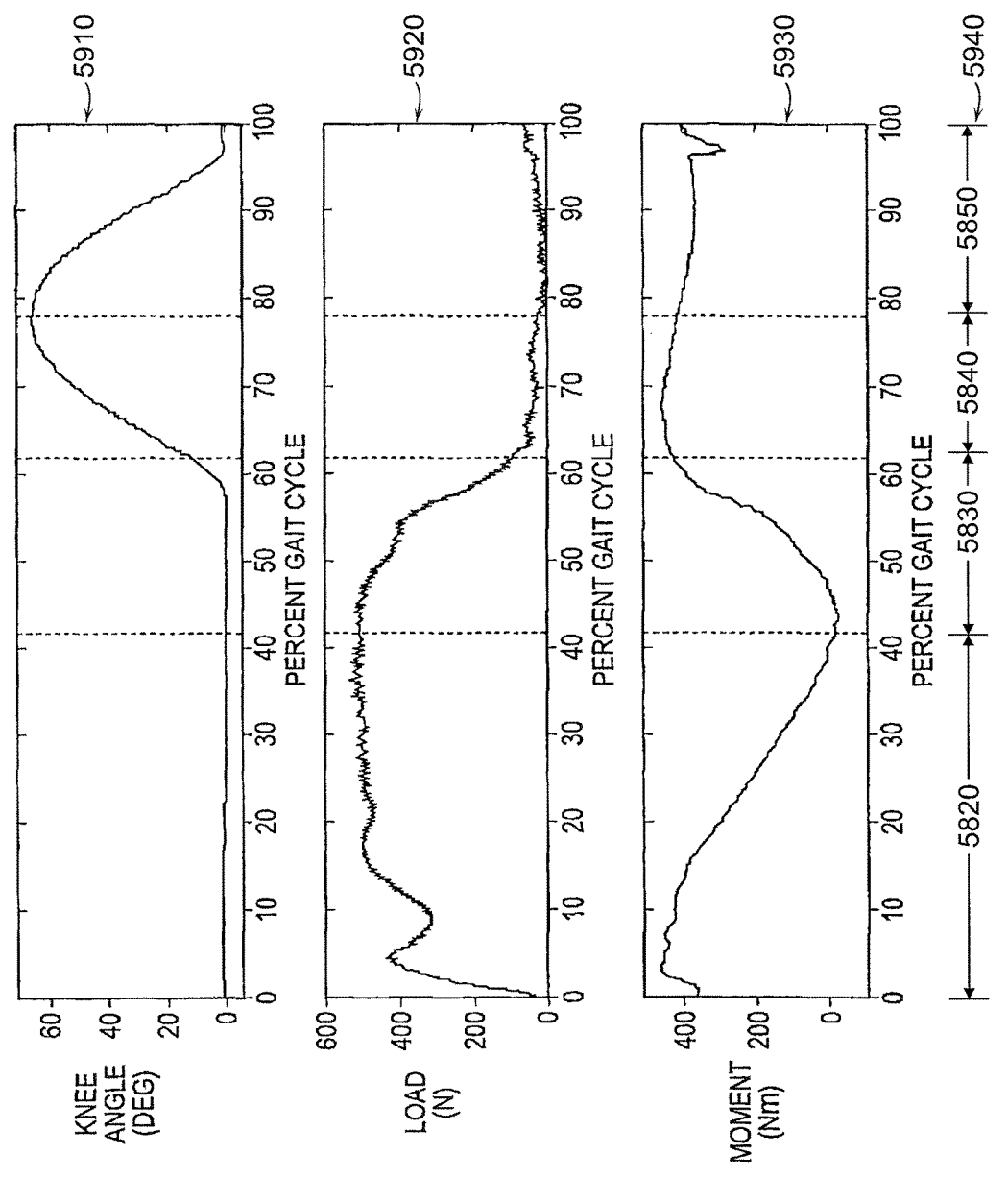
FIG. 59 shows the sensor data for the exoskeleton during a single gait cycle.

FIG. 58 is a state machine diagram for the knee controller, showing state 0 ("off") 5810, state 1 ("Stance Flexion and Extension") 5820, state 2 ("Pre-swing") 5830, state 3 ("Swing Flexion") 5840, and state 4 ("Swing Extension") 5850. Maximum knee angle 5860 is between swing flexion 5840 and swing extension 5850. FIG. 59 shows the sensor data for knee angle 5910, load 5920, and moment 5930 in the exoskeleton shank for a single gait cycle. The states 5940 of the controller are also shown.

For steady state walking, the state machine cycles through states 1 to 4 above. If a person is no longer walking but shuffling or turning around, the controller goes back and forth between state zero, where the leg is off the ground, and state one, where the leg is on the ground.

Figure 60:
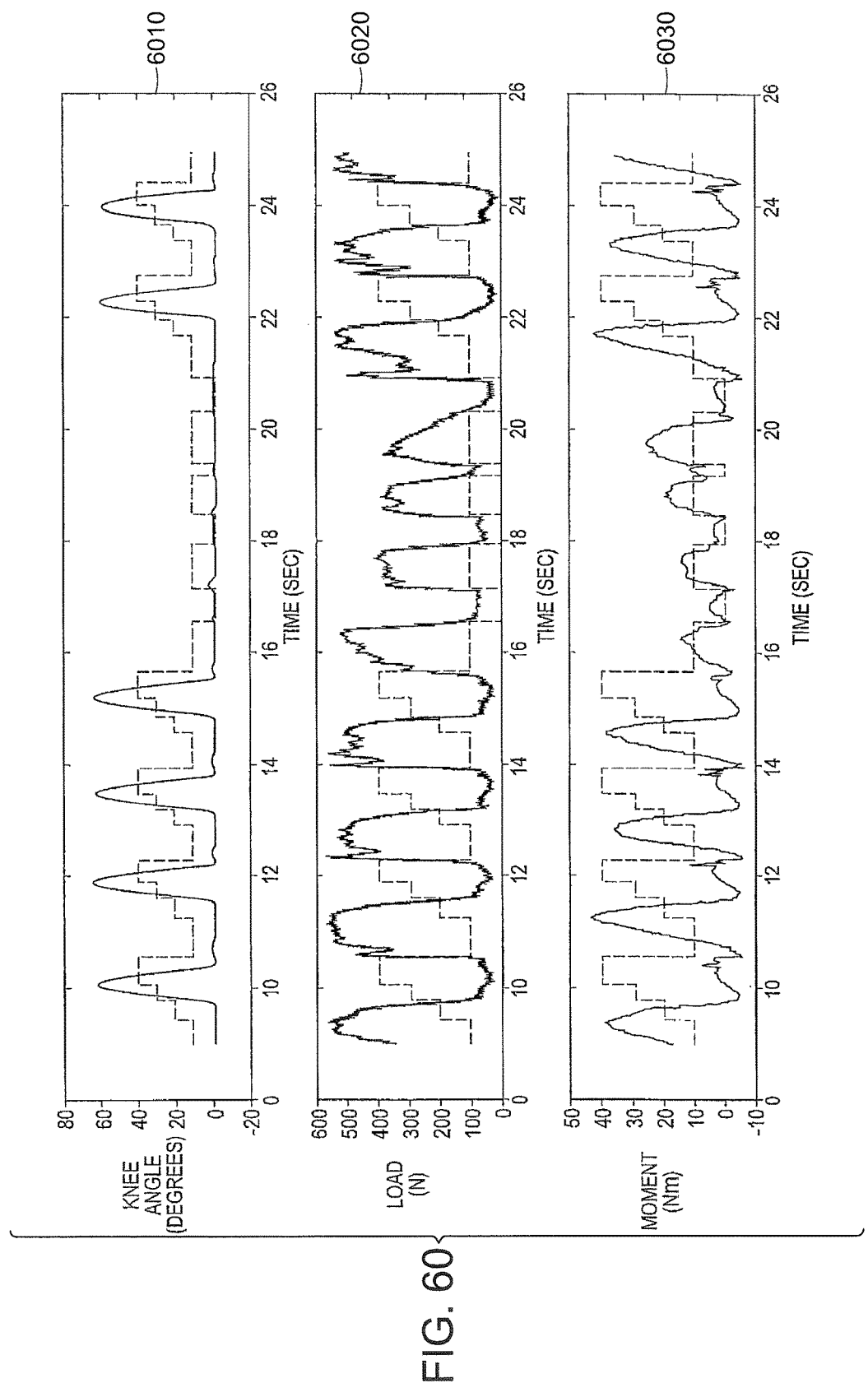
FIG. 60 shows the sensor data for the exoskeleton during walking.

FIG. 60 depicts sensor data for knee angle 6010, load 6020, and moment 6030 for the exoskeleton knee in operation. The data shows a person walking normally, then shuffling as he turns around, and then walking once again.

Hip Controller

Figure 61:
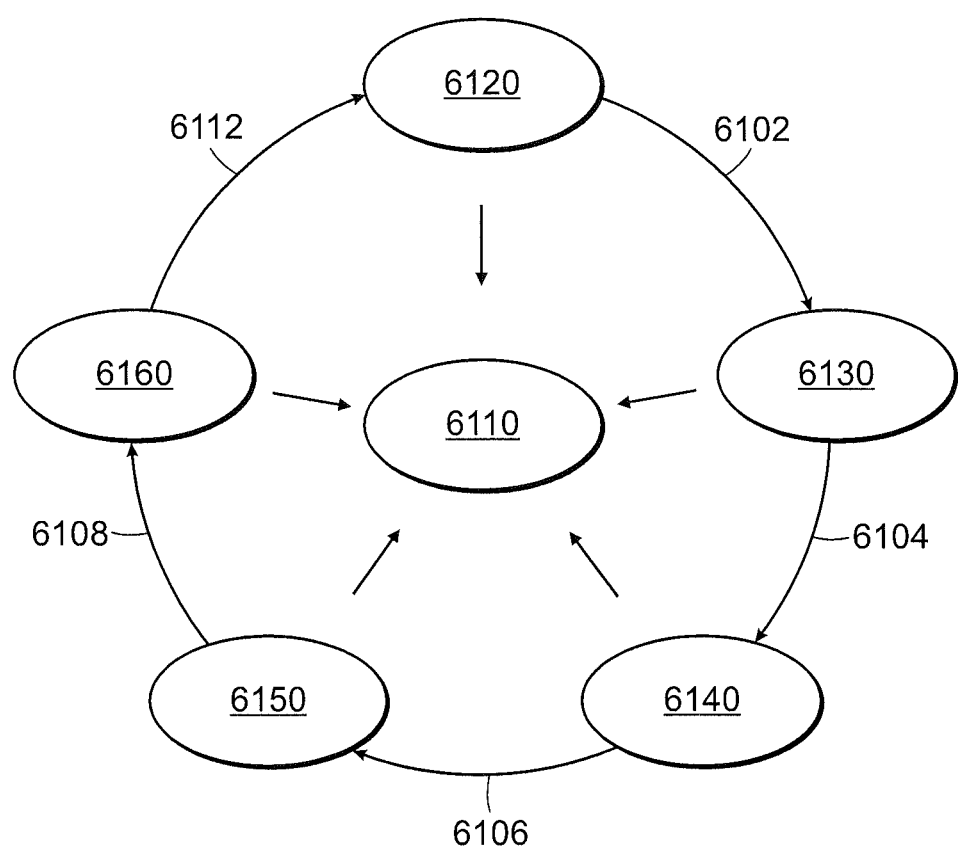
FIG. 61 is a state machine diagram for the hip controller.

The state-machine controller for the hip uses the hip angle and the force in the exoskeleton leg to define five stages of the walking cycle. FIG. 61 illustrates these states as well as the triggers used to switch between states. State 1 is late stance extension as this is deemed to be the most repeatable trigger to determine if the wearer has started walking.

The following table specifies the states and their respective triggers for the hip controller:

| State | Description | Trigger |
|---|---|---|
| 0 | Not Walking | Timeout |
| 1 | Late Stance Extension | Negative velocity when angle is less than zero |
| 2 | Early Swing Flexion | Change in sign of velocity |
| 3 | Late Swing Flexion | Angle is greater than some threshold |
| 4 | Late Swing Flexion | Change in sign of velocity |
| 5 | Early Stance Extension | Force threshold in leg |

FIG. 61 shows the operation of the state machine controller for the hip, showing state 0 ("not walking") 6110, state 1 ("Late Stance Extension") 6120, state 2 ("Early Swing Flexion g") 6130, state 3 ("Late Swing Flexion") 6140, state 4 ("Late Swing Flexion") 6150, and state 5 ("Early Stance Extension") 6160. The states in the table above are connected and the causality between states is shown as well as the triggers between states. Minimum hip angle 6102 is between late stance extension 6120 and early swing flexion 6130. Angle threshold 6104 is between early swing flexion 6130 and late swing flexion 6140. Maximum hip angle 6106 is between swing flexion 6140 and leg retraction 6150. Leg loaded 6108 is between leg retraction 6150 and early stance extension 6160. Angle threshold 6112 is between early stance extension 6160 and late stance extension 6120.

Figure 62:
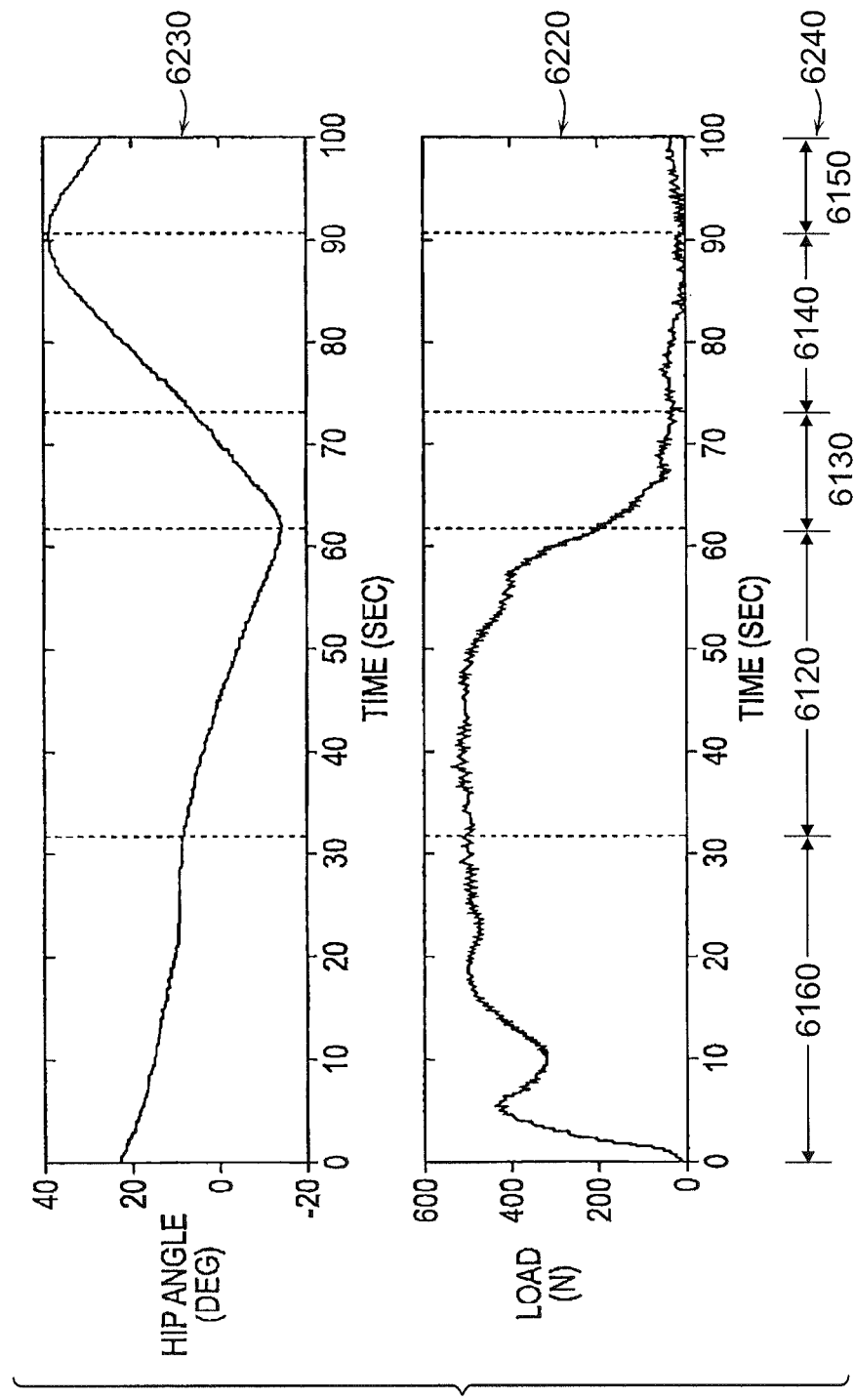
FIG. 62 shows the sensor data from the leg during walking showing hip angle and load.

FIG. 62 shows data for hip angle 6210 and load 6220 in the exoskeleton shank collected from the exoskeleton leg as a function of gait cycle. The states 6240 of the hip controller are superimposed on the plot.

Figure 63:
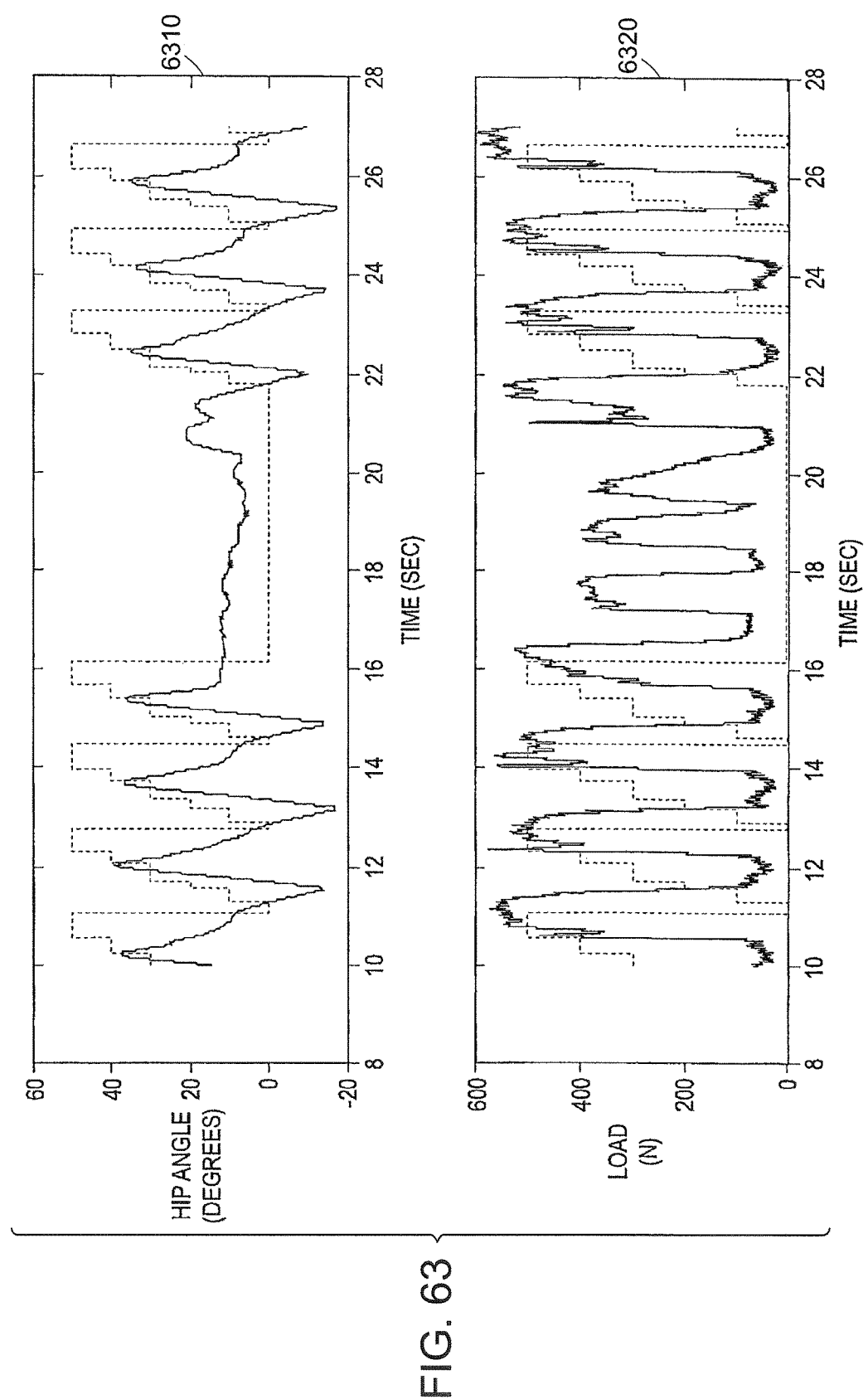
FIG. 63 shows the sensor data for hip angle and load when a person is walking normally.

FIG. 63 depicts sensor data for hip angle 6310 and load 6320 for the hip in operation as a person walks and then stops and shuffles as he turns around and then begins to walk again.

Exoskeleton for Running and Jumping

This section describes the architecture of an exoskeleton that assists humans in running and jumping. It consists of a configuration that places leaf springs in parallel with the human legs. A pelvic girdle or harness transfers the weight of the wearer through the exoskeleton to the ground instead of those forces being borne by the human's legs.

Mechanical Design

The designed mechanism creates natural leg stiffness by means of physical springs parallel to the biological leg. The springs store energy and transfer dynamic loads to the ground and effectively lessen the energy consumption of the biological leg and reduce the metabolic cost of jumping and forward running. One implementation of the mechanism is shown in FIGS. 64A-B, which implementation uses leaf springs parallel to the leg. The most proximal 6410 and distal 6420 aspects of the leaf springs are mounted between the hip and ankle joints, respectively. The damper/clutch device 6430 is located in the vicinity of the knee, but not necessarily mounted on the biological knee.

In FIG. 64A, the foot 6440 is shown on the ground with the clutch or variable damper 6430 locking the knee joint and the leg spring 6410, 6420 fully engaged. In contrast, in FIG. 64B, the foot 6440 is shown off the ground. Here the biological leg is free to flex and extend the knee as the clutch or variable damper 6430 outputs minimal resistance.

Figure 65:
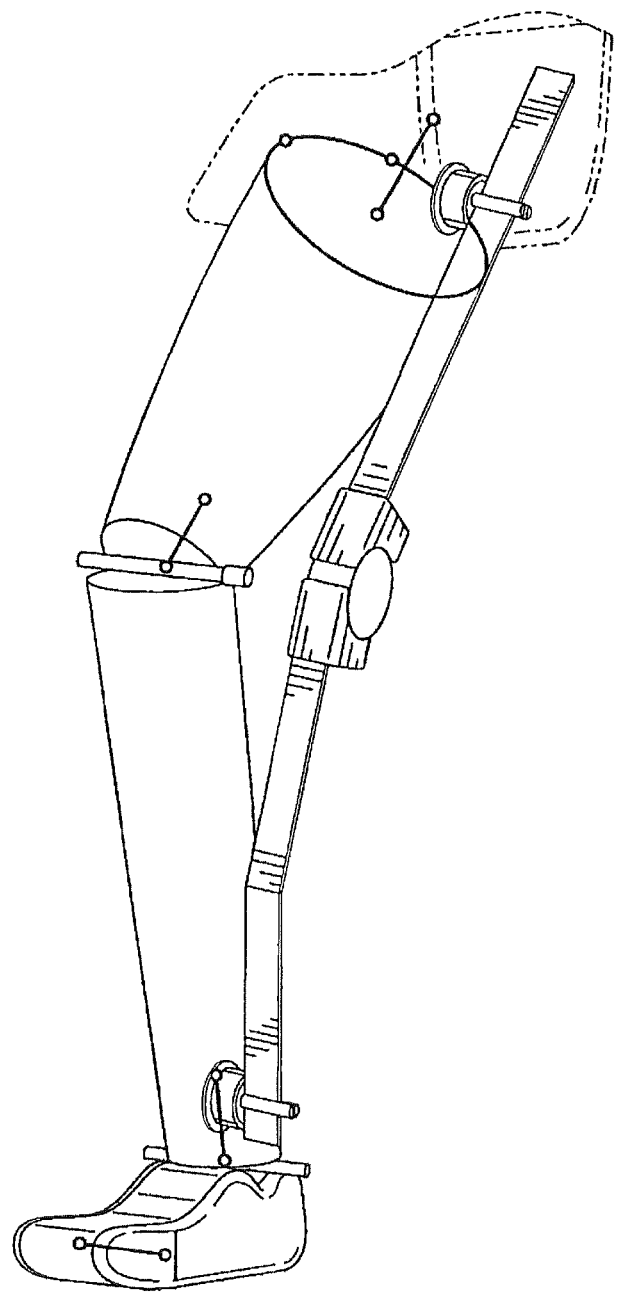
FIG. 65 shows a solid model of the leaf spring architecture.

FIG. 65 shows a solid model of the exoskeleton leaf spring mechanism. The distal aspect of the structure can be mounted above the ankle joint, or to the forefoot region.

Leaf Spring Material

Unidirectional fiber glass barstock, product GC-67-UB, from Gordon Composites, Montrose, Colo. is used as the leaf spring material. A 1.25" width and 0.300" thick spring can support the wearer's weight if his legs go limp, in the sense that the wearer's center of gravity could be suspended about halfway to the ground from its original rest position. Another material that could be used for the leaf spring is carbon fiber composite.

Prototype Exoskeleton

Figure 66:
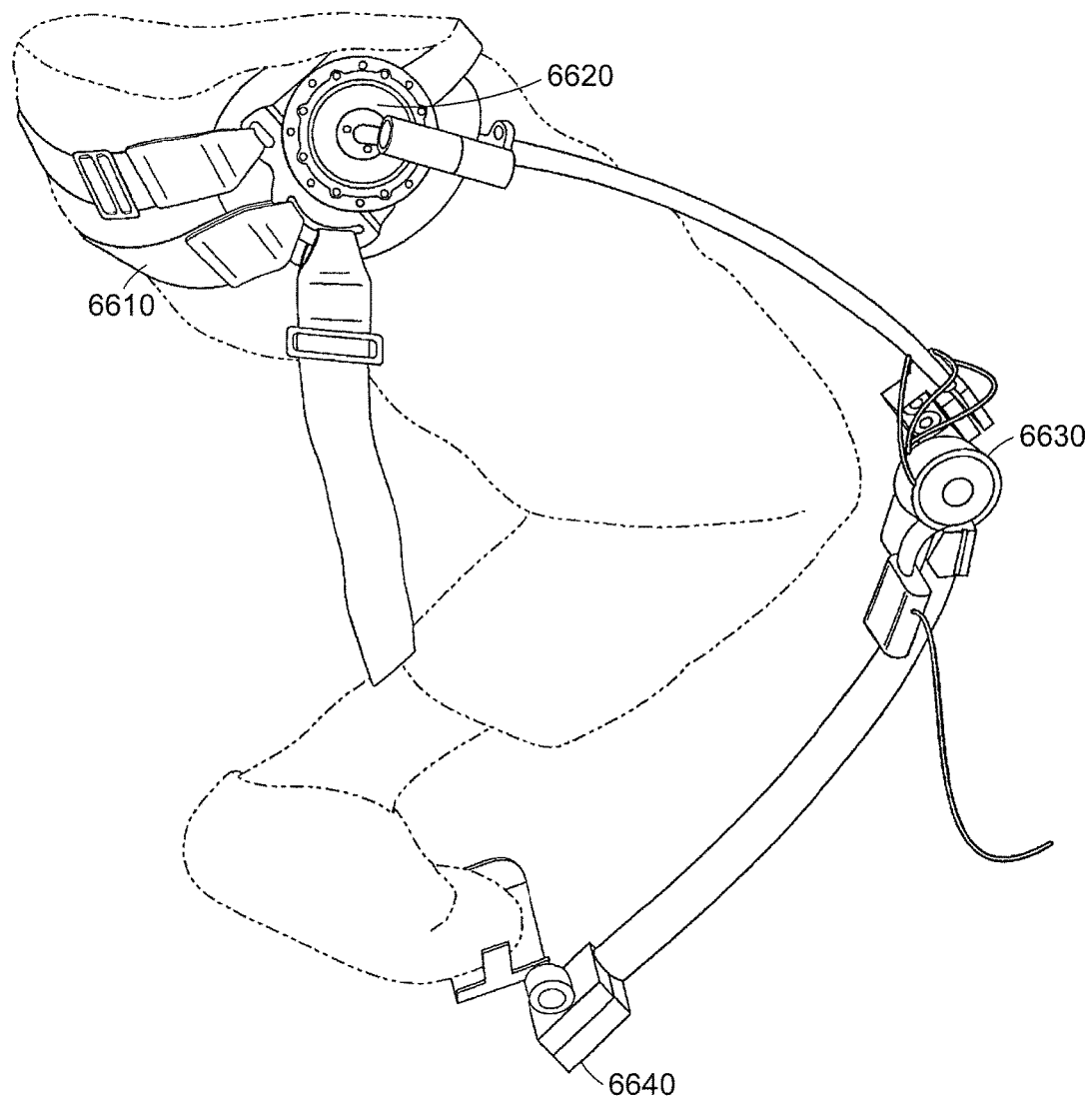
FIG. 66 depicts the parallel leaf spring exoskeleton in a working implementation.

FIG. 66 shows the prototype exoskeleton being worn by a human test subject, including harness 6610, hip joint 6620, clutch 6630, and foot attachment 6640.

Controller Implementation

Force and/or contact sensors are placed under the human foot to detect when the subject's foot is on the ground. A small battery triggers an electromagnet in the clutch that causes the knee to lock or unlock.

While the subject's foot is in contact with the ground during level ground jumping and running, the clutch will lock uni-directionally, allowing knee extension but not knee flexion. This uni-directional control allows the leaf spring to store/release mechanical energy, but still allows the leg to increase in length (knee extension). The ability to extend the knee is important when the leg is shorter in length at first ground contact compared with the leg length when the leg leaves the ground surface. For level ground motion tasks, the damper/clutch device has two fundamental states.

Clutch States Vs. Foot Contact for Level Ground Activities.

For slope descent, the damping response when the leg is in contact with the ground would be relatively lower for knee flexion so that elastic strain energy is not stored in the leaf springs but rather is dissipated as heat via the variable-damper knees.

It is noted here that instead of employing a clutch or variable-damper at the exoskeleton knee, a passive, weight-activated knee unit could be used. Here the knee automatically locks upon knee compression loading and unlocks when compression forces are no longer borne by the knee unit. Such weight activated knee units have been useful in prosthetics and orthotics, and are sold commercially throughout the world.

Finally, it is noted that the knee design might include additional elements such as a motor that would assist the human leg to flex and extend the human-exoskeleton leg during the swing phase, and to augment knee extension during stance for stair or slope ascent. In addition, a motor might be placed in parallel with the leg spring that stores additional energy into the leg spring to augment leg extension in jumping or stair/hill ascent.

Metabolic Testing

Because the human leg acts like a linear spring in running and jumping, it is predicted that the exoskeleton spring legs would reduce the exertion in the human legs and thus reduce overall metabolic cost. This was verified when a human test subject jumped repeatedly for several minutes in the exoskeleton.

Experimental Methodology

An oxygen analyzer from Cosmed™ measured the volume of oxygen consumed per minute. The subject wore a mask that captured and analyzed the exhaled oxygen and the resulting data were transmitted wirelessly and saved on a computer.

To ensure reliability of test results, the room air, turbine, delay, and reference gas calibrations were performed on the oxygen analyzer. In addition, the subject refrained from smoking, caffeine, intense or prolonged exercise within the previous 24 hours before testing, and did not eat within 3 hours of the test but was well hydrated.

The subject jumped with the exoskeleton at a self-selected height and at a self-selected frequency. To maintain constant jumping frequency, a lab assistant counted the number of jumps in 10 seconds, calculated the average interval between jumps, and programmed this interval into a metronome which sounded beeps to signify when to jump. To regulate jumping height, a lab assistant marked the height of the subject's head at the peak of the jump on a white-board behind the subject's head. For the entire test, the lab assistant then informed the subject whether to increase or decrease his jumping height. These experimental steps were repeated for two different jumping heights: 4 inches and 8 inches.

Each jumping test was followed by a resting test where the subject sat for approximately 8 minutes. During the 8 minute time interval, the oxygen analyzer measured the resting metabolic rate.

Results

The subject jumped in the exoskeleton at a self-selected frequency to a height of 4 in while the metabolic rate was recorded via an oxygen analyzer. The subject's oxygen consumption leveled off at about 1500 ml/min. The exoskeleton was doffed and the subject repeated the test by jumping at the same frequency and to the same height, and the oxygen consumption level off to about 2050 ml/min. Each jumping test was followed by a resting period of at least 8 minutes, which had oxygen consumption levels around 300 ml/min.

The same jumping tests were repeated for a height of 8 in at a frequency that was self-selected for that height. The subject was able to jump continuously for 5 minutes with the exoskeleton, but when it was doffed, the subject could not finish the test due to exhaustion and muscle fatigue. This indicates that the exoskeleton can significantly augment human endurance for spring-like leg operations such as jumping and running.

Actuation

This section describes the actuation options at the hip, knee and ankle. Here the term actuation is used to describe the technological strategy employed to generate joint torque, whether the source is spring, variable damper or motor.

Series Elastic Actuator Design

Figure 38:
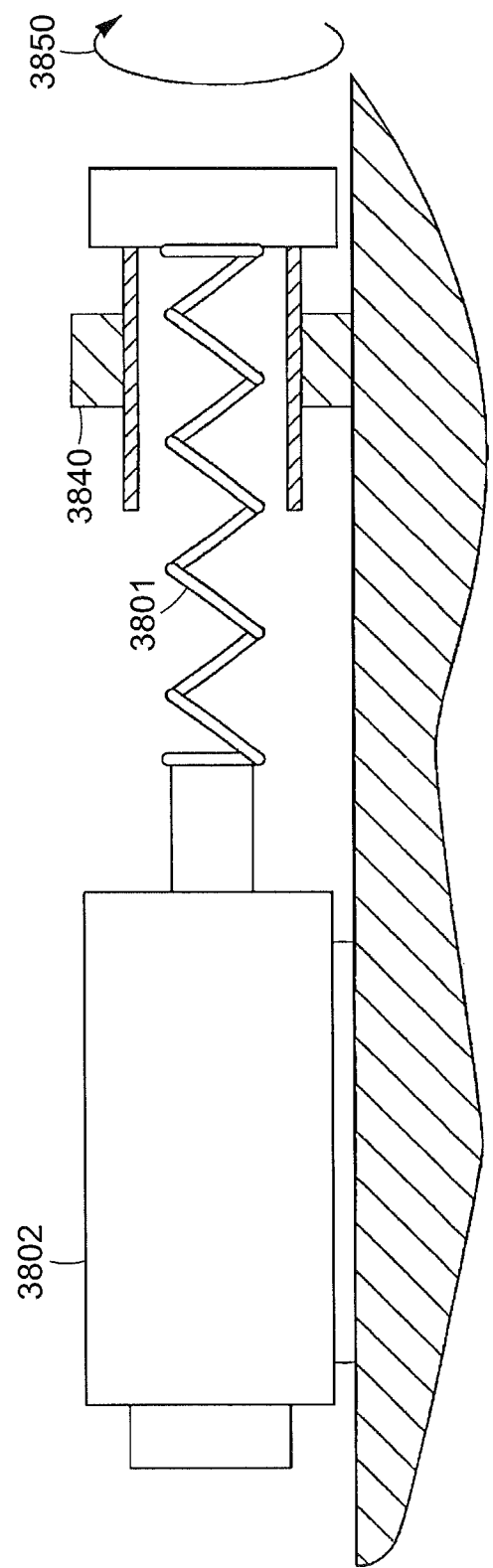
FIG. 38 is a schematic depiction of a series elastic actuator for the hip exoskeleton section.
Figure 39:
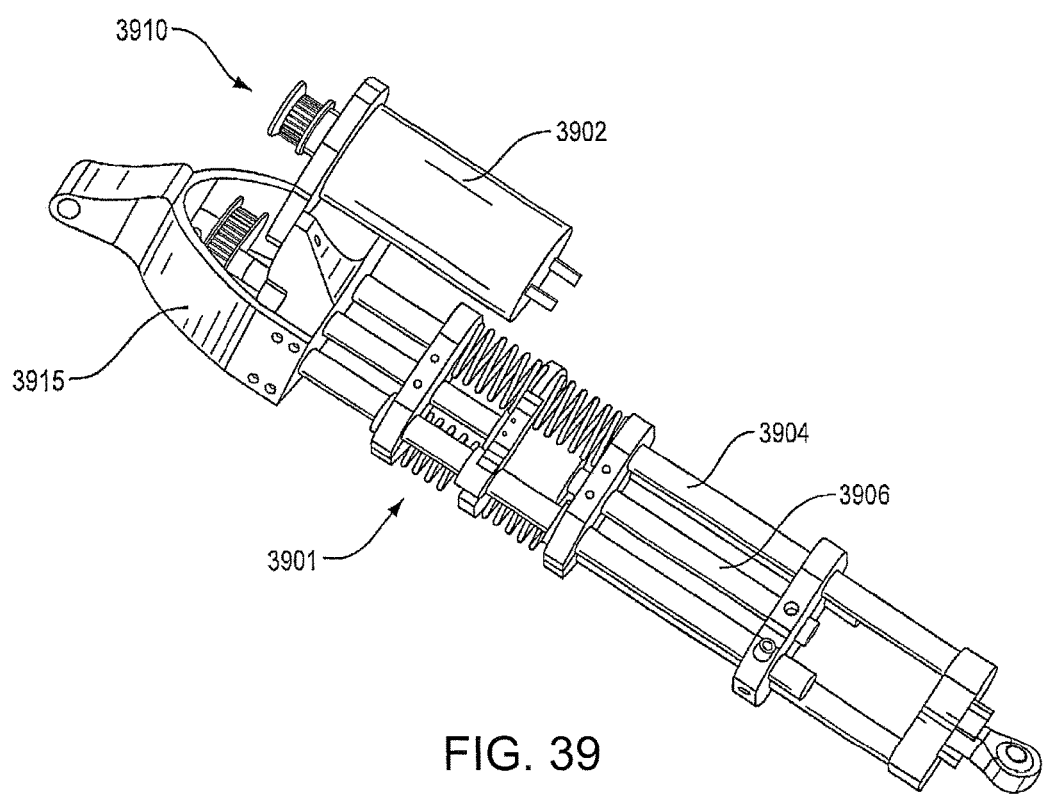
FIG. 39 is a perspective view of a series elastic actuator for the hip exoskeleton section.

Series elastic actuators (SEA) illustrated in FIGS. 38 and 39 were chosen as they provide a means for implementing lightweight and inexpensive force control with a bandwidth similar to that of natural muscle. Shown in FIG. 38 are spring 3801, motor/gearbox 3802, bearing 3840, and output 3850. As shown in FIG. 39, the SEA has a spring 3901 in series with the output of the motor 3902. The spring acts as a sensor, filter and impedance limiter. The ball screw nut is coupled to the output through four die compression springs in the assembly 3901 and the spring compression is measured with a linear potentiometer. Aluminum guide rods 3904 extend alongside the screw 3906. The motor pulley at 3910 is coupled to the screw bh a 2:1 belt reduction. The motor 3902 and the spring assembly are attached to an attachment yoke 3915 which attaches to the bearing mount on the harness.

Based on the human walking data described earlier, a 100 to 150 Watt Motor is sufficient to augment hip flexion-extension movements during level ground ambulation. A Maxon RE40 Brushed motor DC motor at 3902 is selected for its power to weight ratio. The ball screw and nut is from Nook Industries. The springs are die Springs from Century Spring. In designing the actuator the moment arm on the hip joint and the force output from the actuator must be calculated.

Actuator Characterization

When the actuator as seen in FIG. 39 is used at the hip of the exoskeleton, it experiences two boundary conditions. The actuator may be either directly in contact with the environment or it may be connected to a freely moving inertial load. These boundary conditions represent the stance and swing phase of the walking cycle, respectively. During the stance phase, the load position can be considered a fixed position source, and in the swing phase, the load position is defined as a function of the force in the spring and the load mass. These boundary conditions are characterized separately in order to determine the performance of the actuator for each case.

Closed Loop Characterization and Force Control

The closed loop control of the SEA can be obtained from Robinson (2000). For the fixed end condition, this represents the stance phase of the walking cycle. The actuator can be controlled with a pure proportional controller alone. This works well for the free end condition but does not work well for the case where the end is fixed. With pure P control, if the system hits a hard boundary, it will bounce back due to the large impact force borne by the sensor (spring) and the resulting large error signal with opposite sign. However, for a controllable actuator, it is desired that the actuator to remain at the point where a collision occurs. For this a lead-compensator is used that damps out the movement. A disadvantage of this is that the performance of the free movement of the actuator is degraded. The P and D gains can only be increased so far before the noise in the sensor signal is amplified.

Figure 40A:
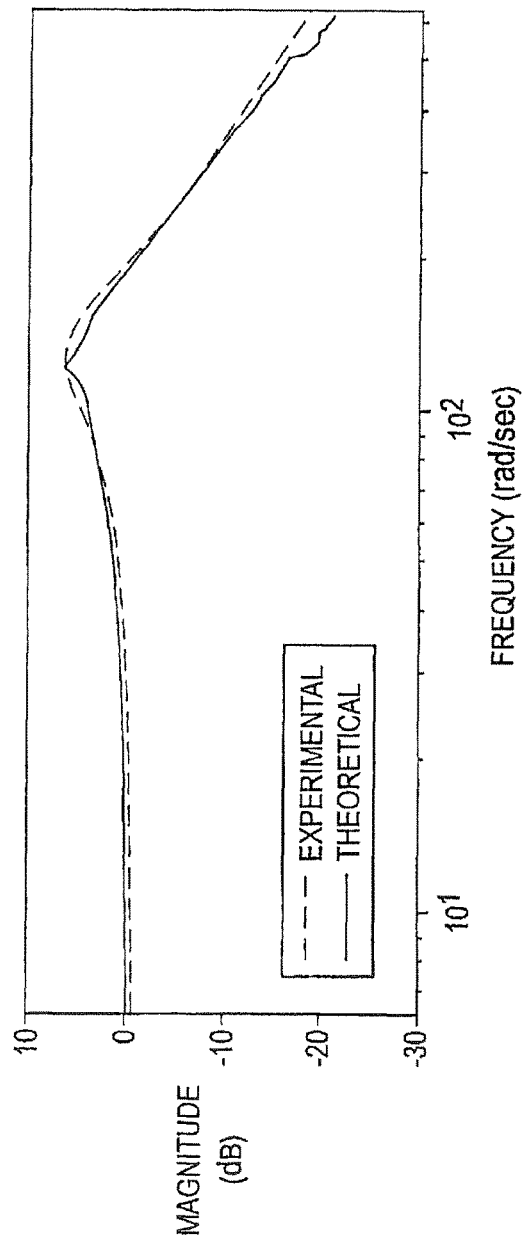
FIGS. 40A and 40B are Bode diagrams of the series elastic actuator for the fixed end condition.
Figure 40B:
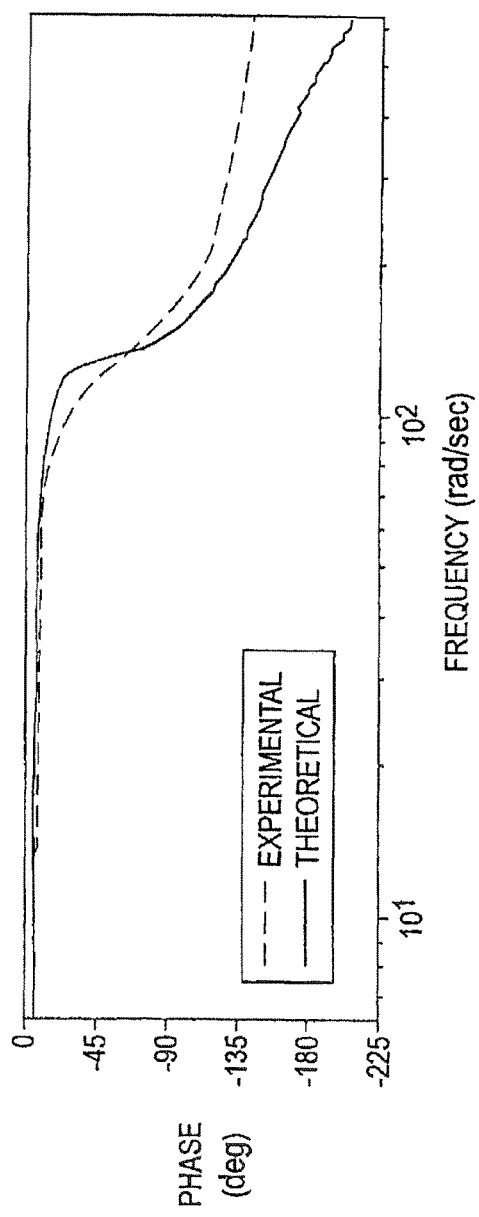

A resolution to this difficulty is to have a PD controller where the D term is a band limited differentiator. This is the controller that is shown below in a bode plot of the controller. In order to determine the closed-loop bandwidth of the actuator, the end of the actuator is fixed, and a sine wave chirp in force is applied from 1 Hz to 100 Hz. FIGS. 40A-B show both the experimental and theoretical closed loop Bode plots showing the experimental and compensated $2^{nd}$ Order model for a fixed end condition. Experimentally the −3 dB point is found to be at 226/rad/s (36 Hz).

The proportional P, and derivative D, gains of the controller are tuned experimentally based upon the step response of the actuator and the ability of the actuator to track a sine wave in force.

Closed Loop Performance with Load Mass

Figure 41A:
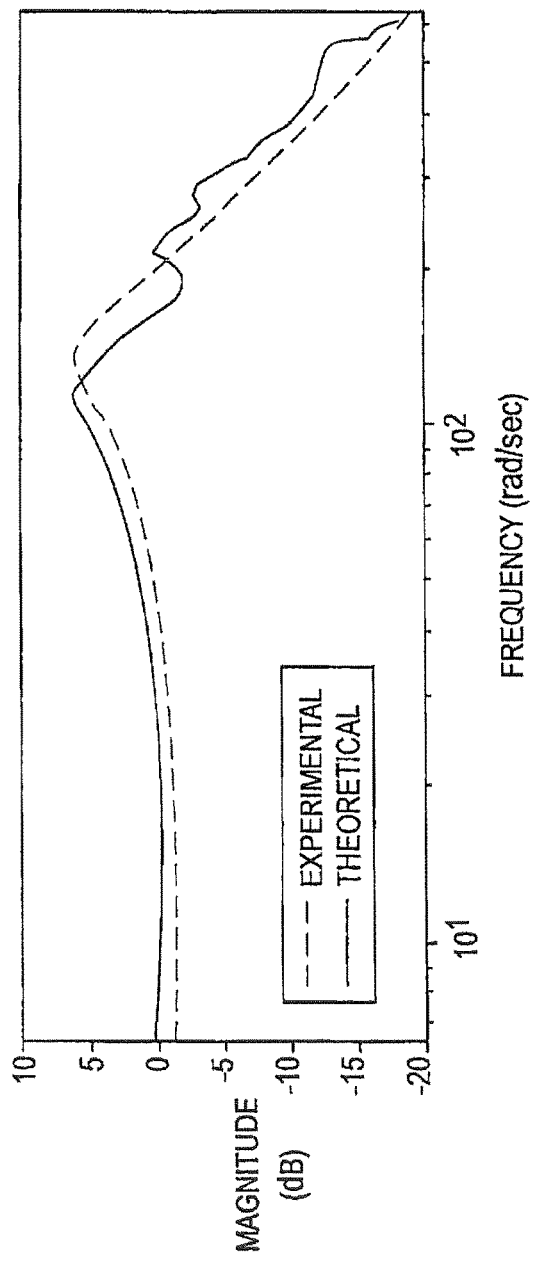
FIGS. 41A and 41B are Bode diagrams of the series elastic actuator with an equivalent load mass of 350 kg.
Figure 41B:
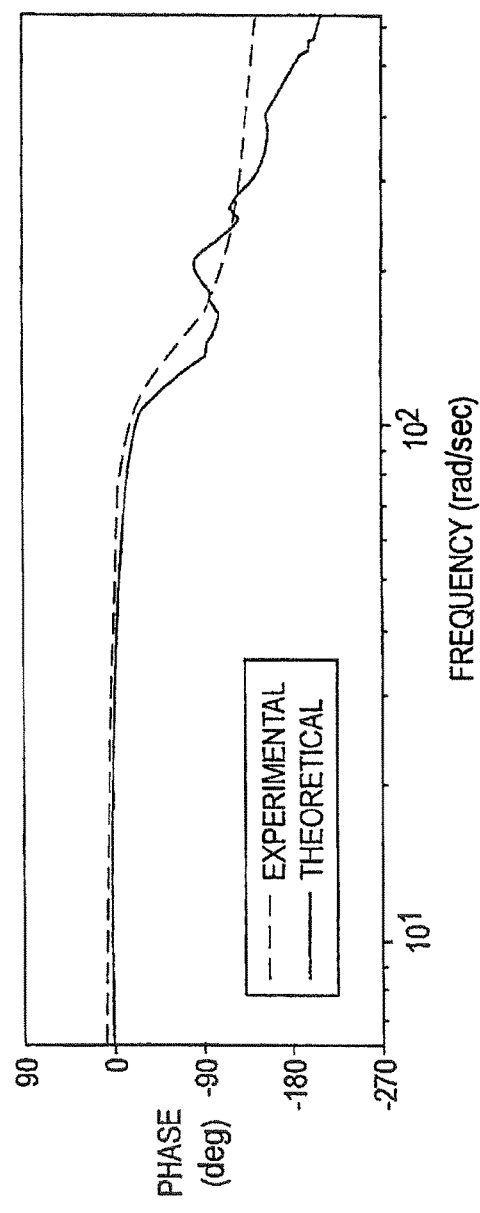

The actuator will have to apply a torque to the human and exoskeleton leg during the swing phase of the walking cycle. As a result, a test is completed in order to determine the closed loop bandwidth for the case of apply a force to a load mass in space. Shown in FIGS. 41A-B are the experimental and theoretical closed loop Bode plots for the actuator with the load mass end condition. The −3 dB point for the experimental curve is 253 rad/s (40.3 Hz) and the theoretical model is 230 rad/s (36 Hz).

Figure 42A:
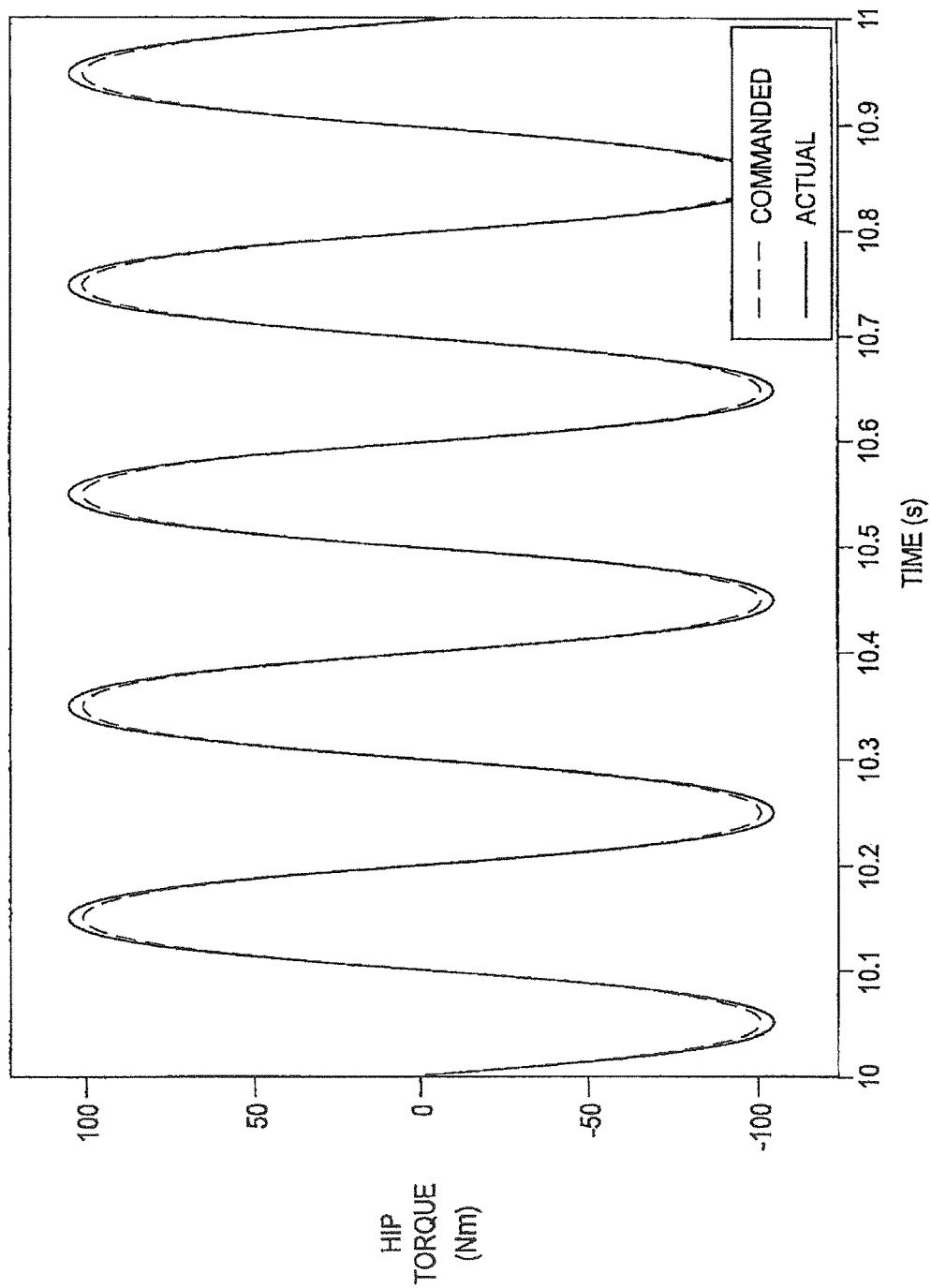
FIGS. 42A and 42B are graphs of hip toque and hip angle during closed loop testing of the actuator.

It is shown that the case of applying a force to a mass in space is similar to the case of the fixed end condition. As a result, the controller that is experimentally tuned for the case when the end condition is fixed should work well for the case when moving a load mass. In order to validate this theory a number of simple tests can be performed. FIG. 42A is a plot showing the actuator tracking a hip torque of 100 Nm at a frequency of 5 Hz with an equivalent mass to that of the human and exoskeleton leg (Linear force of 1600N).

Figure 42B:
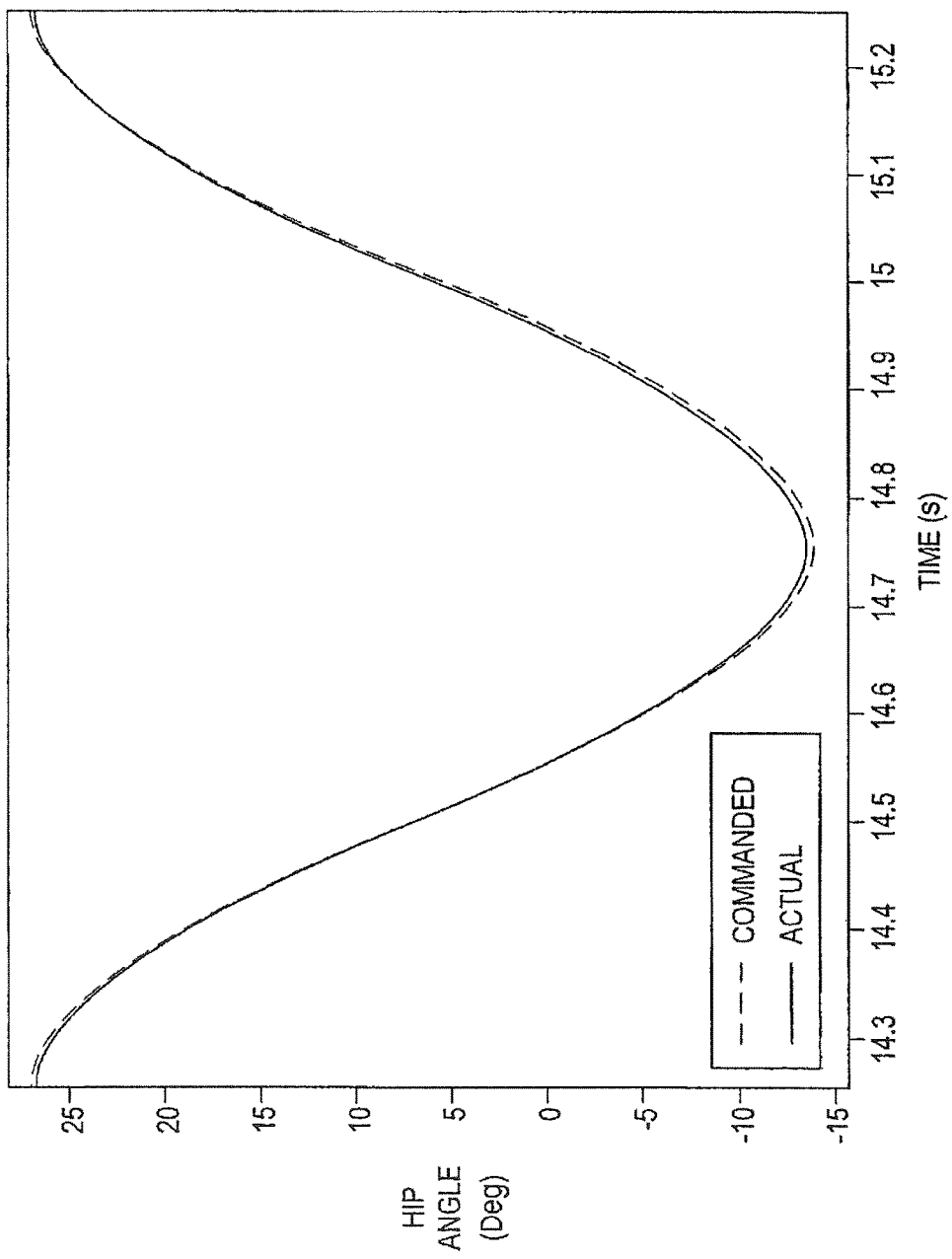

In order to determine if the actuator has sufficient force and power capability to power the human and exoskeleton, a test is performed where the actuator is commanded to track a trajectory similar to the human hip trajectory in walking. The test is performed on the bench with an equivalent mass on the end of the arm. FIG. 42B shows closed loop position control testing wherein the actuator is commanded to track a trajectory similar to that of the human hip joint in walking.

It is to be understood that the methods and apparatus which have been described above are merely illustrative applications of the principles of the invention. Numerous modifications may be made by those skilled in the art without departing from the true spirit and scope of the invention.

What is claimed is:

1. An exoskeleton worn by a human user, comprising, in combination:
    a pelvic harness adapted to be worn about a waist of the user;
    a load bearing exoskeleton leg structure adapted to extend along the side of the leg of the human user and including a thigh member adapted to be positioned to the side of a thigh of the human user, a shin member adapted to be positioned to the side of a shin of the human user, and a knee joint joining the thigh member and the shin member and adapted to be positioned to the side of the knee of the human user, the thigh member comprising a bearing housing component and a shaft component, the bearing housing component and the shaft component collectively adapted to extend downwardly alongside the leg of the human user, and wherein the bearing housing and shaft components are configured such that a length of the exoskeleton leg structure is determined by the position of the exoskeleton leg structure in a coronal plane of the human user, the position of the exoskeleton leg structure thereby defining a set of lengths, and wherein the length of the exoskeleton leg structure is automatically adjusted among the lengths of the set of lengths during abduction and adduction of the exoskeleton leg structure in the coronal plane of the human user to compensate for variations between a length of the human user's leg and the length of the exoskeleton leg structure resulting from dissimilar centers of rotation between the human user's leg and the exoskeleton leg structure, there being a unique leg length of the exoskeleton leg structure for a given leg abduction angle of the exoskeleton leg structure;
    a hip joint at the pelvic harness linking the exoskeleton thigh member at the bearing housing component to the pelvic harness;
    a thigh cuff attached to the exoskeleton leg structure at the thigh member distal to the pelvic harness, the thigh cuff being adapted to be attached to the thigh of the human user;
    a foot member adapted to be attached to a shoe worn by the human user;
    an ankle joint joining the shin member to the foot member and adapted to be positioned to the side of the ankle of the human user;
    a passive spring or an active actuator coupled at the hip joint between the thigh member and the pelvic harness to apply a motive force for rotating the thigh member with respect to the pelvic harness to assist in lifting the exoskeleton and the human user with respect to a ground surface upon which the user is walking and to propel the exoskeleton and human user forward;
    a controllable damper operatively connected to the knee joint for arresting the relative movement of the shin member and the thigh member at controllable times; and
    a spring located in the foot member or the ankle joint for storing and releasing energy during walking.

2. An exoskeleton as set forth in claim 1, wherein a length of the shin member is adjustable to accommodate human users of different sizes.

3. An exoskeleton as set forth in claim 2, wherein a length of the thigh member is adjustable to accommodate human users of different sizes.

4. An exoskeleton as set forth in claim 1, wherein the pelvic harness is attached to a load-carrying backpack adapted to be worn on a back of the human user, the backpack being supported on the ground surface by the exoskeleton leg structure.

5. An exoskeleton as set forth in claim 1, wherein the pelvic harness is attached to a seat adapted to support the human user so that a significant part of a weight of the human user is born by the exoskeleton leg structure.

6. The exoskeleton of claim 1, further including a cam-roller mechanism coupling the pelvic harness, the bearing housing component and the shaft component, the cam-roller mechanism having one degree of freedom, so that for a given leg abduction angle, there is a unique leg length of the exoskeleton leg structure.

7. An exoskeleton worn by a human user, comprising:
a) a pelvic harness adapted to be worn about a waist of the user;
b) a load bearing exoskeleton leg structure adapted to extend along the side of the leg of the human user and including a thigh member adapted to be positioned to the side of a thigh of the human user, a shin member adapted to be positioned to the side of a shin of the human user, and a knee joint joining the thigh member and the shin member and adapted to be positioned to the side of the knee of the human user, the thigh member comprising;
 i) a bearing housing component, and
 ii) a shaft component,
 wherein the bearing housing component and the shaft component are collectively adapted to extend downward alongside the leg of the human user, and
 wherein the bearing housing and shaft components are configured such that a length of the exoskeleton leg structure is determined by the position of the exoskeleton leg structure in a coronal plane of the human user to form a set of lengths of the exoskeleton leg structure, and is automatically adjusted among the lengths of the set of lengths during abduction and adduction of the structure in the coronal plane of the human user to compensate for variations between a length of the human user's leg and the length of the exoskeleton leg structure resulting from dissimilar centers of rotation between the human user's leg and the exoskeleton leg structure, there being a unique leg length of the exoskeleton leg structure for a given leg abduction angle of the exoskeleton leg structure;
c) a hip joint at the pelvic harness linking the exoskeleton thigh member at the bearing housing component to the pelvic harness; and
d) a thigh cuff attached to the thigh member distal to the pelvic harness, the thigh cuff being adapted to be attached to the thigh of the human user.

8. The exoskeleton of claim 7, further including a cam-roller mechanism coupling the pelvic harness, the bearing housing component and the shaft component, the cam-roller mechanism having one degree of freedom, so that for a given leg abduction angle of the exoskeleton leg structure, there is a unique leg length of the exoskeleton leg structure.

* * * * *